United States Patent
Nakanishi

(10) Patent No.: US 10,596,317 B2
(45) Date of Patent: Mar. 24, 2020

(54) PHARMACEUTICAL INJECTION SYSTEM, PORTABLE TERMINAL, PHARMACEUTICAL INJECTION DEVICE, HEALTH CARE WORKER-USE INFORMATION TERMINAL, AND METHOD FOR CONTROLLING PHARMACEUTICAL INJECTION SYSTEM

(71) Applicant: PHC HOLDINGS CORPORATION, Tokyo (JP)

(72) Inventor: Katsumi Nakanishi, Ehime (JP)

(73) Assignee: PHC HOLDINGS CORPORATION, Tokyo (JP)

( * ) Notice: Subject to any disclaimer, the term of this patent is extended or adjusted under 35 U.S.C. 154(b) by 226 days.

(21) Appl. No.: 15/509,128

(22) PCT Filed: Sep. 29, 2015

(86) PCT No.: PCT/JP2015/077433
§ 371 (c)(1),
(2) Date: Mar. 6, 2017

(87) PCT Pub. No.: WO2016/052464
PCT Pub. Date: Apr. 7, 2016

(65) Prior Publication Data
US 2017/0281866 A1 Oct. 5, 2017

(30) Foreign Application Priority Data
Sep. 30, 2014 (JP) .................................. 2014-199815

(51) Int. Cl.
*A61M 5/172* (2006.01)
*G16H 20/17* (2018.01)
(Continued)

(52) U.S. Cl.
CPC ........ *A61M 5/172* (2013.01); *A61M 5/14566* (2013.01); *A61M 5/168* (2013.01);
(Continued)

(58) Field of Classification Search
CPC ........ G16H 20/17; G16H 10/00; G16H 10/40; G16H 10/60; G16H 15/00; G16H 20/00;
(Continued)

(56) References Cited

U.S. PATENT DOCUMENTS

2008/0086086 A1 4/2008 Field et al.
2008/0235053 A1 9/2008 Ray et al.
(Continued)

FOREIGN PATENT DOCUMENTS

JP 2004-000555 A 1/2004
JP 2004-261274 A 9/2004
(Continued)

OTHER PUBLICATIONS

International Search Report issued in Patent Application No. PCT/JP2015/077433 dated Dec. 15, 2015.
(Continued)

*Primary Examiner* — Jenna Zhang
(74) *Attorney, Agent, or Firm* — Pearne & Gordon LLP

(57) ABSTRACT

With the pharmaceutical injection system in an embodiment, pharmaceutical injection amount setting conditions for setting a pharmaceutical injection amount are inputted to a portable terminal (300), and the pharmaceutical injection amount setting conditions are transmitted to a health care worker-use information terminal (500). The portable terminal (300) receives the pharmaceutical injection amount set on the basis of the pharmaceutical injection amount setting conditions transmitted from the health care worker-use information terminal (500), and transmits the pharmaceutical injection amount to a pharmaceutical injection device
(Continued)

(100). The health care worker-use information terminal (500) receives the pharmaceutical injection amount setting conditions transmitted from the portable terminal (300), and the pharmaceutical injection amount set on the basis of the pharmaceutical injection amount setting conditions is inputted. The health care worker-use information terminal (500) transmits the inputted pharmaceutical injection amount to the portable terminal (300). The pharmaceutical injection device (100) receives the pharmaceutical injection amount transmitted from the portable terminal (300), and a piston drive mechanism (101) is driven on the basis of the pharmaceutical injection amount.

12 Claims, 42 Drawing Sheets

(51) Int. Cl.
| | |
|---|---|
| G06F 19/00 | (2018.01) |
| G06Q 50/24 | (2012.01) |
| G16H 10/60 | (2018.01) |
| G16H 80/00 | (2018.01) |
| A61M 5/145 | (2006.01) |
| A61M 5/142 | (2006.01) |
| A61M 5/168 | (2006.01) |
| G16H 70/40 | (2018.01) |
| G16H 40/67 | (2018.01) |
| G16H 40/63 | (2018.01) |
| G16H 40/60 | (2018.01) |
| G16H 10/00 | (2018.01) |
| G16H 20/00 | (2018.01) |
| G16H 15/00 | (2018.01) |
| G16H 20/10 | (2018.01) |
| G16H 70/00 | (2018.01) |

(52) U.S. Cl.
CPC ......... *G06F 19/3468* (2013.01); *G06Q 50/24* (2013.01); *G16H 10/60* (2018.01); *G16H 20/17* (2018.01); *G16H 40/63* (2018.01); *G16H 40/67* (2018.01); *G16H 70/40* (2018.01); *G16H 80/00* (2018.01); *A61M 2005/14208* (2013.01); *A61M 2205/3561* (2013.01); *A61M 2205/3592* (2013.01); *A61M 2205/50* (2013.01); *A61M 2205/502* (2013.01); *A61M 2205/505* (2013.01); *A61M 2205/52* (2013.01); *A61M 2205/8206* (2013.01); *A61M 2230/201* (2013.01); *G16H 10/00* (2018.01); *G16H 15/00* (2018.01); *G16H 20/00* (2018.01); *G16H 20/10* (2018.01); *G16H 40/60* (2018.01); *G16H 70/00* (2018.01)

(58) Field of Classification Search
CPC ........ G16H 20/10; G16H 20/13; G16H 40/00; G16H 40/60; G16H 40/63; G16H 40/67; G16H 50/00; G16H 70/00; G16H 70/40; G16H 80/00; A61M 5/14566; A61M 5/168; A61M 2005/14208; A61M 2205/3592; A61M 2205/50; A61M 2205/502; A61M 2205/505; A61M 2205/52; A61M 2205/8206; A61M 2230/201; G06F 19/3468; G06F 19/30; G06F 19/32; G06F 19/34; G06Q 50/22; G06Q 50/24

See application file for complete search history.

(56) References Cited

U.S. PATENT DOCUMENTS

| | | | | |
|---|---|---|---|---|
| 2008/0262469 | A1* | 10/2008 | Brister | A61B 5/0002 604/504 |
| 2008/0306434 | A1* | 12/2008 | Dobbles | A61B 5/14546 604/66 |
| 2009/0069787 | A1* | 3/2009 | Estes | A61M 5/1413 604/503 |
| 2011/0124996 | A1* | 5/2011 | Reinke | A61M 5/14248 600/365 |
| 2012/0330228 | A1* | 12/2012 | Day | A61M 5/14248 604/82 |
| 2014/0005603 | A1 | 1/2014 | Holtwick et al. | |
| 2015/0328404 | A1 | 11/2015 | Murakami et al. | |

FOREIGN PATENT DOCUMENTS

| | | |
|---|---|---|
| JP | 2008-229331 A | 10/2008 |
| JP | 2010-505593 A | 2/2010 |
| JP | 2012-034729 A | 2/2012 |
| JP | 2014-507223 A | 3/2014 |
| WO | 2014-091765 A1 | 6/2016 |

OTHER PUBLICATIONS

Written Opinion issued in Patent Application No. PCT/JP2015/077433 dated Dec. 15, 2015.
Extended European Search Report issued in Patent Application No. 15 84 5990 dated Sep. 14, 2017.
Japanese Office action issued in Patent Application No. JP-2016-552039 dated Sep. 4, 2018.

* cited by examiner

FIG. 23

| Date | 2/26 | 2/27 | 2/28 | 3/1 | 3/2 | 3/3 | 3/4 |
|---|---|---|---|---|---|---|---|
| Adjustment amount in pharmaceutical administration | none | somewhat high | somewhat low | high | somewhat high | none | somewhat high |
| Blood glucose | normal | high | low | high | high | normal | high |
| Meal size | normal | large | small | large | normal | small | small |
| Activity | normal | high | normal | low | low | low | low |
| Administration date | on sched. | on sched. | on sched. | on sched. | on sched. | on sched. | on sched. |
| Valid adjustment amount (five-stage), weighted | none | somewhat high | low | high | high | none | somewhat high |
| Point total | 0 | 2.5 | −3.5 | 4.5 | 3 | −0.5 | 1.5 |
| Determination result (example) | good | good | fair | good | fair | good | good |
| Evaluation comments by physician, advice to patient (example) |  | Since blood glucose was low the next day, either the dose may not be adjusted, or activity may be reduced | A small adjustment amount is preferable, but a higher blood glucose level the next day may be a result of that | Let's reduce meal size and do some exercise | An increase is preferable for the adjustment amount. It was good that blood glucose level was returned normal level on the next day |  |  |

FIG. 24

| Date | 2/26 | 2/27 | 2/28 | 3/1 | 3/2 | 3/3 | 3/4 |
|---|---|---|---|---|---|---|---|
| Adjustment amount in pharmaceutical administration | none | none | somewhat low | high | high | none | none |
| Blood glucose | normal | high | low | high | high | normal | high |
| Meal size | normal | large | small | large | normal | small | small |
| Activity | normal | high | normal | low | low | low | low |
| Other | on sched. | on sched. | on sched. | on sched. | on sched. | on sched. | on sched. |
| Valid adjustment amount (three-stage), weighted | none | high | low | high | high | none | none |
| Point total | 0 | 2.5 | −3.5 | 4.5 | 3 | −0.5 | 1.5 |
| Determination result (example) | good | fair | good | good | good | good | good |
| Evaluation comments by physician, advice to patient (example) |  | A large adjustment amount is preferable; let's reduce meal size |  | Let's reduce meal size and do some exercise | Let's do some exercise |  |  |

Setting information about dose adjustment

Ex.:　　reference dose　　　　40 units　　　* set according to patient's condition and body weight — Adjustment mode:　simple mode Ex.:　With five-stage adjustment amount level 1　　+5 units
　　adjustment amount level 2　　+2 units
　　adjustment amount level 3　　±0 units
　　adjustment amount level 4　　−4 units
　　adjustment amount level 5　　−8 units Ex.:　With three-stage adjustment amount level 1　　+3 units
　　adjustment amount level 2　　±0 units
　　adjustment amount level 3　　−5 units
　　adjustment amount level 4　　not used
　　adjustment amount level 5　　not used

FIG. 30A

Change reason data for dose adjustment
Ex.: Change reason 1  blood glucose level 1 text  "high"
    level 1 help  "average blood glucose level over the past two to three days is above 200 mg/dL, and is above 160 mg/dL before breakfast"
    level 2 text  "normal"
    level 2 help  "average blood glucose level over the past two to three days is 80 to 200 mg/dL, and is 60 to 160 mg/dL before breakfast"
    level 3 text  "low"
    level 3 help  "average blood glucose level over the past two to three days is below 80 mg/dL, and is below 60 mg/dL before breakfast"

Ex.: Change reason 2  meal size    * under restricted diet level 1 text  "large"
    level 1 help  "intake energy is above 1200 kcal/day and carbohydrate count is above 500 g/day"
    level 2 text  "normal"
    level 2 help  "intake energy is 600 to 1200 kcal/day and carbohydrate count is 200 to 500 g/day"
    level 3 text  "low"
    level 3 help  "intake energy is below 600 kcal/day and carbohydrate count is below 200 g/day"

Ex.: Change reason 3  Activity level 1 text  "low"
    level 1 help  "consumed energy is below 1000 kcal/day, number of steps is below 2000 per day, and metabolic equivalents is below 1 per day"
    level 2 text  "normal"
    level 2 help  "consumed energy is 1000 to 2000 kcal/day, number of steps is 2000 to 10,000 per day, and metabolic equivalents is 1 to 5 per day"
    level 3 text  "high"
    level 3 help  "consumed energy is above 2000 kcal/day, number of steps is above 10,000 per day, and metabolic equivalents is above 5 per day"

Ex.: Change reason 4  Other level 1 text  "late"
    level 1 help  "user has forgotten to take an injection, etc."
    level 2 text  "on schedule"
    level 2 help  ""
    level 3 text  "early"
    level 3 help  "when the user wants to take an injection before going out(when it is done earlier than the scheduled time)."
              "user wants to take additional injection because dose was too low previous time, etc."

FIG. 30B

· Combinations of change reasons and adjustment amount weighting parameters

Ex.: Five-stage adjustment amount, weighted

| | Change reason 1, blood glucose | Change reason 2, meal size | Change reason 3, activity | Change reason 4, other |
|---|---|---|---|---|
| Change reason level 1 (adjustment amount "increase" cause) | 2 | 1.5 | 1 | 0.5 |
| Change reason level 2 (adjustment amount "unnecessary" cause) | 0 | 0 | 0 | 0 |
| Change reason level 3 (adjustment amount "decrease" cause) | -2 | -1.5 | -1 | -0.5 |

| Add points for change reason level on day of input |
|---|

| Adjustment amount level 1 "high" | |
| Adjustment amount level 2 "somewhat high" | |
| Adjustment amount level 3 "" | (since "normal" is not displayed) |
| Adjustment amount level 4 "somewhat low" | |
| Adjustment amount level 5 "low" | |

| Adjustment point total calculation formula |
|---|

| If point total is +3 to +5 |
| If point total is +1.5 to +2.5 |
| If point total is -1 to +1 |
| If point total is -2.5 to -1.5 |
| If point total is -5 to -3 |

Ex.: Three-stage adjustment amount, unweighted

| | Change reason 1, blood glucose | Change reason 2, meal size | Change reason 3, activity | Change reason 4, other |
|---|---|---|---|---|
| Change reason level 1 (adjustment amount "increase" cause) | 1 | 1 | 1 | 1 |
| Change reason level 2 (adjustment amount "unnecessary" cause) | 0 | 0 | 0 | 0 |
| Change reason level 3 (adjustment amount "decrease") cause | -1 | -1 | -1 | -1 |

| Add points for change reason level on day of input |
|---|

| Adjustment amount level 1 "high" | |
| Adjustment amount level 2 "" | (since "normal" is not displayed) |
| Adjustment amount level 3 "low" | |

| Adjustment point total calculation formula |
|---|

| If point total is +2 to +4 |
| If point total is -1 to +1 |
| If point total is -4 to -2 |

FIG. 30C

■ Data (administration log data) transmitted from pharmaceutical injection device (injector) to health care worker-use information terminal (PC)

· Pharmaceutical administration information (administration log data)

Ex.:
Administration date:       3/5/14
Administration time:       1:00 pm
Reference dose:            40 units
Adjusted dose:             45 units
Change reason 1:           large meal size             (or small meal size)
Change reason 2:           high blood glucose level    (or low blood glucose level)
Change reason 3:           none                        (high or low activity level)
Change reason 4:           none                        (later or earlier than scheduled)

FIG. 35

PHARMACEUTICAL INJECTION SYSTEM, PORTABLE TERMINAL, PHARMACEUTICAL INJECTION DEVICE, HEALTH CARE WORKER-USE INFORMATION TERMINAL, AND METHOD FOR CONTROLLING PHARMACEUTICAL INJECTION SYSTEM

TECHNICAL FIELD

The present invention relates to a pharmaceutical injection system that injects insulin, growth hormone, or another such pharmaceutical, for example, and to a portable terminal, a health care worker-use information terminal, and so forth used in this system.

BACKGROUND ART

A conventional pharmaceutical injection system of this type is made up of a pharmaceutical injection device and a storage medium that is removably mounted to this pharmaceutical injection device, and is designed so that when the storage medium is mounted to the pharmaceutical injection device, the pharmaceutical injection amount is set automatically (see Patent Literature 1 below, for example).

With the pharmaceutical injection device in Patent Literature 1, a health care worker takes an individual's condition into account, and stores a pharmaceutical injection amount for each individual in the storage medium, so the pharmaceutical injection amount can be set automatically merely by mounting this storage medium to the pharmaceutical injection device.

CITATION LIST

Patent Literature

Patent Literature 1: Japanese Laid-Open Patent Application 2012-34729

SUMMARY

Technical Problem

However, in order to change the pharmaceutical injection amount according to how each individual fights a disease, a visit to a medical facility is required every time, which is inconvenient for the user.

In view of this, it is an object of the present invention to provide a pharmaceutical injection system, a portable terminal, a health care worker-use information terminal, a pharmaceutical injection device, and a method for controlling a pharmaceutical injection system, with which convenience is improved by making it possible to change the pharmaceutical injection amount without having to go to a medical facility.

Solution to Problem

To achieve this object, the pharmaceutical injection system of the present invention comprises a pharmaceutical injection device that injects a pharmaceutical, a portable terminal that sets the pharmaceutical injection amount for the pharmaceutical injection device, and a health care worker-use information terminal that is capable of communicating with the portable terminal.

The portable terminal has a first input component, a first transmitter, a first receiver, and a second transmitter. Pharmaceutical injection amount setting conditions for setting the pharmaceutical injection amount are inputted to the first input component. The first transmitter transmits the inputted pharmaceutical injection amount setting conditions to the health care worker-use information terminal. The first receiver receives a pharmaceutical injection amount set on the basis of the pharmaceutical injection amount setting conditions transmitted from the health care worker-use information terminal. The second transmitter transmits the received pharmaceutical injection amount to the pharmaceutical injection device.

The health care worker-use information terminal has a second receiver, a second input component, and a third transmitter. The second receiver receives the pharmaceutical injection amount setting conditions transmitted from the portable terminal. A pharmaceutical injection amount set on the basis of the received pharmaceutical injection amount setting conditions is inputted to the second input component. The third transmitter transmits the inputted pharmaceutical injection amount to the portable terminal.

The pharmaceutical injection device has a cartridge holder, a main body case, a piston, a piston drive mechanism, a third receiver, and a controller. A pharmaceutical cartridge can be mounted in the cartridge holder. The cartridge holder is openably and closeably provided to the main body case. The piston can be inserted into the pharmaceutical cartridge mounted to the cartridge holder inside the main body case. The piston drive mechanism moves the piston so as to insert it into the pharmaceutical cartridge. The third receiver receives the pharmaceutical injection amount transmitted from the portable terminal. The controller drives the piston drive mechanism on the basis of the received pharmaceutical injection amount.

Accordingly, when the patient inputs pharmaceutical injection amount setting conditions from the first input component of the portable terminal, for example, the pharmaceutical injection amount set by a health care worker is transmitted through the portable terminal to the pharmaceutical injection device, so the pharmaceutical injection amount can be changed without having to go to a medical facility, which is extremely convenient for the user.

ADVANTAGEOUS EFFECTS

The present invention provides a pharmaceutical injection system, a portable terminal, a health care worker-use information terminal, a pharmaceutical injection device, and a method for controlling a pharmaceutical injection system, which are more convenient because the pharmaceutical injection amount can be changed without having to go to a medical facility.

BRIEF DESCRIPTION OF DRAWINGS

FIG. 23 is a table of comments by health care workers using the pharmaceutical injection system in a modification example of this embodiment;

FIG. 24 is a table of comments by health care workers using the pharmaceutical injection system in a modification example of this embodiment;

FIG. 30A shows setting information transmitted from the health care worker-use information terminal to the pharmaceutical injection device in the pharmaceutical injection system in FIG. 25;

FIG. 30B shows setting information transmitted from the health care worker-use information terminal to the pharmaceutical injection device in the pharmaceutical injection system in FIG. 25;

FIG. 30C shows setting information transmitted from the health care worker-use information terminal to the pharmaceutical injection device in the pharmaceutical injection system in FIG. 25;

FIG. 35 shows the data transmitted by the communication controller to the health care worker-use information terminal in the pharmaceutical injection system in FIG. 25.

DESCRIPTION OF EMBODIMENTS

An example of when a diabetes patient injects insulin (an example of a pharmaceutical) with the pharmaceutical injection system in an embodiment of the present invention will now be described through reference to the drawings.

Embodiment 1

1. Configuration

Overview of Pharmaceutical Injection System

Figure 1:
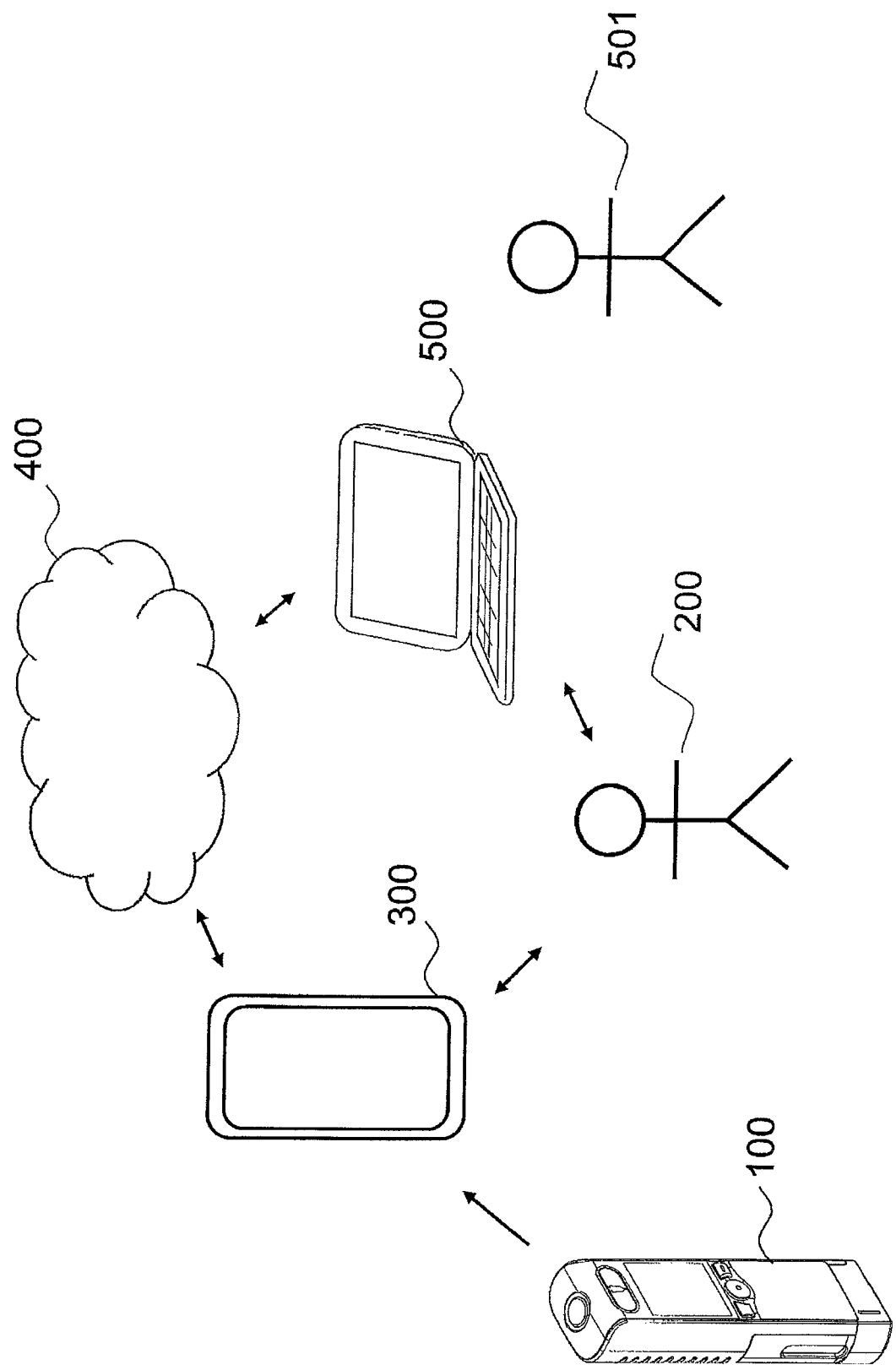
FIG. 1 is an oblique view of the pharmaceutical injection system pertaining to an embodiment of the present invention.

FIG. 1 shows the configuration of the pharmaceutical injection system in this embodiment. As shown in FIG. 1, the pharmaceutical injection system in this embodiment comprises a pharmaceutical injection device 100, a portable terminal 300, and a health care worker-use information terminal 500. The pharmaceutical injection device 100 is used to inject a pharmaceutical into a patient 200.

The portable terminal 300 belongs to the patient 200, and can set the pharmaceutical injection amount for the pharmaceutical injection device 100.

This portable terminal 300 is configured to allow communication with the health care worker-use information terminal 500 via a network 400. An example of the health care worker-use information terminal 500 is a personal computer belonging to a physician 501.

Pharmaceutical Injection Device

Figure 2:
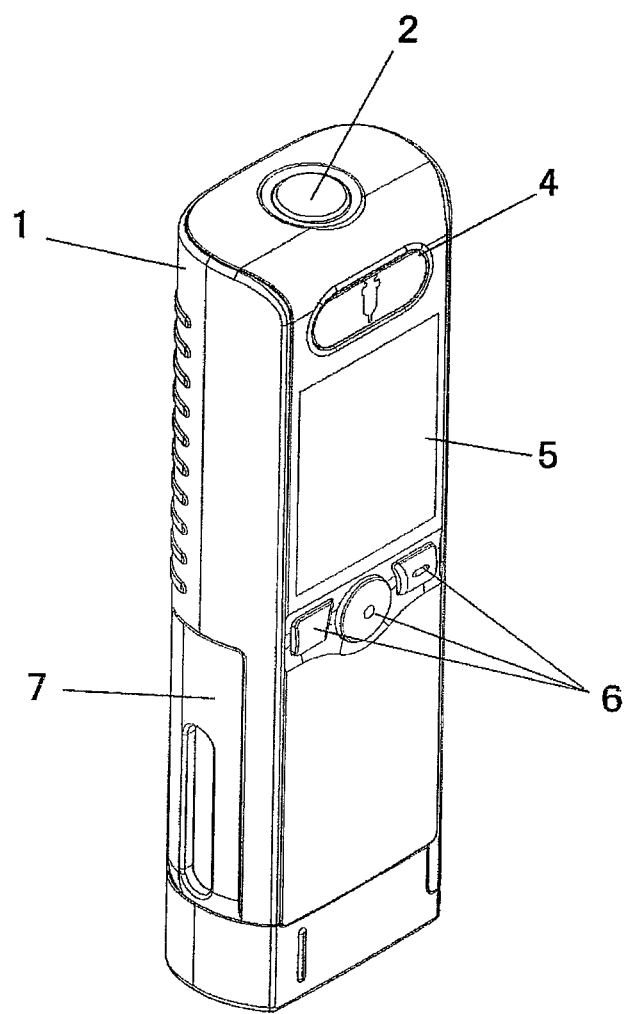
FIG. 2 is an oblique view of the pharmaceutical injection device used in the pharmaceutical injection system shown in FIG. 1.
Figure 3:
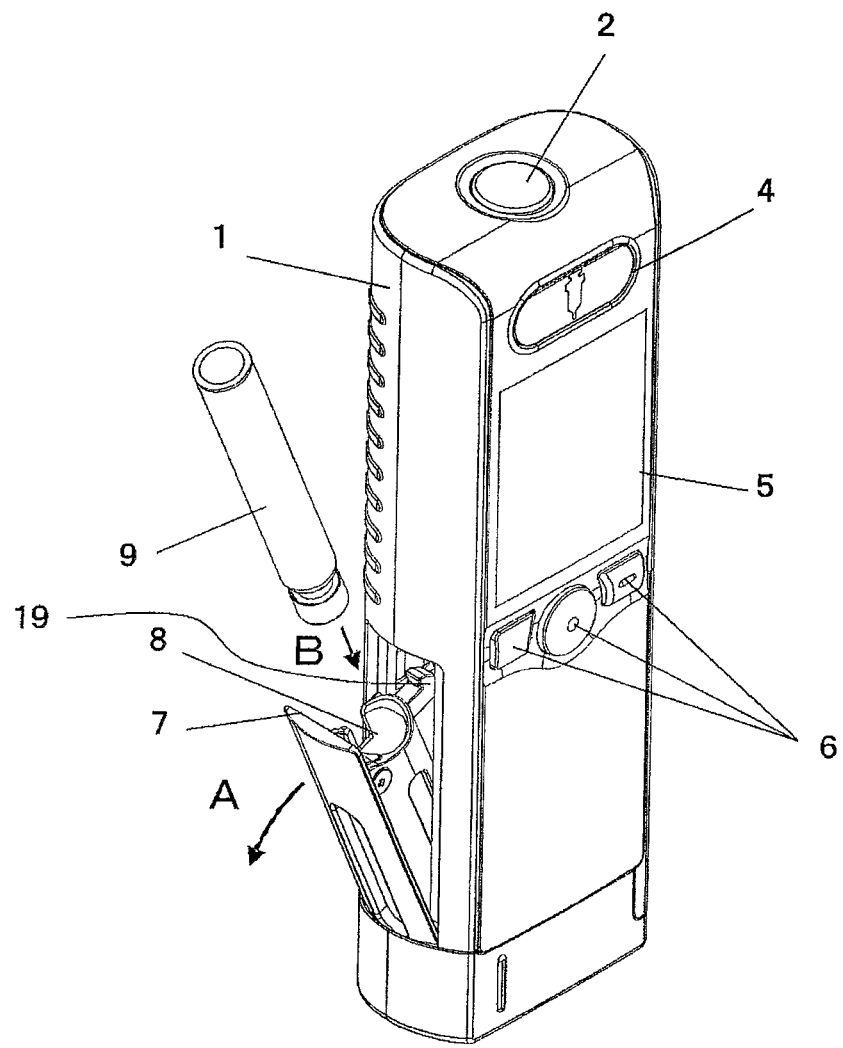
FIG. 3 is an oblique view of the state when the cartridge holder of the pharmaceutical injection device shown in FIG. 2 has been opened.
Figure 4:
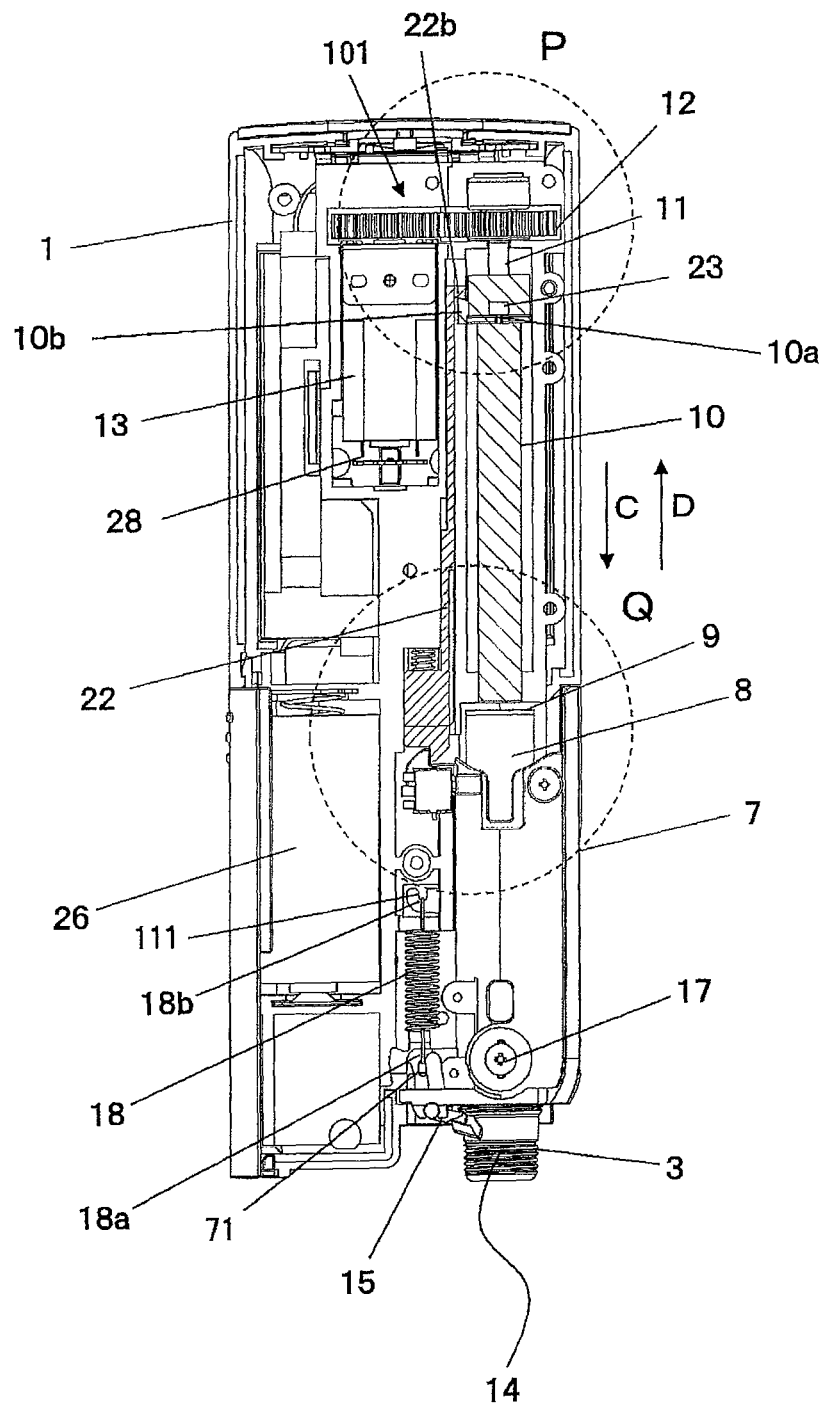
FIG. 4 is a front cross section of the internal configuration of the pharmaceutical injection device shown in FIG. 2.

FIG. 2 is an oblique view of the pharmaceutical injection device 100 in this embodiment. FIG. 3 is an oblique view of the state when a cartridge holder of the pharmaceutical injection device 100 in this embodiment has been opened. FIG. 4 is a front cross section of the internal configuration of the pharmaceutical injection device 100 in this embodiment.

As shown in FIGS. 2 and 3, the pharmaceutical injection device 100 in this embodiment comprises a cylindrical main body case 1 that can be held in one hand. A power switch 2 is provided to the upper face of this main body case 1, and an injection needle mounting component 3 is provided to the lower face as shown in FIG. 4. In the description in this Specification, the side on which the power switch 2 is provided shall be the top or the rear, and the side on which the injection needle mounting component 3 is provided (the opposite side) shall be the bottom or the front.

A pharmaceutical injection switch 4, a display component 5, and setting switches 6 for setting the pharmaceutical injection amount are provided in that order, from top to bottom, on the front portion of this main body case 1.

As shown in FIGS. 2 and 3, a cylindrical cartridge holder 7 is also provided openably and closeably to the main body case 1.

That is, the cartridge holder 7 is first opened as indicated by the arrow A in FIG. 3, and then a pharmaceutical cartridge 9 is inserted through an insertion opening 8 provided to the upper face of the cartridge holder 7 as shown by the arrow B, after which the cartridge holder 7 is closed as shown in FIG. 2, whereupon the pharmaceutical cartridge 9 is mounted inside the main body case 1 as shown in FIG. 4.

FIG. 5a shows the configuration near the insertion opening 8 of the cartridge holder 7, and is a detail view of the Q part in FIG. 4. FIG. 5b shows the configuration near a home point sensor 23, and is a detail view of the P art in FIG. 4. FIGS. 4, 5a, and 5b show the state when a piston 10 is disposed at its home position (discussed below).

As shown in FIGS. 4, 5a, and 5b, the piston 10 is provided above the insertion opening 8 of the cartridge holder 7 inside the main body case 1, and this piston 10 is designed to be inserted into or pulled out of the pharmaceutical cartridge 9 through the insertion opening 8 of the cartridge holder 7 by a piston drive mechanism 101 having a screw 11, gear 12 and a motor 13. In FIG. 4, the arrow C indicates the direction in which the piston 10 is inserted into the pharmaceutical cartridge 9 mounted to the cartridge holder 7 (also referred to as downward or the forward direction), and the arrow D indicates the direction in which the piston 10 is pulled out of the pharmaceutical cartridge 9 mounted to the cartridge holder 7 (also referred to as upward or the retraction direction).

Configuration of Cartridge Holder 7 and Nearby

The cartridge holder 7 will now be described in detail through reference to FIGS. 2 to 5.

As discussed above, the cartridge holder 7 is in the form of a cylinder having the insertion opening 8 in its upper face. An opening 14 is also provided to the lower face. The outer peripheral part of this opening 14 is threaded and serves as the injection needle mounting component 3 (see FIG. 4).

Also, an injection needle detector switch 15 is provided to this injection needle mounting component 3, and whether or not an injection needle 16 has been mounted to the injection needle mounting component 3 is detected by this injection needle detector switch 15 as in FIG. 6 (discussed below).

Furthermore, a shaft support 17 that supports the cartridge holder 7 so that it can open and close with respect to the main body case 1 is provided to the outer peripheral face at the bottom part of this cartridge holder 7.

Also, one end of an eject spring 18, which is used as an example of a biasing member, is linked on the opposite side (inside) of the shaft support 17 in the opening direction of the cartridge holder 7.

The other end of the eject spring 18 is linked to the main body case 1 at the top.

That is, as shown in FIG. 4, a holder-side linking component 71 that links to a first end 18a of the eject spring 18 is formed on the inside portion of the end of the cartridge holder 7 on the opening 14 side. Also, the eject spring 18 is disposed along the cartridge holder 7 on the inside of the cartridge holder 7 in a state in which the cartridge holder 7 is closed. A second end 18b of the eject spring 18 is linked to a main body-side linking component 111 formed on the main body case 1 on the insertion opening 8 side.

That is, when a force is exerted in the direction in which the eject spring 18 compresses, the insertion opening 8 portion at the top of the cartridge holder 7 is biased in the direction of opening with respect to the main body case 1.

Also, a latched component 19 is provided as shown in FIG. 5a to the upper part of the cartridge holder 7 in order to keep the cartridge holder 7 in its closed position as shown in FIGS. 2 and 4 against the biasing in the opening direction provided by the eject spring 18.

Furthermore, an ejector tab 20 that latches the latched component 19 is provided above the latched component 19 inside the main body case 1. This ejector tab 20 is adjacent and linked to a protrusion 22a on the lower end side of a slender lever 22. A spring 21 hits the opposite side of the protrusion 22a from the ejector tab 20, and the protrusion 22a and the ejector tab 20 are biased in the direction of the latched component 19 below (the insertion direction C) (see FIG. 5).

Also, the ejector tab 20 has on its inside a contact face 20a formed parallel to the movement direction of the piston 10, and the latched component 19 has on its outside a contact face 19a formed parallel to the movement direction of the piston 10 in a state in which the cartridge holder 7 is closed. When the contact face 20a and the contact face 19a come into contact, they maintain the cartridge holder 7 in its closed state.

Also, the ejector tab 20 has a sloped part 20b that slopes outward from the lower end of the contact face 20a. The latched component 19 has a sloped part 19b that slopes inward from the upper end of the contact face 19a. When the cartridge holder 7 is closed, the sloped part 20b slides with respect to the sloped part 19b, which affords smooth closure.

Also, as shown in FIGS. 4 and 5b, the lever 22 to which the ejector tab 20 is linked has a protrusion 22b disposed diagonally across from the protrusion 22a at the upper end of the lever 22 (a location where the protrusion direction is reversed), and is provided on a feed screw 11 side of the piston 10.

Specifically, as shown in FIG. 4, the slender lever 22 is disposed along the movement direction of the piston 10, to the inside of the piston 10 when the piston 10 has not been inserted into the pharmaceutical cartridge 9. The protrusion 22a and the ejector tab 20 are provided on the cartridge holder 7 side of the lever 22, and the protrusion 22b is provided on a gear 12 side of the lever 22. Thus, the lever 22 links the protrusion 22b and the ejector tab 20, and the lever 22, the protrusion 22b, and the ejector tab 20 are biased downward by the spring 21 so as to latch the latched component 19.

Configuration of Home Point Sensor 23 and Nearby

As shown in FIG. 5b, the home point sensor 23, which senses the home position of the piston 10, is provided on the rear end side of the piston 10 (the upper end side in FIG. 2). The home point sensor 23 is fixed on the inside of the main body case 1. A transmitting type of photoelectric sensor can be used as the home point sensor 23, for example, and the home position of the piston 10 can be sensed when a protrusion 10a provided to the piston 10 blocks out the light.

A protrusion 10b that protrudes to the lever 22 side is provided to the piston 10. The protrusion 10b provided on the rear end part of the piston 10 is lower than the protrusion 22b of the lever 22 (on the insertion direction C side), hits the protrusion 22b only when the piston 10 retracts above the home position (when it moves in the pull-out direction D), and moves the entire lever 22 backward (upward in FIGS. 2 and 3) along with it.

Meanwhile, during pharmaceutical injection (the state in FIGS. 6 and 7), when the piston 10 moves downward (that is, moves below the home position), the protrusion 22b on the upper end side of the lever 22 moves downward along with the protrusion 10b provided to the rear end part of the piston 10, but the lever 22 stops at the position indicated in FIGS. 6 and 7 (lower end position), and does not descend beyond that.

Therefore, the protrusion 22b on the upper end side of the lever 22 moves away from the protrusion 10a of the piston 10. This structure that prevents further descent can be, for example, a configuration in which the lever 22, the protrusion 22b, and the ejector tab 20 hit a protrusion (not shown) and stop upon reaching the position shown in FIG. 4. The position beyond which the ejector tab 20 does not descend is indicated by the dotted line in FIG. 9 (discussed below).

Thus, the latched component 19 provided inside the main body case 1 engages with the ejector tab 20 adjacent to the protrusion 22a on the lower end side of the lever 22, which maintains the cartridge holder 7 in its closed state.

Specifically, the ejector tab 20 attached to the protrusion 22a on the lower end side of the lever 22 returns to its home position after the piston 10 has completed injecting all of the pharmaceutical in the pharmaceutical cartridge, and if the piston 10 moves further upward after this, only then is the latched component 19 inside the main body case 1 disengaged, putting the cartridge holder 7 in an open state.

In the above example, the ejector tab 20 and the lever 22 are separate components that are linked, but this is not the only option, and they may instead be formed integrally.

Operation During Pharmaceutical Administration

Figure 6:
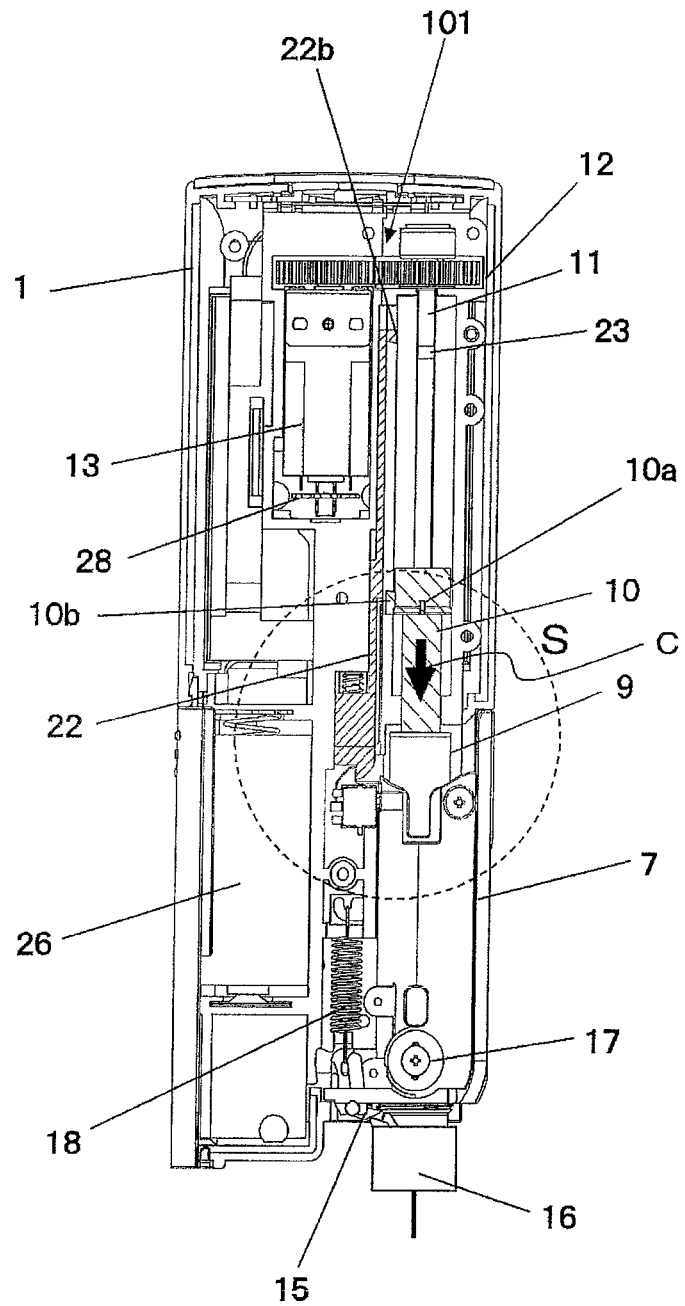
FIG. 6 is a front cross section of the internal configuration of the pharmaceutical injection device shown in FIG. 2.

FIG. 6 shows the state during pharmaceutical administration with the pharmaceutical injection device in this embodiment. FIG. 7 is a detail view of the S part in FIG. 6.

Figure 5:
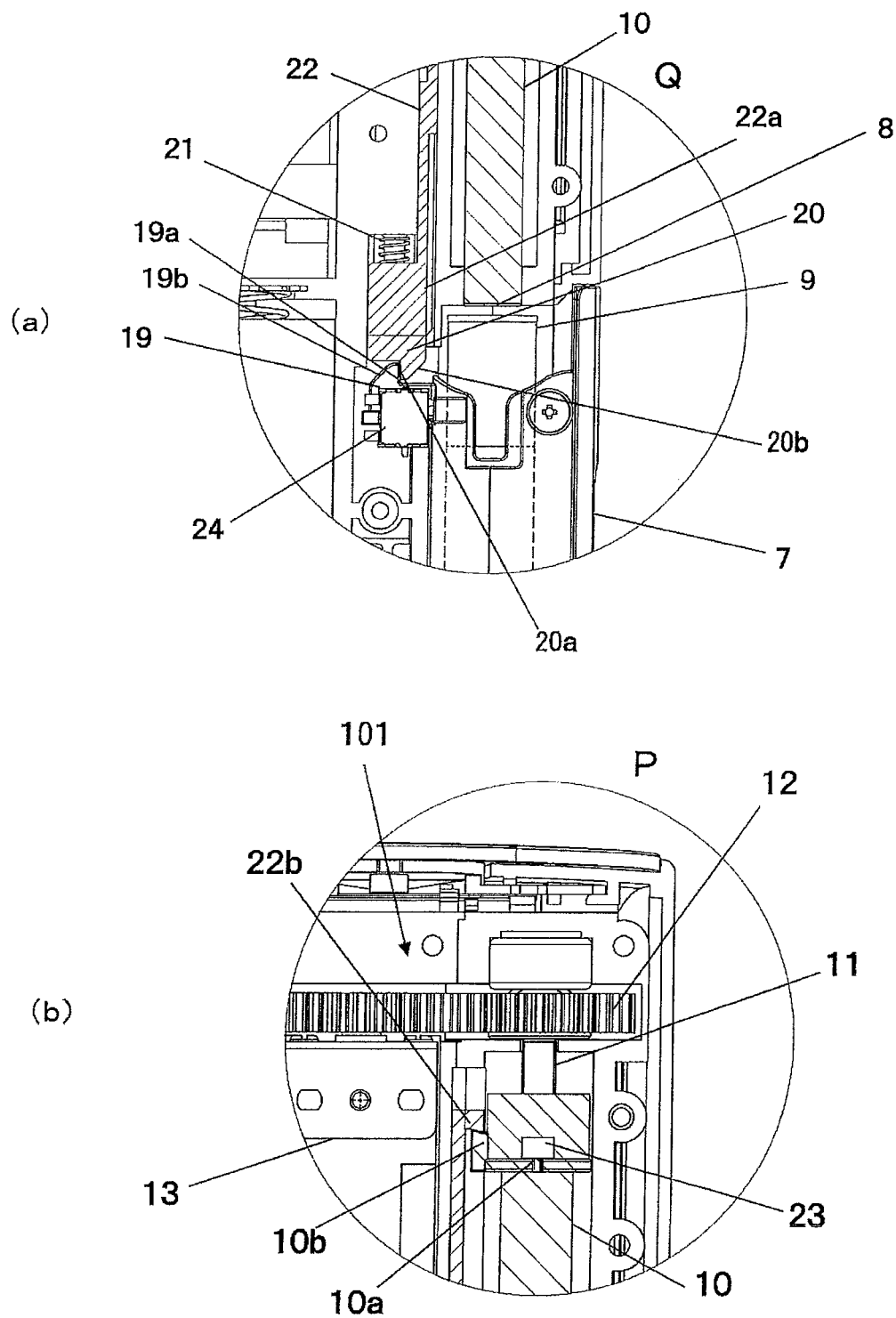
FIG. 5a is a detail view of the Q part in FIG. 4.
FIG. 5b is a detail view of the P part in FIG. 4.
Figure 7:
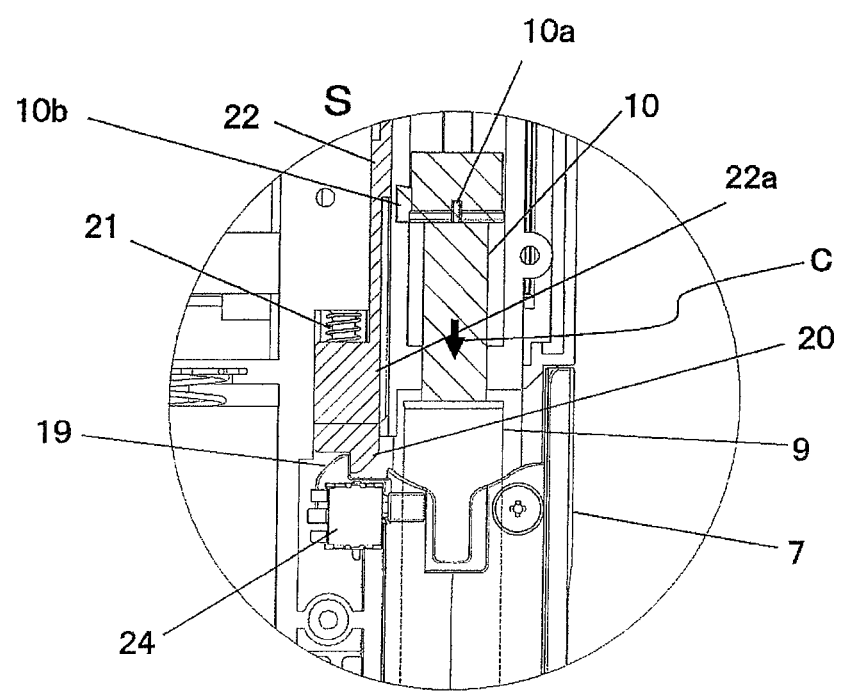
FIG. 7 is a detail view of the S part in FIG. 6.

The above-mentioned FIGS. 4 and 5 showed the initial state of the pharmaceutical injection device (the state when the piston 10 is in its home position), but FIGS. 6 and 7 show the operation of injecting the pharmaceutical (at the start of the injection operation).

Specifically, the injection of the pharmaceutical inside the pharmaceutical cartridge 9 is commenced by pressing the pharmaceutical injection switch 4 (see FIG. 3) provided to the outer peripheral surface of the main body case 1.

More specifically, the motor 13 of the piston drive mechanism 101 is actuated, the gear 12 linked to the motor 13 rotates, and this rotation of the gear 12 turns the feed screw 11, converting to the linear motion of the piston 10.

When the piston 10 moves downward, the distal end of the piston 10 hits a gasket (not shown) at the rear end of the pharmaceutical cartridge (see FIG. 7), and when the piston 10 is then moved after this, the pharmaceutical inside the pharmaceutical cartridge 9 goes through the injection needle 16 mounted to the tip of the pharmaceutical cartridge 9 and is injected under the skin.

Operation During Ejection of Cartridge Holder 7

Figure 8:
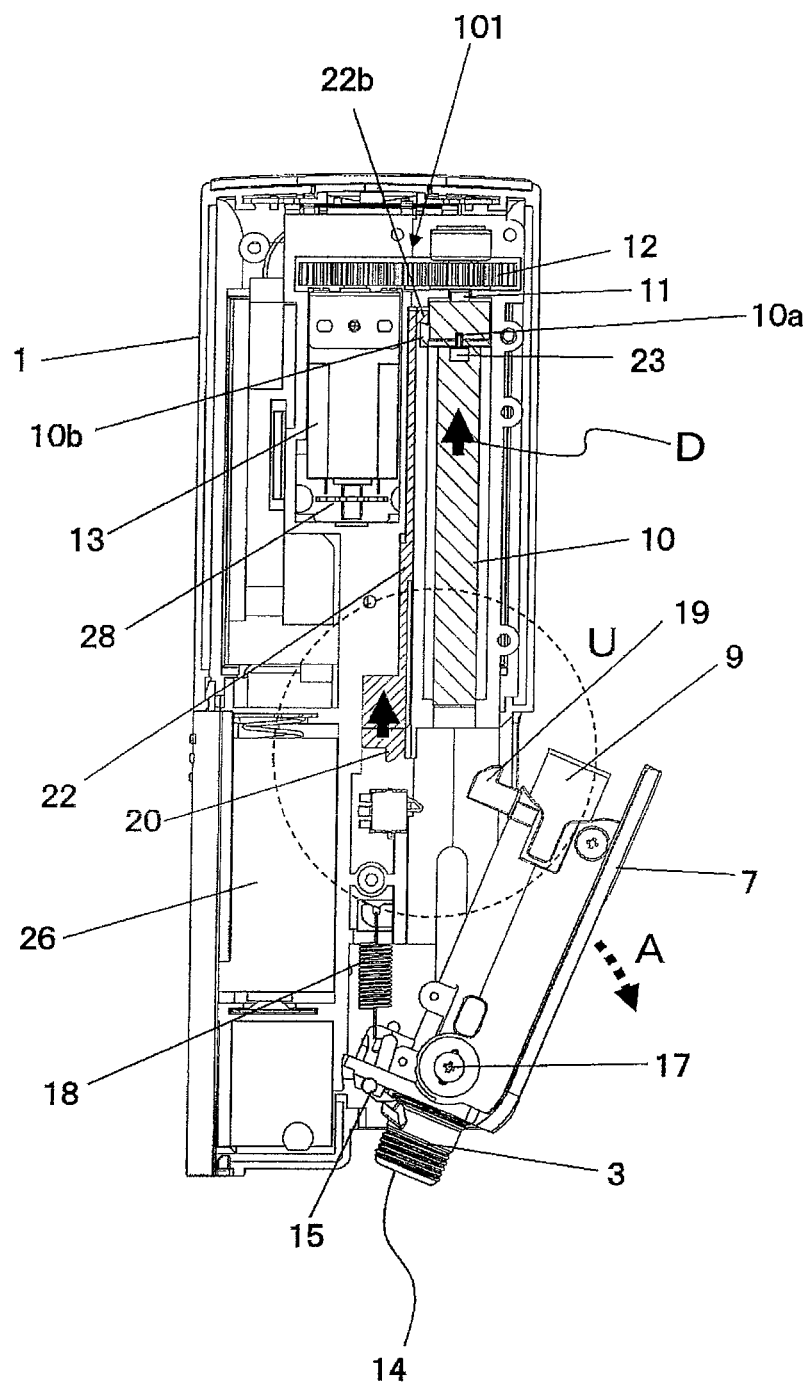
FIG. 8 is a front cross section of the internal configuration of the pharmaceutical injection device shown in FIG. 2.
Figure 9:
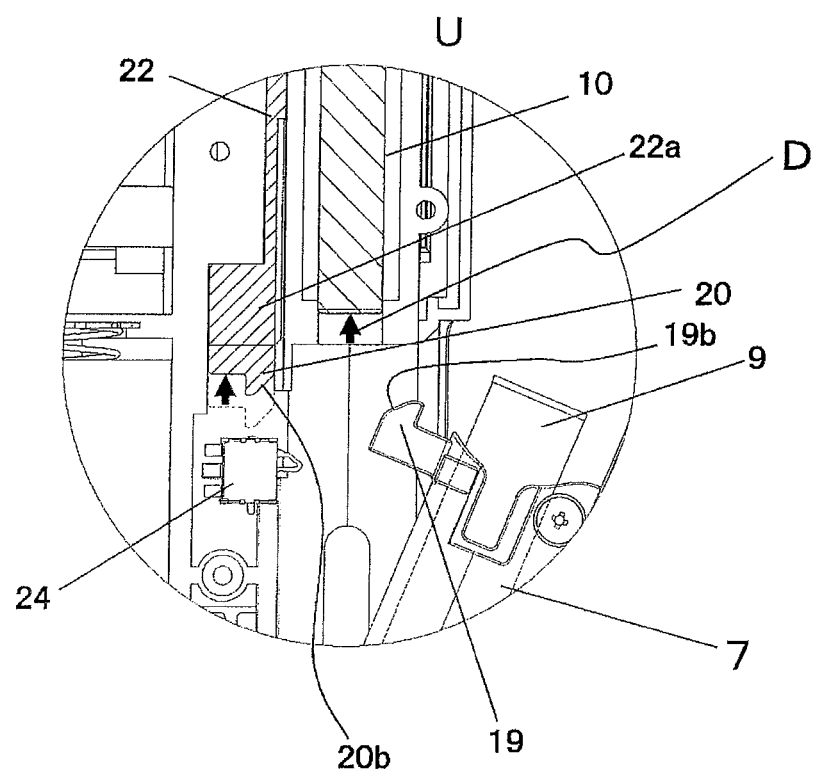
FIG. 9 is a detail view of the U part in FIG. 8.

The operation during ejection of the cartridge holder 7 will now be described through reference to FIGS. 8 and 9. FIG. 8 shows the state during the ejection of the cartridge holder 7 of the pharmaceutical injection device in this embodiment. FIG. 9 is a detail view of the U part in FIG. 8.

When the pharmaceutical injection operation described through FIGS. 6 and 7 above is completed and there is no more pharmaceutical in the pharmaceutical cartridge 9, the cartridge holder 7 has to be opened up to replace the pharmaceutical cartridge 9.

More specifically, in FIG. 6, when the piston 10 moves the gasket of the pharmaceutical cartridge 9 to the distal end, and all of the pharmaceutical in the pharmaceutical cartridge 9 has been injected, the piston 10 is retracted to its home position by the piston drive mechanism 101.

After this, the pharmaceutical cartridge 9 needs to be replaced, so the piston 10 is moved above its home position as shown in FIGS. 8 and 9 (see FIG. 5b).

At this point, the protrusion 10b at the upper end part of the piston 10 and the protrusion 22b of the lever 22 come into contact, so the lever 22 moves upward at the same time.

Also, the ejector tab 20 attached to the lower end of the lever 22 is moved upward at the same time while compressing the spring 21 that is biasing it, and this operation disengages the ejector tab 20 from the latched component 19.

At this point, the cartridge holder 7 is opened outward from the main body case 1 by the biasing force of the eject spring 18, with the shaft support 17 serving as a fulcrum.

Here, whether or not the cartridge holder 7 has been opened can be detected by an opening and closing detector switch 24 provided near the ejector tab 20 (see FIG. 5a, etc.).

Before this eject operation is performed, the injection needle 16 mounted to the injection needle mounting component 3 needs to be removed for the sake of safety, so a display prompting the removal of the injection needle 16 is given on the display component 5 provided to the front face of the main body case 1.

Also, the removal of the injection needle 16 can be detected by the injection needle detector switch 15.

Operation When Cartridge Holder 7 is Closed

Figure 10:
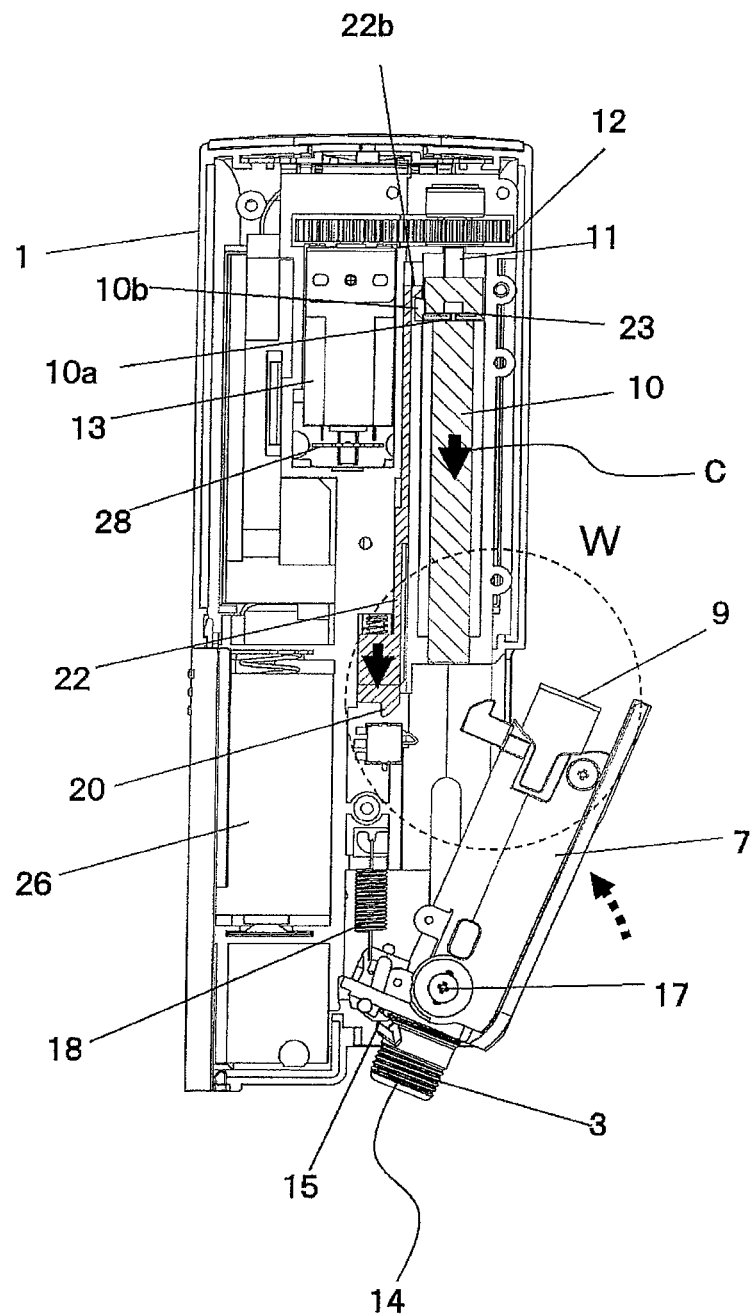
FIG. 10 is a front cross section of the internal configuration of the pharmaceutical injection device shown in FIG. 2.
Figure 11:
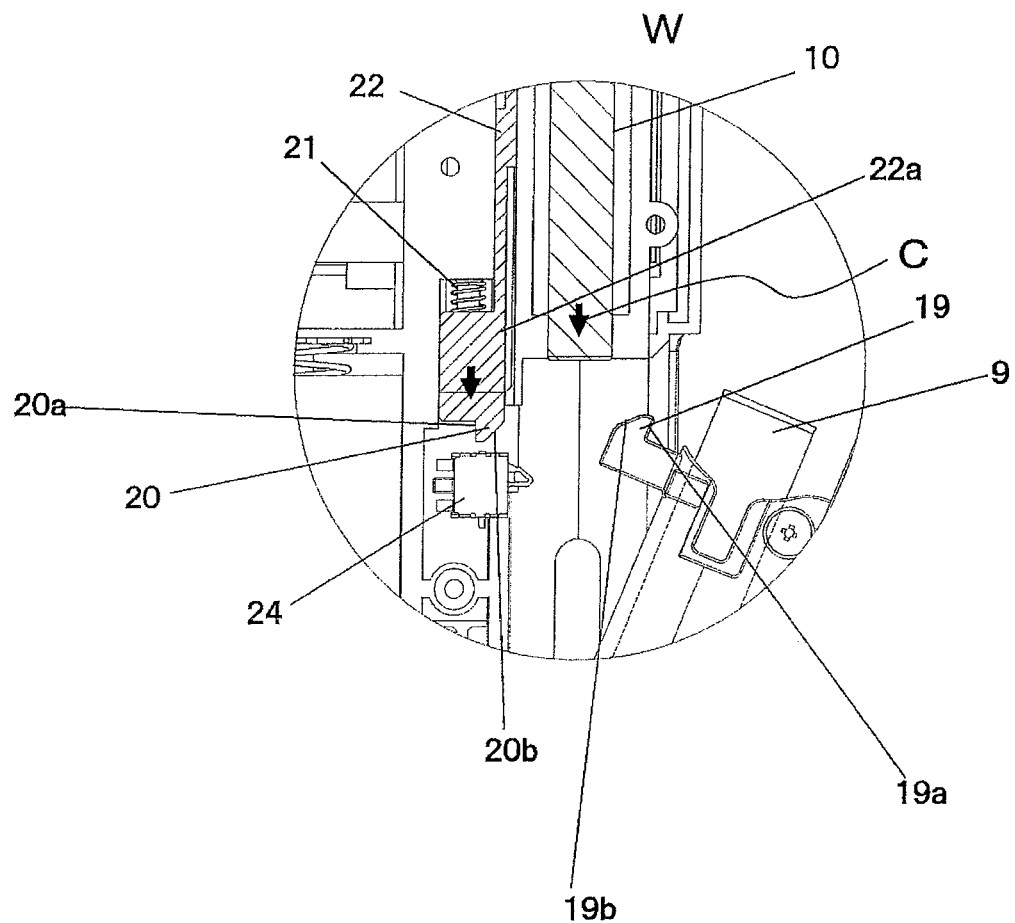
FIG. 11 is a detail view of the W part in FIG. 10.

FIG. 10 is a cross section of the pharmaceutical injection device when the cartridge holder 7 is closed. FIG. 11 is a detail view of the W part in FIG. 10.

FIGS. 10 and 11 show the state when the piston 10 has been moved to its home position after the ejection operation described through FIGS. 8 and 9 above.

At this point, as the piston 10 goes back to its home position, the lever 22 and the ejector tab 20 also descend, returning to the initial state (see FIG. 4) at the home position of the piston 10.

However, since the cartridge holder 7 at this point is still open, the latched component 19 and the ejector tab 20 are not engaged.

After this, the pharmaceutical cartridge 9 is replaced, and when the cartridge holder 7 is moved so that it closes to the main body case 1 side, the sloped part 19b of the latched component 19 rides up over the sloped part 20b of the ejector tab 20 as shown in FIG. 10, finally the latched component 19 and the ejector tab 20 engage, and this state is maintained.

In other words, that cartridge holder 7 that has returned to its initial state and that houses the replaced pharmaceutical cartridge 9 is held within the main body case 1.

Control Configuration

Figure 12:
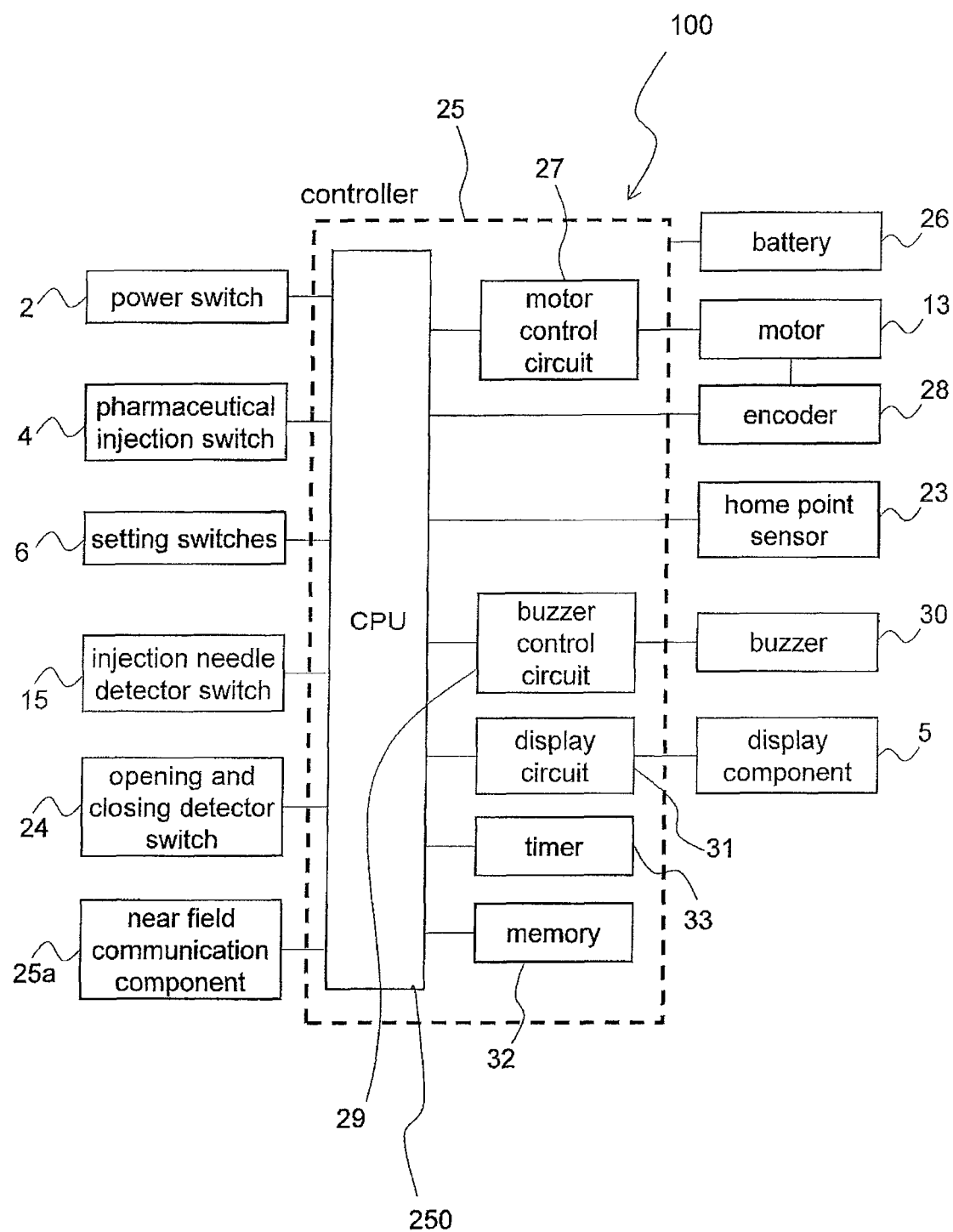
FIG. 12 is a control block diagram of the pharmaceutical injection device shown in FIG. 2.

FIG. 12 is a block diagram of the electrical circuit in the main body case 1 of the pharmaceutical injection device 100, and the surrounding area. A controller 25 has a CPU 250, is connected to various I/O interfaces and drive systems, and performs control over these.

More specifically, in terms of interface components, the CPU 250 of the controller 25 is connected to the power switch 2, the pharmaceutical injection switch 4, the setting switches 6, etc., and checks the input of the various control switches.

In terms of state detection, the CPU 250 of the controller 25 is also connected to the injection needle detector switch 15, which detects the mounting state of the injection needle 16, the opening and closing detector switch 24, which detects whether the cartridge holder 7 is open or closed, and so forth.

In terms of the drive system for the piston 10, the motor 13 that drives the piston 10 is connected to the CPU 250 inside the controller 25 via a dedicated motor control circuit 27 that controls this motor. Also, an encoder 28 that detects position information about the piston 10 is connected to the motor 13, and outputs pulses to the CPU 250 according to the rotation of the motor 13. The CPU 250 counts the pulses outputted by the encoder 28, and thereby calculates the amount of movement of the piston 10. Furthermore, the home point sensor 23, which senses the home position of the piston 10, is connected to the CPU 250, and the CPU 250 recognizes the current piston position by using the output of the encoder 28 and the output of the home point sensor 23. A memory 32 is connected to the CPU 250, and the recognized current piston position is stored as piston position information. This piston position information is a positive or negative numerical value, and when the piston position information is zero, it means that the piston is in its home position. When the piston position information is positive, it means that the piston is below the home position. Conversely, when the piston position information is negative, it means that the piston is above the home position. The absolute value of the piston position information indicates the distance the piston has moved from its home position.

More specifically, when the trailing edge of the protrusion 10a provided to the piston 10 crosses the home point sensor 23, it is concluded that the piston is in its home position, and the CPU 250 resets the piston position information stored in the memory 32 to zero. The CPU 250 then updates the value by adding or subtracting one to the piston position information according to the drive direction of the motor 13 every time the encoder 28 connected to the motor 13 outputs one pulse. In this way, the CPU 250 can always recognize the current piston position by using the piston position information stored in the memory 32. The memory 32 here is constituted by an EEPROM or another such nonvolatile memory, and the piston position information stored in the memory 32 is preserved when the power to the device is shut off. This piston position information is always reset to zero when the trailing edge of the protrusion 10a provided to the piston 10 crosses the home point sensor 23. That is, the home point sensor 23 is used to correct the piston position. The CPU 250 monitors the output of the home point sensor 23, and since it is possible that some kind of malfunction has occurred in the operation of the device when the error with respect to zero in the piston position information stored in the memory 32 upon detecting that the home point sensor 23 is in its home position has exceeded a specific threshold, processing is performed to display a warning on the display component 5 and halt operation, etc.

In addition, a buzzer 30 that alerts the user when an error occurs is connected to the CPU 250 via a buzzer control circuit 29 that controls the buzzer 30, inside the controller 25. The display component 5, which displays various messages, numerical values, and so forth, is connected to the CPU 250 via a dedicated display circuit 31 that controls the display component 5, inside the controller 25. The display component 5 is constituted by an LCD panel or the like.

Furthermore, the memory 32, which stores dosages, administration data, and so forth, and a timer 33, which measures the elapsed time, are installed in the controller 25 and connected to the CPU 250. A battery 26, which is the power supply for the device, is also installed and connected to the controller 25. Also, the pharmaceutical injection device 100 in this embodiment is provided with a near field communication component 25a that can communicate with the portable terminal 300, and the near field communication component 25a is connected to the controller 25. This near field communication component 25a will be discussed in detail below.

Operation of Ejector Mechanism of Pharmaceutical Injection Device

The operation of the ejector mechanism will now be described through reference to the flowchart in FIG. 13.

Figure 13:
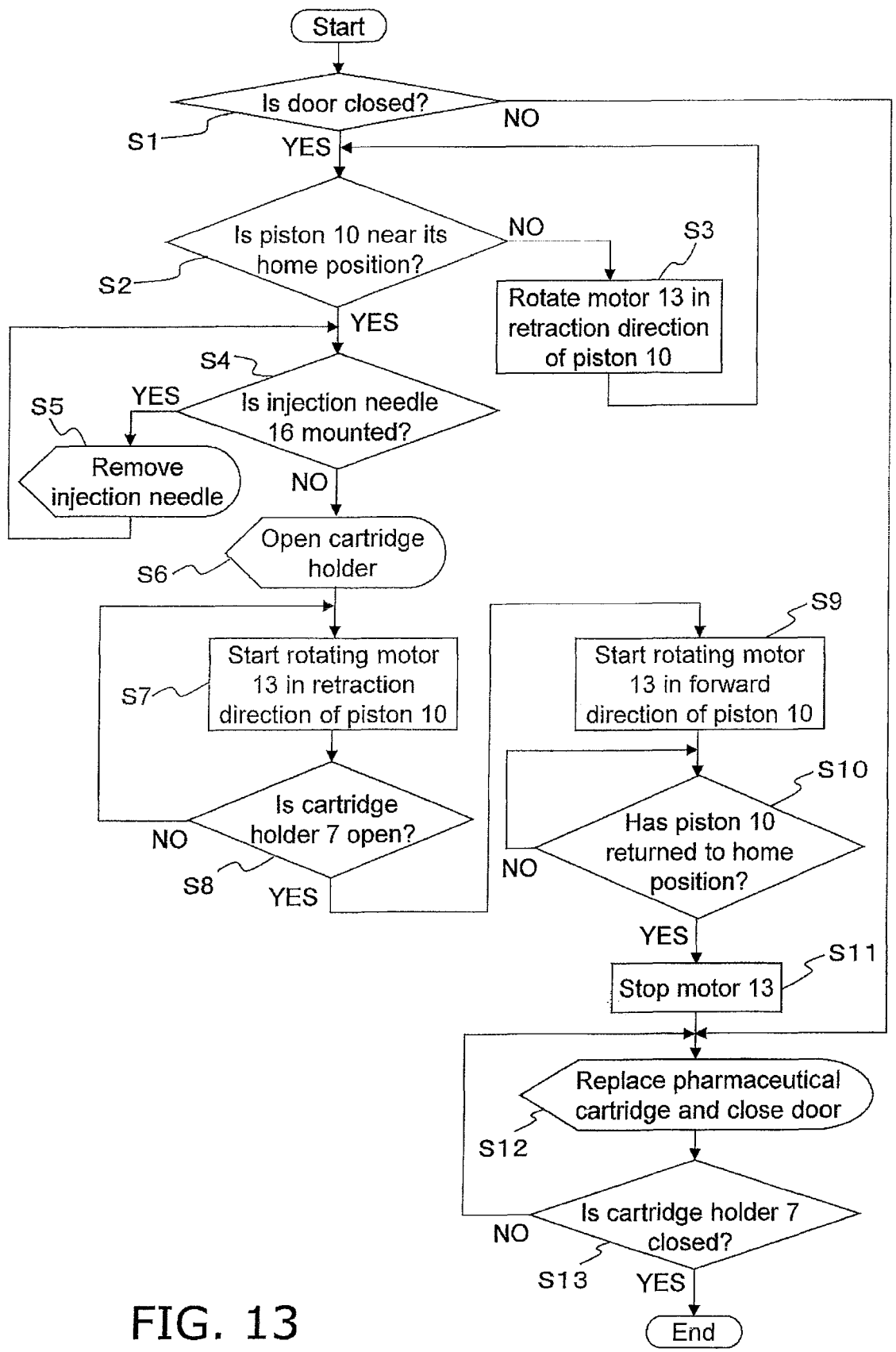
FIG. 13 is a flowchart of the operation of the pharmaceutical injection device shown in FIG. 2.

FIG. 13 assumes a timing at which it has become necessary to eject (open up) the cartridge holder 7, but examples of the timing of this ejection include when all of the pharmaceutical in the above-mentioned pharmaceutical cartridge 9 has been completely injected, and when it becomes necessary to replace an expired pharmaceutical.

The latter case, when it is necessary to replace an expired pharmaceutical, is, for example, a case in which a specific length of time (five weeks in this case) has elapsed since a pharmaceutical cartridge 9 whose expiration date is determined to be five weeks from the start of use was installed in the pharmaceutical injection device.

In this case, if the timer 33 is started at the point when the pharmaceutical cartridge 9 is replaced, and the time on the timer 33 has gone past the specified time, a period overrun error is determined, and control is performed to replace the pharmaceutical cartridge 9.

The point when the timer 33 is started here may, for example, be at the point when the pharmaceutical cartridge 9 has been replaced and the opening and closing detector switch 24 has detected that the cartridge holder 7 is closed, or at the point when the pharmaceutical in the pharmaceutical cartridge 9 is administered for the first time (the start of pharmaceutical administration).

The condition for needing to replace the pharmaceutical cartridge 9 can be when the pharmaceutical in the pharmaceutical cartridge 9 runs out, when the pharmaceutical has expired, etc.

As shown in FIG. 13, if it is necessary to replace the pharmaceutical cartridge 9, the controller 25 uses the opening and closing detector switch 24 to detect whether or not the cartridge holder 7 is closed (S1 in FIG. 13).

At this point, if the cartridge holder 7 is open, a display prompting the user to replace the pharmaceutical cartridge 9 and close the cartridge holder 7 is displayed on the LCD panel that is the display component 5 (S12 in FIG. 13).

On the other hand, if the cartridge holder 7 is closed, the controller 25 uses the home point sensor 23 to confirm whether or not the piston 10 has returned to near its home position (S2 in FIG. 13).

At this point the home point sensor 23 determines that the piston 10 is near its home position if the protrusion 10a is within the detection range of the home point sensor 23. The detection range here encompasses not only when the trailing edge of the protrusion 10a has crossed the home point sensor 23, but also when the protrusion 10a has crossed the home point sensor 23 from above, that is, when the leading edge of the protrusion 10a has crossed the home point sensor 23.

If the piston 10 has not returned to its home position, the controller 25 actuates the motor control circuit 27, rotates the motor 13, and moves the piston 10 in the retraction direction (the pull-out direction D) (S3 in FIG. 13).

When the rotation of the motor 13 in S3 has caused the trailing edge of the protrusion 10a to cross the home point sensor 23, the piston 10 is assumed to have returned to its home position, and there is a transition from S2 to S4. The motor 13 is stopped at this point.

If the home point sensor 23 in S2 has confirmed that the piston 10 is near its home position, or in S3 that the piston 10 has returned to its home position, the controller 25 uses the injection needle detector switch 15 to confirm whether or not the injection needle 16 is mounted (S4 in FIG. 13).

If the injection needle 16 is still mounted, the controller 25 causes the display component 5 to display a message prompting the user to remove the injection needle 16 (S5 in FIG. 13).

If the injection needle 16 has been removed, the controller 25 causes the display component 5 to display a message prompting the user to open the cartridge holder 7 (S6 in FIG. 13).

Next, the operation of actually opening up the cartridge holder 7 is performed (S7 in FIG. 13).

More specifically, the controller 25 commands the motor control circuit 27 to rotate the motor 13 and move the piston 10 further in the retraction direction (the pull-out direction D) from the home position.

Consequently, as shown in FIG. 5b, the protrusion 10b of the piston 10 comes into contact with the protrusion 22b of the lever 22, and the entire slender lever 22 moves upward. Along with this, the ejector tab 20 that is adjacent and attached to the lower side of the lever 22 also retracts upward, moving away from the latched component 19 provided to the main body case 1, and disengaging.

When the latched component 19 is disengaged from the ejector tab 20, as shown in FIGS. 8 and 9, the biasing force of the eject spring 18 causes the cartridge holder 7 to open outward, with the shaft support 17 serving as the fulcrum.

The controller 25 uses the opening and closing detector switch 24 to confirm whether or not the cartridge holder 7 has been opened (S8 in FIG. 13).

If the cartridge holder 7 has not been opened, the flow returns to S7 in FIG. 13, and the retraction of the piston 10 is continued.

Next, if the cartridge holder 7 is open, the controller 25 again advances the piston 10 in the insertion direction C via the motor control circuit 27, the motor 13, the gear 12, the feed screw 11, etc., moving it to the home position (S9 in FIG. 13).

The controller 25 then uses the home point sensor 23 to detect or confirm whether or not the piston 10 has returned to its home position (S10 in FIG. 13), and if it has not returned to the home position, the control goes back to S9 in FIG. 13, and the advance of the piston 10 is continued.

If the piston 10 has returned to its home position, the controller 25 causes the motor control circuit 27 to stop the motor 13, thus stopping the piston 10 (S11 in FIG. 13).

Next, the controller 25 causes the display component 5 to display a message prompting the user to replace the pharmaceutical cartridge 9 and to close the cartridge holder 7 after this replacement (S12 in FIG. 13).

The pharmaceutical cartridge 9 is then replaced, and the opening and closing detector switch 24 then detects whether or not the cartridge holder 7 has been closed (S13 in FIG. 13).

If the cartridge holder 7 is still open, the control goes back to S12, and the controller 25 waits for it to be closed.

If it is confirmed that the cartridge holder 7 is closed, the procedure is ended. At this point the timer 33 (see FIG. 12) may be started.

Communication Component of Pharmaceutical Injection Amount

A feature of this embodiment is that with the pharmaceutical injection device 100, the pharmaceutical injection amount for a patient 200 can be set with the portable terminal 300 belonging to the patient 200.

More specifically, when the patient 200 or someone else uses the portable terminal 300 to input pharmaceutical injection amount change conditions, these pharmaceutical injection amount change conditions are transmitted over the network 400 to the health care worker-use information terminal 500, and when the health care worker changes the pharmaceutical injection amount, the injection amount change setting is transmitted through the portable terminal 300 to the pharmaceutical injection device 100.

To this end, with the pharmaceutical injection device 100, in addition to the above configuration, the near field communication component 25a is connected to the controller 25 as shown in FIG. 12.

This near field communication component 25a is provided inside the main body case 1.

Portable Terminal

Figure 14:
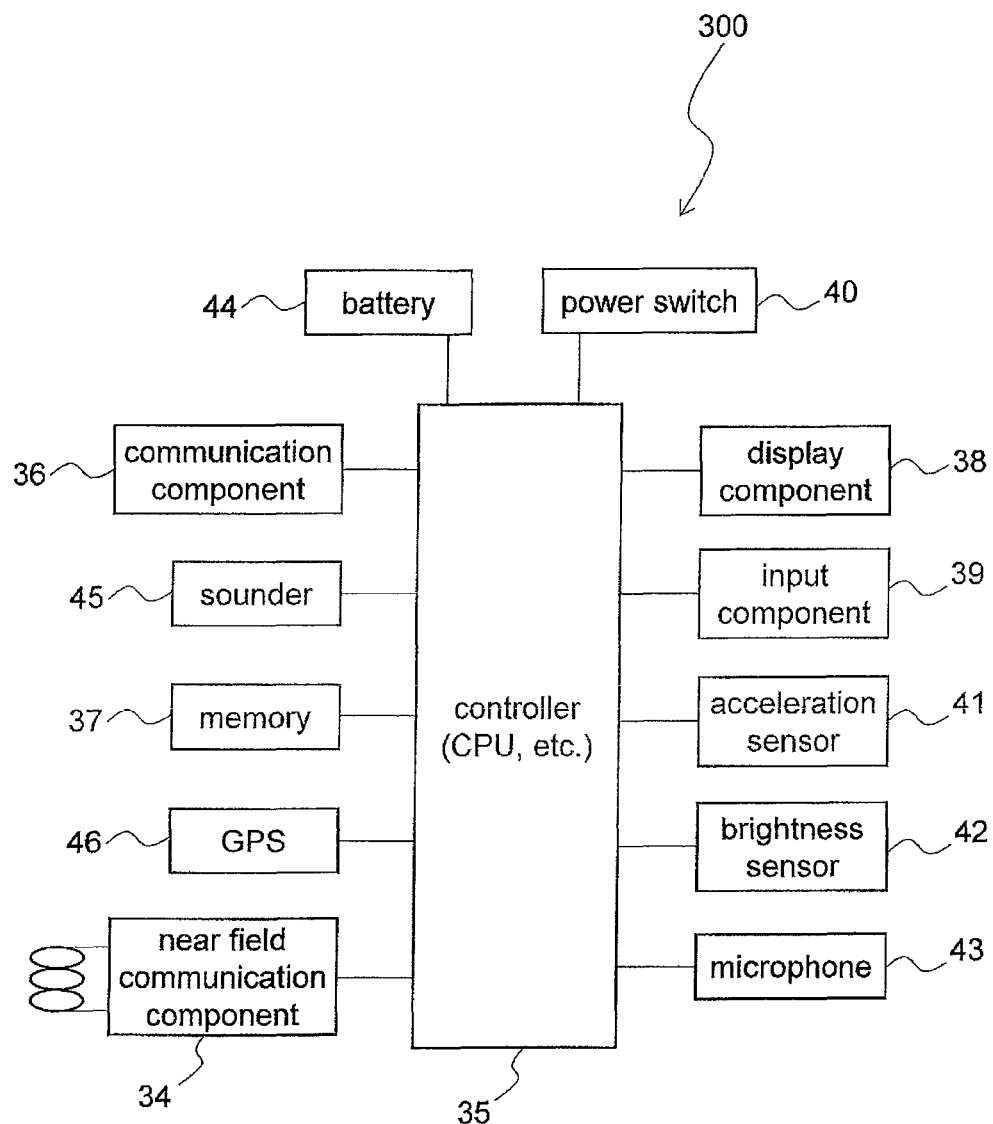
FIG. 14 is a control block diagram of the portable terminal used in the pharmaceutical injection system shown in FIG. 1.

FIG. 14 is a block diagram of the control configuration of the portable terminal 300 in this embodiment.

The portable terminal 300 shown in FIG. 1 is what is commonly called a cell phone, and has a near field communication component 34, a controller 35, a communication component 36, a memory 37, a display component 38, and an input component 39. The near field communication component 34 is able to communicate with the near field communication component 25a of the pharmaceutical injection device 100. The controller 35 is connected to the near field communication component 34. The communication component 36, the memory 37, the display component 38, and the input component 39 are connected to the controller 35. The input component 39 is constituted by a touch screen or the like.

Of these, because the near field communication component 34 makes use of NFC, the portable terminal 300 and the pharmaceutical injection device 100 can perform near field communication between the near field communication component 25a and the near field communication component 34.

This portable terminal 300 is also able to communicate with the health care worker-use information terminal 500 via the communication component 36 and the network 400.

This portable terminal 300 is also provided with a power switch 40, an acceleration sensor 41, a brightness sensor 42, a microphone 43, a buttery 44, a sounder 45, and a GPS 46. These are connected to the controller 35.

Health Care Worker-use Information Terminal

Figure 15:
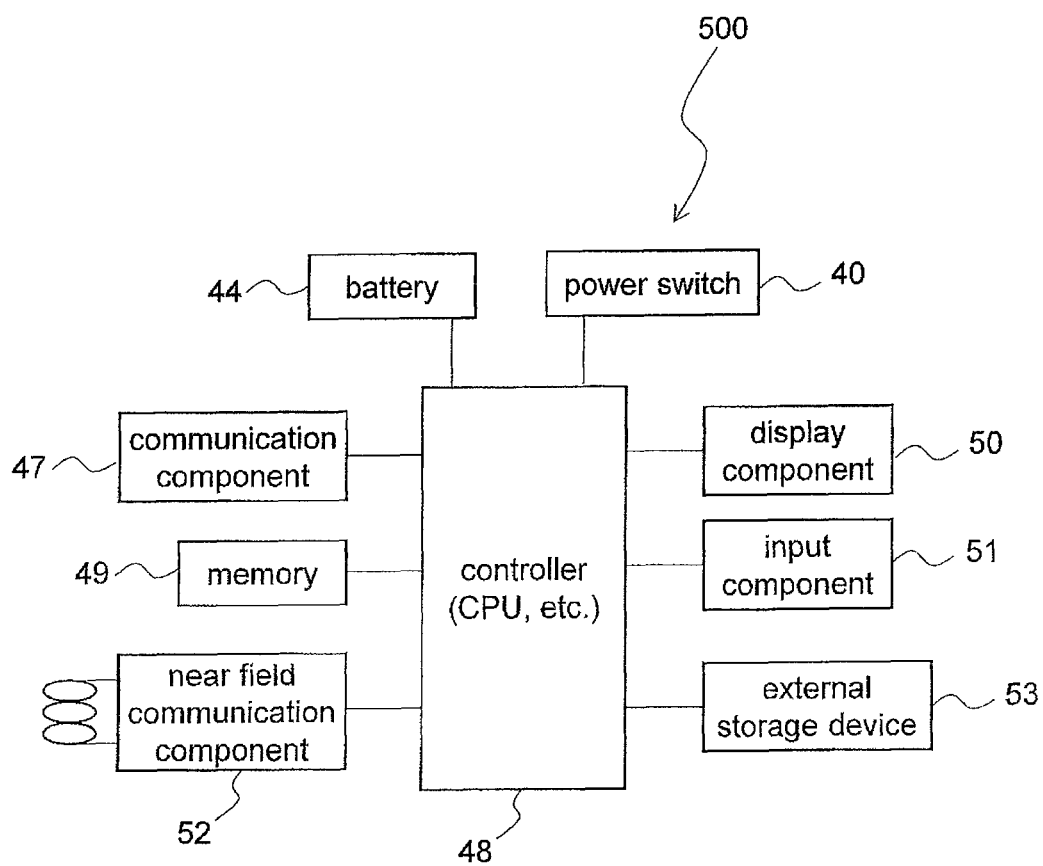
FIG. 15 is an oblique view showing a control block diagram of the health care worker-use information terminal used in the pharmaceutical injection system shown in FIG. 1.

FIG. 15 is a block diagram of the control configuration of the health care worker-use information terminal 500 in this embodiment.

As shown in FIG. 15, the health care worker-use information terminal 500, which can be connected to the portable terminal 300 over the network 400, has a communication component 47, a controller 48, a memory 49, a display component 50, and an input component 51. The communication component 47 is able to communicate with the communication component 36 of the portable terminal 300 over the network 400. The controller 48 is connected to the communication component 47. The memory 49, the display component 50, and the input component 51 are connected to the controller 48.

The health care worker-use information terminal 500 is also connected to a near field communication component 52 that can perform near field communication with the near field communication component 34 of the portable terminal 300, and an external storage device 53. The health care worker-use information terminal 500 is further provided with a battery 44, the power switch 40, etc.

The near field communication component 52 makes use of near field wireless communication (NFC)

2. Operation

Next, the operation of the pharmaceutical injection system in this embodiment will be described, and an example of how the pharmaceutical injection system of the present invention is controlled will also be discussed.

2-1 Input of Injection Amount Change Conditions

Figure 16A:
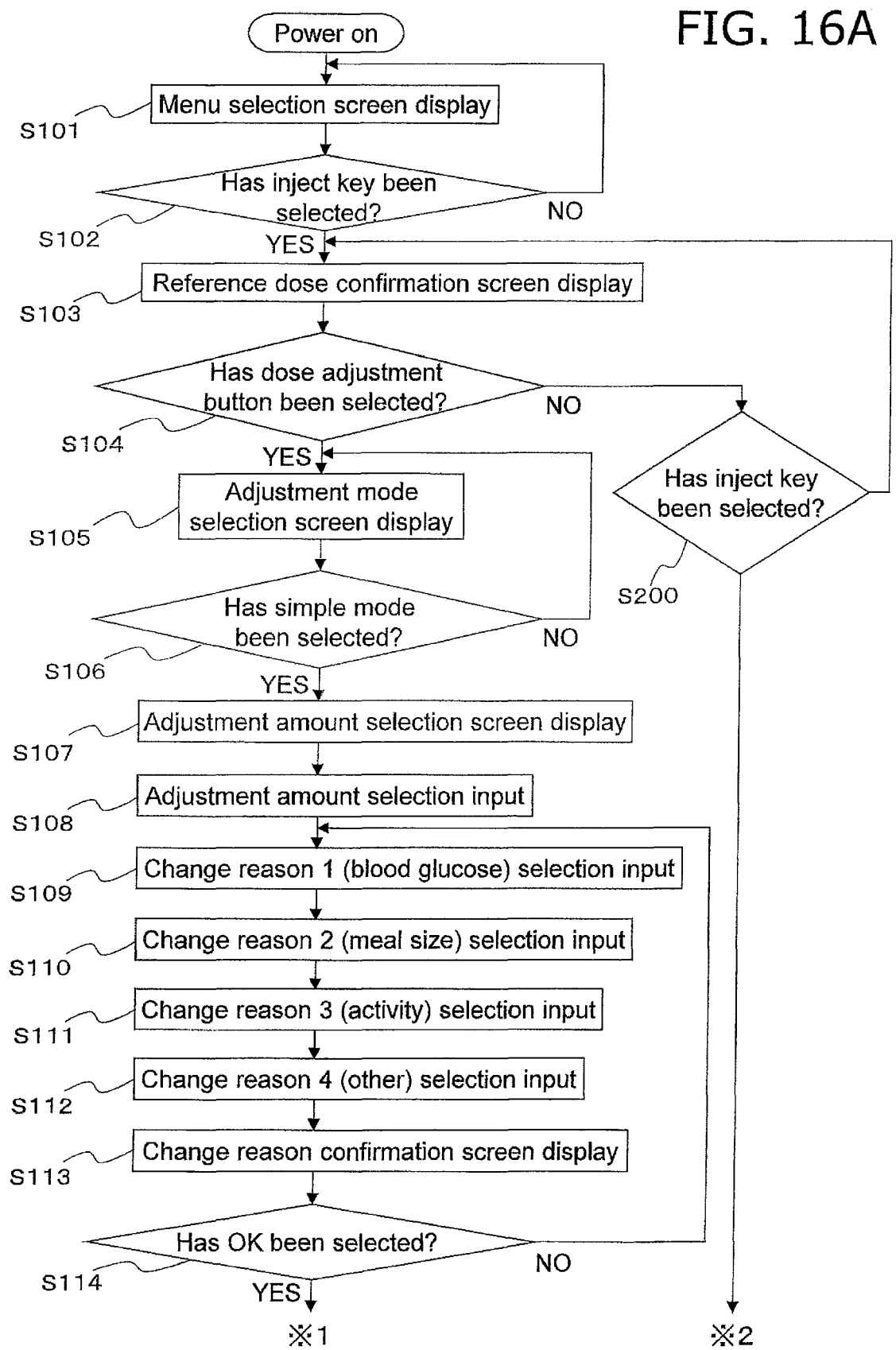
FIG. 16A is a flowchart of a method for controlling the portable terminal in the pharmaceutical injection system shown in FIG. 1.
Figure 16B:
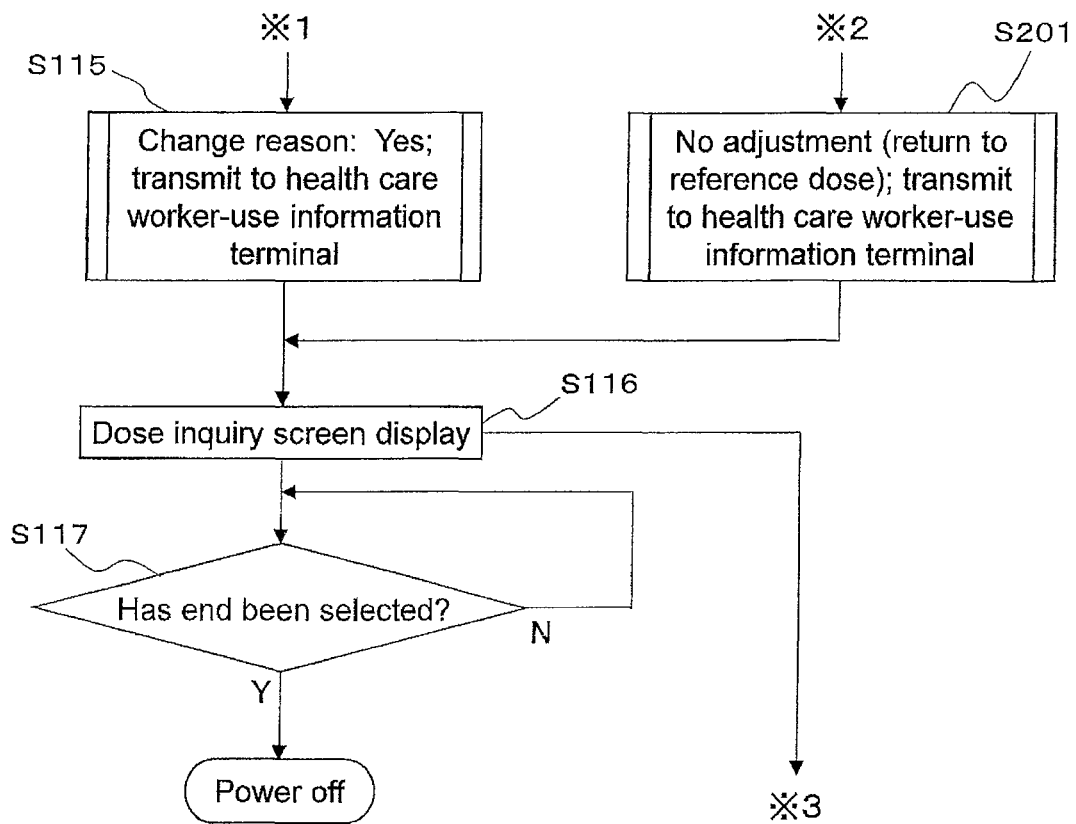
FIG. 16B is a flowchart of a method for controlling the portable terminal in the pharmaceutical injection system shown in FIG. 1.
Figure 16C:
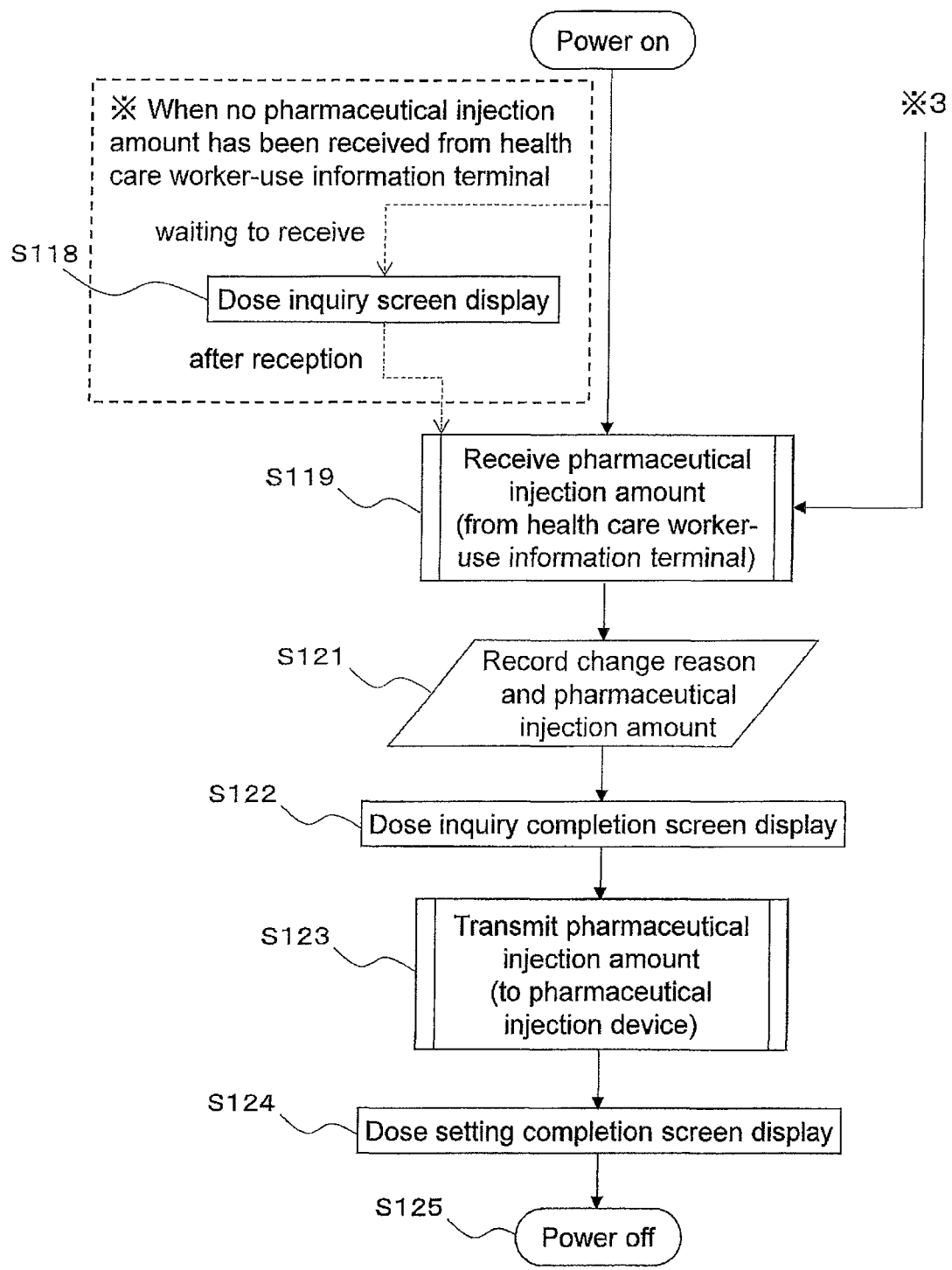
FIG. 16C is a flowchart of a method for controlling the portable terminal in the pharmaceutical injection system shown in FIG. 1.

FIGS. 16A to 16C are flowcharts of the operation involved in changing the pharmaceutical injection amount at the portable terminal 300. FIGS. 17A and 17B illustrate the operation involved in changing the pharmaceutical injection amount, and focus on the display component 38. The states of the display component 38 in FIGS. 17A and 17B are when the patient 200 inputs change conditions for changing the pharmaceutical injection amount. Also, the states of the display component 38 in FIGS. 17A and 17B are given the numbers from the steps S in FIGS. 16A to 16D, and show the states of the display component 38 in these steps S.

Specifically, when a pharmaceutical injection amount change program stored in the memory 37 is launched in a state in which the power switch 40 of the portable terminal 300 has been turned on, a pharmaceutical injection amount change conditions input screen is displayed on the display component 38 (S101 in FIG. 16A, and S101 in FIG. 17).

In view of this, in S102, when the user touches an inject key 601 appearing on the display component 38 (S101 in FIG. 16A), a reference injection amount set by a health care worker is initially displayed on the display component 38 (S103 in FIG. 16A, and S103 in FIG. 17).

Since an inject key 602 is also displayed on the display component 38 on the screen where the reference injection amount is displayed (S103 in FIG. 17), when this inject key 602 is touched, the health care worker confirms the pharmaceutical injection amount, after which the pharmaceutical injection device 100 is used to inject the pharmaceutical. This operation will be described below.

Meanwhile, in S103 in FIG. 17A, when an adjust key 603 for adjusting the dose displayed on the display component 38 is touched, an adjustment mode selection key is displayed on the display component 38 (S104 and S105 in FIG. 16A, and S105 in FIG. 17A). That is, if the pharmaceutical injection amount does not need to be adjusted, the above-mentioned inject key 602 is selected, but if adjustment is needed, the adjust key 603 is selected.

When a simple adjustment key 604 is touched, an increase key 605 and a decrease key 606 are displayed on the display component 38 (S106 and S107 in FIG. 16A, and S107 in FIG. 17A). Specifically, the increase key 605 is selected when the user wants to increase the pharmaceutical injection amount, and the decrease key 606 is selected when the user wants to decrease the pharmaceutical injection amount. The two states shown in S107 in FIG. 17A are when each of these keys has been selected, with the selected key being highlighted.

In S107 in FIG. 17A, when either the increase key 605 or the decrease key 606 is operated (S108 in FIG. 16A), a screen for inputting the reason that key was selected is then displayed on the display component 38 (S109 in FIG. 16A and S109 in FIG. 17A). Information related to the adjustment amount, regarding whether the increase key 605 or the decrease key 606 was operated, is transmitted to the health care worker-use information terminal 500 along with the change reason (discussed below) in S115 (discussed below). The reasons for changing the pharmaceutical injection amount are preset by a health care worker, and in this embodiment blood glucose level, meal size, amount of activity (also called amount of exercise), and scheduled administration date and time are set.

In this embodiment, first of all, a high key 607, a normal key 608, and a low key 609 are displayed on the display component 38 to select whether the blood glucose level measured the last time was high, normal, or low (S109 in FIG. 16A and S109 in FIG. 17A). An example of "high" here is when the average blood glucose level over the past two to three days is above 200 mg/dL, and is above 160 mg/dL before breakfast. An example of "normal" is when the average blood glucose level over the past two to three days is 80 to 200 mg/dL, and is 60 to 160 mg/dL before breakfast. An example of "low" is when the average blood glucose level over the past two to three days is below 80 mg/dL, and is below 60 mg/dL before breakfast. The level cutoffs are set so that they can be checked in "Help."

Next, a large key 610, a normal key 611, and a small key 612 are displayed on the display component 38 to select whether the meal size was large, normal, or small (S110 in FIG. 16A and S110 in FIG. 17A). Examples of the reason for this change include a patient whose intake energy is suppressed by dietetic therapy. An example of "large" is when the intake energy is above 1200 kcal/day and the carbohydrate count is above 500 g/day. An example of "normal" is when the intake energy is 600 to 1200 kcal/day and the carbohydrate count is 200 to 500 g/day. An example of "small" is when the intake energy is below 600 kcal/day and the carbohydrate count is below 200 g/day. The level cutoffs are set so that they can be checked in "Help."

Next, a low key 613, a normal key 614, and a high key 615 are displayed on the display component 38 to select whether the amount of activity was low, normal, or high (S111 in FIG. 16A and S111 in FIG. 17A). Examples of the reason for this change include a patient whose energy consumption in walking is guided by exercise therapy. An example of "high" is when the consumed energy is above 2000 kcal/day, the number of steps is above 10,000 per day, and the metabolic equivalents is above 5 per day. An example of "normal" is when the consumed energy is 1000 to 2000 kcal/day, the number of steps is 2000 to 10,000 per day, and the metabolic equivalents is 1 to 5 per day. An example of "low" is when the consumed energy is below 1000 kcal/day, the number of steps is below 2000 per day, and the metabolic equivalents is below 1 per day. The level cutoffs are set so that they can be checked in "Help."

Next, a late key 616, an on time key 617, and an early key 618 are displayed on the display component 38 to select whether the pharmaceutical administration time was late, on time, or early (S112 in FIG. 16A and S112 in FIG. 17A). Examples of the reason for this change include a patient for whom a change in the scheduled administration time is permitted. An example of "late" is when the user has forgotten to take an injection, that is, when it is done later than the scheduled time. An example of "early" is when the user wants to take an injection before going out, that is, when it is done earlier than the scheduled time. Another example of "early" is when the user wants to take an additional injection because the dose was too low the previous time. The level cutoffs are set so that they can be checked in "Help."

When these four conditions are inputted, an input confirmation screen is displayed on the display component 38 (S113 in FIG. 16A and S113 in FIG. 17A). On this input confirmation screen are displayed a display component 619 on which a change reason is displayed, an OK key 620, and an "Again" key 621 for setting the change reason again. If the user wishes to take an injection after confirmation, the above-mentioned OK key 620 is selected, and if the user wishes to redo a reason selection, the again key 621 is selected.

When the OK key 620 is operated, information related to the change reason (an example of pharmaceutical injection amount setting conditions) and the adjustment amount is transmitted to the health care worker-use information terminal 500 over the network 400 (S113, S114, and S115 in FIG. 16A, 16B and S113 in FIG. 17A).

When the change reason is transmitted, a screen indicating "under inquiry" is displayed on the display component 38 (S116 in FIG. 16B and S116 in FIG. 17A).

When an end key 622 is pressed on the under inquiry screen (S117 in FIG. 16B), the power is switched off.

2-2 Injection Amount Change

Figure 18A:
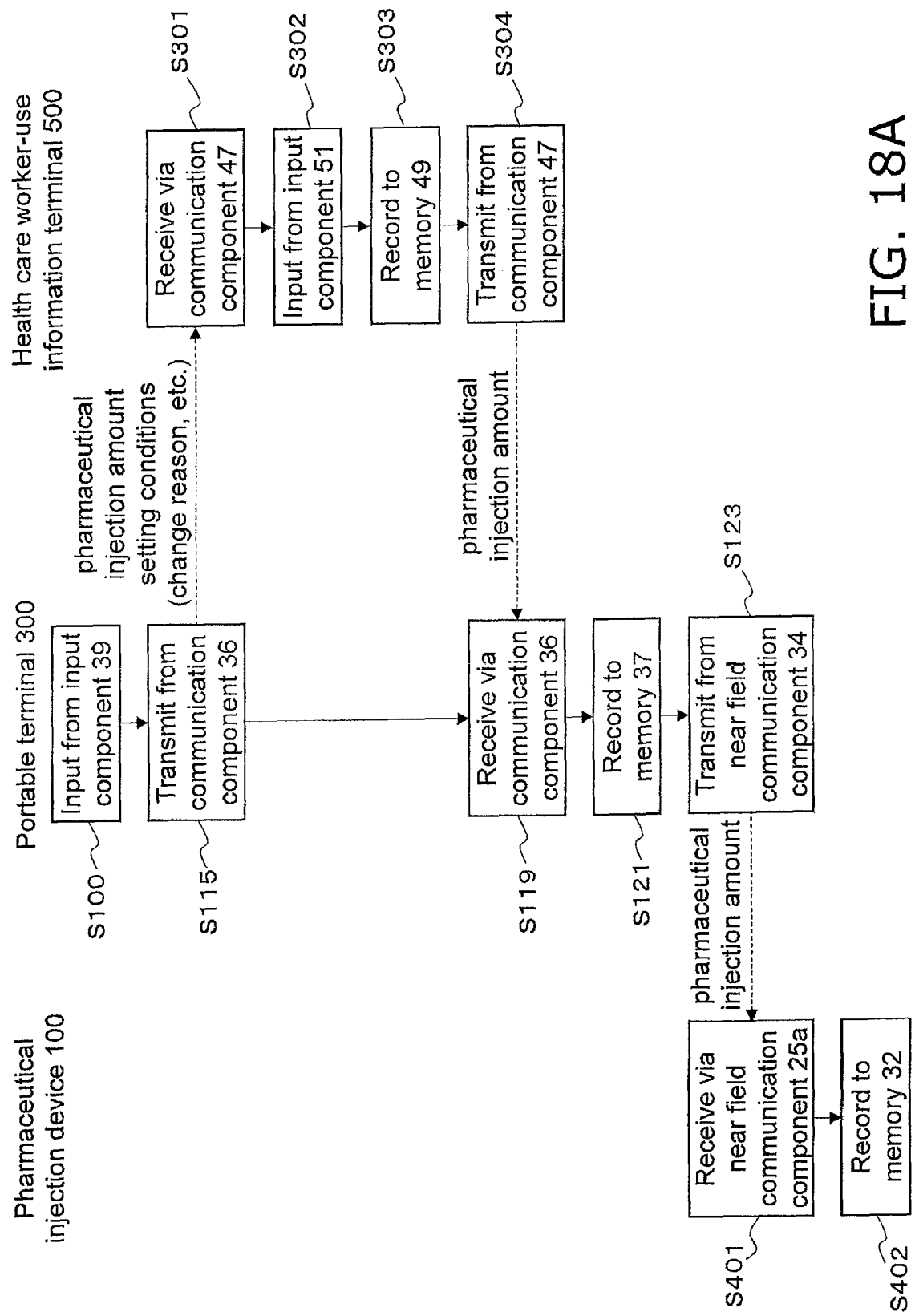
FIG. 18A is a flowchart of the control method in the pharmaceutical injection system shown in FIG. 1.

FIG. 18A is a flowchart of the method for controlling the pharmaceutical injection system in this embodiment. S100 in FIG. 18A, in which change conditions, etc., are inputted from the input component 39, indicates S101 to S114 in FIG. 16A.

As discussed above, information related to the change reason (an example of pharmaceutical injection amount setting conditions) and the adjustment amount is transmitted from the portable terminal 300 to the health care worker-use information terminal 500 (S115 in FIG. 16B and S115 in FIG. 18A).

The health care worker-use information terminal 500 can receive the change reason and information related to the adjustment amount via the communication component 47 (S301 in FIG. 18A). The health care worker then uses the health care worker-use information terminal 500 to input a change (increase or decrease) in the pharmaceutical injection amount from the input component 51 in a state in which the above are displayed on the display component 50 (S302 in FIG. 18A).

The pharmaceutical amount finally set by the health care worker, the name of the patient 200, and the date are then recorded in the memory 49 along with the conditions inputted by the patient 200 (such as the above-mentioned blood glucose level, meal size, amount of activity, and other information) (S303 in FIG. 18A).

Also, the pharmaceutical amount finally set by the health care worker (an example of the pharmaceutical injection amount), the name of the patient 200, and the date are also transmitted to the communication component 36 of the portable terminal 300 via the communication component 47 of the health care worker-use information terminal 500 along with the above-mentioned conditions (such as the above-mentioned blood glucose level, meal size, amount of activity, and other information) (S304 in FIG. 18A).

When information about the pharmaceutical injection amount is transmitted from the health care worker-use information terminal 500 in a state in which the under inquiry screen is being displayed, the portable terminal 300 receives the information about the pharmaceutical injection amount (S119 in FIG. 16C). This case (when the control proceeds from S116 to S119) is a case in which the portable terminal 300 receives information related to the pharmaceutical injection amount from the health care worker-use information terminal 500 right away after the physician 501 or other health care worker checks the change reason with the health care worker-use information terminal 500 and sets the dose.

On the other hand, if the power to the portable terminal 300 is temporarily turned off in S117 before the information about the pharmaceutical injection amount is received from the health care worker-use information terminal 500, and if the power to the portable terminal 300 is turned back on after the physician 501 has checked the change reason with the health care worker-use information terminal 500 and set the dose, the portable terminal 300 receives the information about the pharmaceutical injection amount (S119 in FIG. 16C).

Meanwhile, if information about the pharmaceutical injection amount has not been received from the health care worker-use information terminal 500 after the power to the portable terminal 300 is turned on the next time, a screen indicating that the dose is under inquiry is displayed on the display component 38 (S118 in FIG. 16C and S118 in FIG. 17B), and the portable terminal 300 waits to receive the pharmaceutical injection amount.

Once the portable terminal 300 receives the pharmaceutical injection amount (S119 in FIG. 16C), the controller 35 of the portable terminal 300 records the above-mentioned change reason (such as the above-mentioned blood glucose level, meal size, amount of activity, and other information) and the pharmaceutical amount finally set by the health care worker, the name of the patient 200, and the date in the memory 37 (S121 in FIG. 18A).

A screen indicating that the administration inquiry is complete is then displayed on the display component 38 of the portable terminal 300 (S122 in FIG. 16C and S122 in FIG. 17B).

The near field communication component 34 of the portable terminal 300 is then move closer to the near field communication component 25a of the pharmaceutical injection device 100, whereupon the pharmaceutical amount set by the health care worker is transmitted from the portable terminal 300 to the pharmaceutical injection device 100 (S118 in FIG. 18A), and a screen indicating that dose setting is complete is displayed on the display component 38 (S124 in FIG. 16C and S124 in FIG. 17B).

The pharmaceutical injection device 100 then receives the pharmaceutical amount set by the health care worker (S401 in FIG. 18A).

The pharmaceutical injection device 100 records the pharmaceutical amount set by the health care worker in the memory 32 (S402 in FIG. 18A).

2-3 Pharmaceutical Injection

Figure 18B:
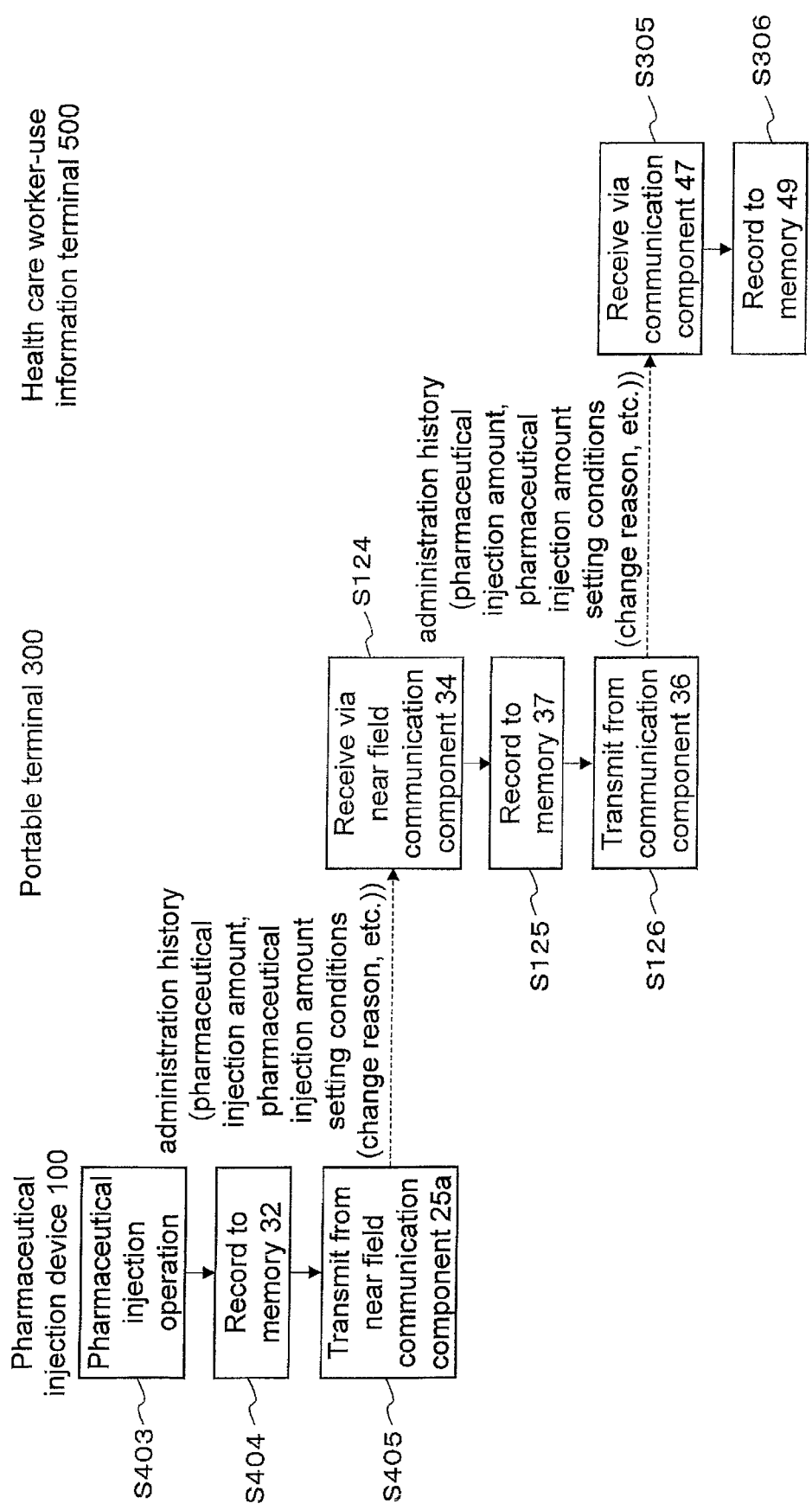
FIG. 18B is a flowchart of the control method in the pharmaceutical injection system shown in FIG. 1.

The injection of the pharmaceutical is executed on the basis of the pharmaceutical amount recorded to the memory 32. FIG. 18B is a flowchart of the pharmaceutical injection and the subsequent operation.

In injecting the pharmaceutical, the controller 25 executes the above-mentioned pharmaceutical injection operation shown in FIGS. 6 and 7 on the basis of the pharmaceutical amount stored in the memory 32 (S403 in FIG. 18B).

That is, the injection of the pharmaceutical in the pharmaceutical cartridge 9 is commenced by pressing the pharmaceutical injection switch 4 (see FIG. 3) provided to the outer peripheral surface of the main body case 1, as shown in FIGS. 6 and 7.

More specifically, the motor 13 of the piston drive mechanism 101 is actuated, the gear 12 linked to the motor 13 rotates, and this rotation of the gear 12 turns the feed screw 11, converting to the linear motion of the piston 10.

When the piston 10 moves downward (insertion direction C), the distal end of the piston 10 hits a gasket (not shown) at the rear end of the pharmaceutical cartridge (see FIG. 7). After that, the piston 10 is moved, causing the pharmaceutical inside the pharmaceutical cartridge 9 to go through the injection needle 16 mounted to the tip of the pharmaceutical cartridge 9 and be injected under the skin of the patient 200.

When the pharmaceutical injection operation ends, the pharmaceutical injection device 100 records the pharmaceutical administration history (administration log) in the memory 32 (S404 in FIG. 18B). This pharmaceutical administration history (administration log) includes the amount of pharmaceutical injected under the skin, the change reason transmitted to the health care worker-use information terminal 500 when the pharmaceutical injection amount is set, and so forth. Aside from the change reason, information related to the adjustment amount transmitted to the health care worker-use information terminal 500 when the pharmaceutical injection amount is set (such as information about the selection of the low key 613 or the high key 615) may also be transmitted.

After this pharmaceutical injection operation, the pharmaceutical administration history (administration log) is transmitted from the pharmaceutical injection device 100 to the portable terminal 300 (S405 in FIG. 18B).

Figure 16D:
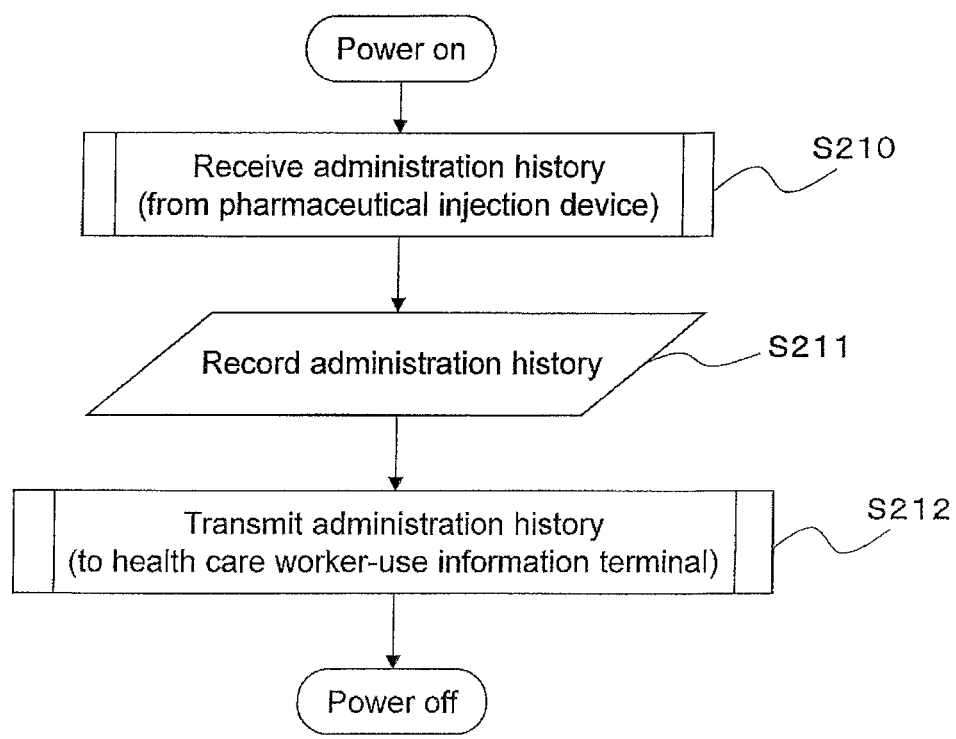
FIG. 16D is a flowchart of a method for controlling the portable terminal in the pharmaceutical injection system shown in FIG. 1.
Figure 17A:
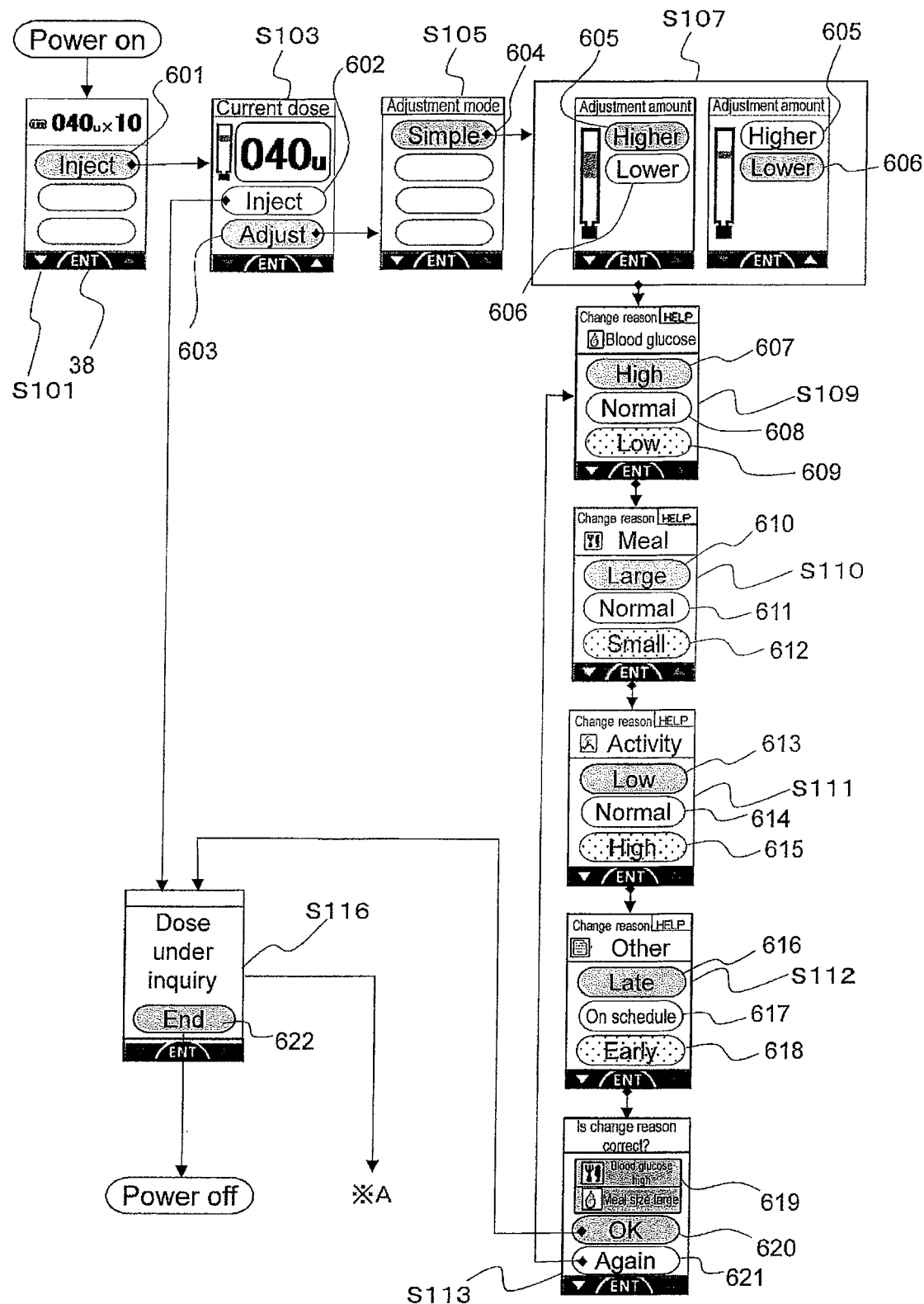
FIG. 17A is a flowchart of the display of the portable terminal in the control method shown in FIG. 16.
Figure 17B:
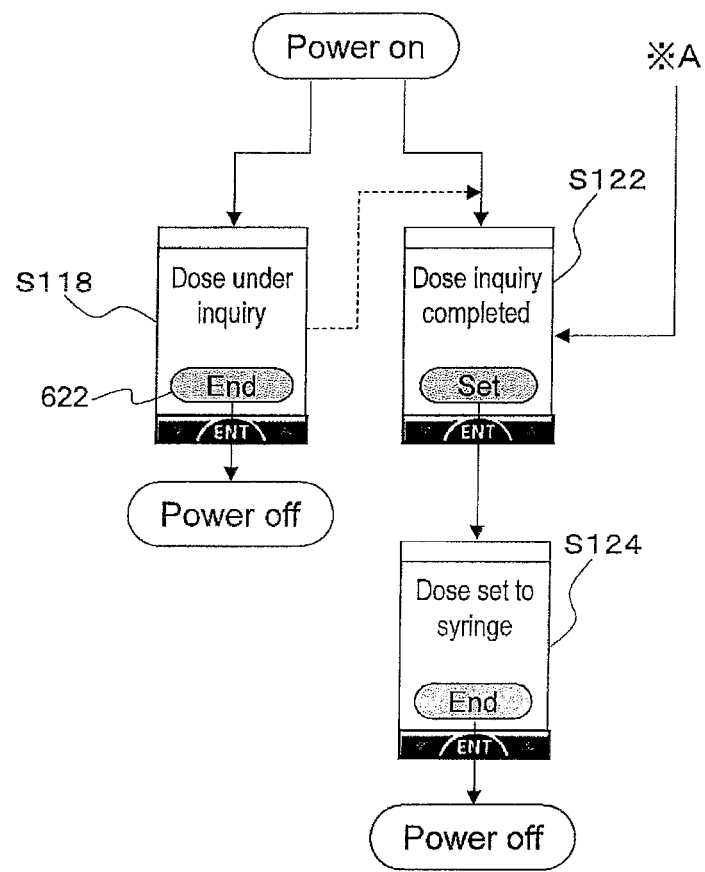
FIG. 17B is a flowchart of the display of the portable terminal in the control method shown in FIG. 16.

The portable terminal 300 receives the pharmaceutical administration history (administration log) from the pharmaceutical injection device 100 (S210 in FIG. 16D and S124 in FIG. 18B).

Upon receiving the administration history, the portable terminal 300 records the pharmaceutical administration history (administration log) in the memory 32 (S211 in FIG. 16D and S125 in FIG. 18B).

After this, the portable terminal 300 transmits the pharmaceutical administration history (administration log) to the health care worker-use information terminal 500 (S126 in FIG. 18B), and the power is turned off (S212 in FIG. 16D).

Upon receiving the pharmaceutical administration history (administration log) and the change reason, etc., from the pharmaceutical injection device 100 (S305 in FIG. 18B), the health care worker-use information terminal 500 records the pharmaceutical administration history (administration log) in the memory 49 (S306 in FIG. 18B).

Meanwhile, if the inject key 602 is selected in S102, an inquiry about the dose is transmitted to the health care worker-use information terminal 500 in order to confirm whether the pharmaceutical injection amount is the reference injection amount, and there is no problem (S201 in FIG. 16B). To put this another way, there is an inquiry as to whether no change is needed.

When the transmission is performed, an under inquiry screen is displayed (S116 in FIG. 16B and S116 in FIG. 17A).

Since the rest of the control is the same as above, it will not be described again. As to the change reason received by the portable terminal 300 in S121, if the health care worker is of the same opinion as the patient 200 and determines there is no need for adjustment, then "no change" is recorded.

Thus, in this embodiment, when the patient 200 inputs a desire to change the pharmaceutical injection amount according to his own condition and health management situation as in FIG. 17A from his own portable terminal 300, this desire is transmitted over the network 400 to the health care worker-use information terminal 500.

The health care worker examines the pharmaceutical change in light of this desire and the change reason (such as the above-mentioned blood glucose level, meal size, amount of activity, and other information), and sends it back from the health care worker-use information terminal 500 over the network 400 to the portable terminal 300 of the patient 200.

The patient 200 can transmit this result via the near field communication component 34 of the portable terminal 300 to the near field communication component 25a of the pharmaceutical injection device 100, and thereby change the pharmaceutical injection amount.

This final pharmaceutical dose (injection amount) is then stored along with the date, the change reason (such as the above-mentioned blood glucose level, meal size, amount of activity, and other information) in the memory 49 of the health care worker-use information terminal 500 and the memory 37 of the portable terminal 300.

Therefore, the health care worker and the patient 200 can cooperate on future improvements on the basis of this data at the time of later consultation.

Figure 19:
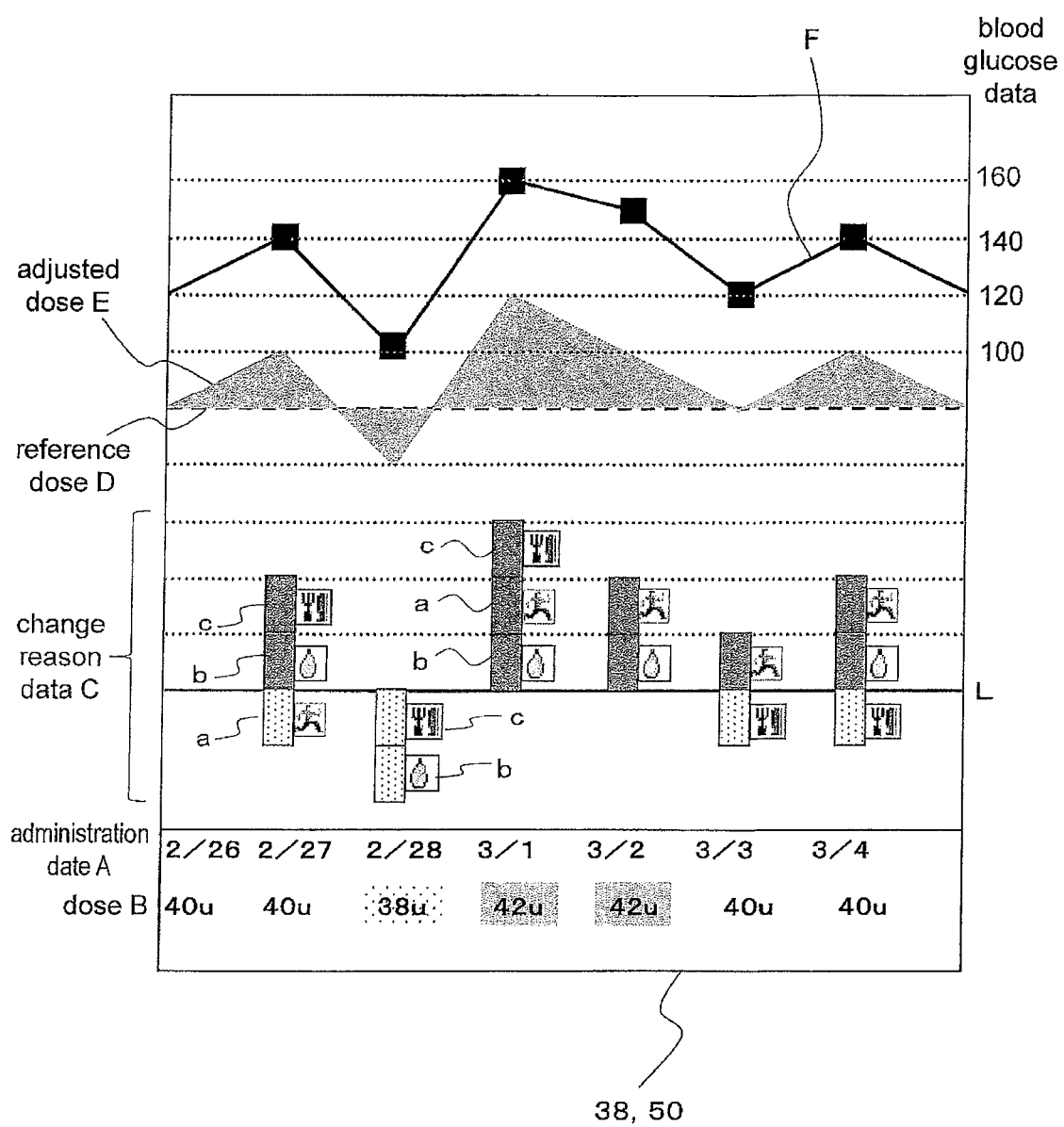
FIG. 19 is a diagram of the display of the health care worker-use information terminal and the portable terminal used in the pharmaceutical injection system shown in FIG. 1.

More specifically, FIG. 19 shows what is displayed on the display component 50 of the health care worker-use information terminal 500 and on the display component 38 of the portable terminal 300 owned by the patient 200.

The display on the display component 50 of the health care worker-use information terminal 500 shown in FIG. 19 can be produced by operating the input component 51. Also, the display on the display component 38 of the portable terminal 300 can be produced by operating the input component 39.

In FIG. 19, A is the date, B is the dose (injection amount), C is the change reason (such as the above-mentioned blood glucose level, meal size, amount of activity, and other information), D is the reference dose set for each patient 200, E is the adjusted dose, and F is the change in blood glucose level. Also, a is the amount of activity, b is the blood glucose level, and c is the meal size.

The health care worker can use the health care worker-use information terminal 500 to set a determination criterion for determining the validity of the adjustment amount of the pharmaceutical dose. The validity of the adjustment amount change due to the change reason transmitted from the portable terminal 300 is determined on the basis of this determination criterion.

Reasons for increasing the adjustment amount are when the blood glucose level is high, when the meal size is large, when the amount of activity is low, and when the administration date is late, and one point can be added for each. Specifically, when the blood glucose level is high, when the meal size is large, when the amount of activity is low, and when the administration date is late, this results in a total of four points.

Cases when no adjustment is needed are when the blood glucose level is normal, when the meal size is normal, when the amount of activity is normal, and when the administration date is as scheduled, in which cases no points are added, and if all of these categories are normal, this results in a total of zero points.

Reasons for decreasing the adjustment amount are when the blood glucose level is low, when the meal size is small, when the amount of activity is high, and when the administration date is early, and one point can be subtracted for each. Specifically, when the blood glucose level is low, when the meal size is small, when the amount of activity is high, and when the administration date is early, this results in a total of minus four points.

The health care worker can set the determination criterion so that the adjustment amount is set higher when there is a total of 2 to 4 points, no adjustment is performed when the point total is from −1 to +1, and the adjustment amount is set lower when the point total is from −4 to −2. Further, if the reference dose is 40 U, for example, the higher dose can be set to 42 U, for example, and the lower dose to 38 U. Thus, the health care worker sets the dose high or low and sets the determination criterion from the point total for setting the adjustment amount high, normal, or low.

That is, the dose set on February 26 was 40 U, but on February 27 the patient did some exercise (a), but the blood glucose level (b) was high and the meal size (c) was large, so the point total was +1. Therefore, it is determined from the above determination criterion not to perform adjustment, and the resulting pharmaceutical dose is 40 U.

By contrast, on February 28, the blood glucose level (b) was low and the meal size (c) was also small, so the point total is −2 points. Accordingly, it is decided from the determination criterion to set the adjustment amount lower, so the pharmaceutical dose is set to 38 U, which is 2 U lower than the reference dose of 40 U.

On March 1, the amount of activity was low (a), the blood glucose level (b) was high, and the meal size (c) was large, so the point total is +3 points. Therefore, it is decided from the determination criterion to set the adjustment amount higher, so the pharmaceutical dose is set to 42 U, which is 2 U higher than the reference dose of 40 U.

A higher amount of activity (a) is a reason for decreasing the dose, so this is shown below the line L and in a lighter color. On the other hand, a lower amount of activity (a) is a reason for increasing the dose, so this is shown above the line L and in a darker color. A lower blood glucose level (b) is a reason for decreasing the dose, so this is shown below the line L and in a lighter color. On the other hand, a higher blood glucose level (b) is a reason for increasing the dose, so this is shown above the line L and in a darker color. A smaller meal size (c) is a reason for decreasing the dose, so this is shown below the line L and in a lighter color. On the other hand, a larger meal size (c) is a reason for increasing the dose, so this is shown above the line L and in a darker color.

When FIG. 19 is displayed on the display component 50 of the health care worker-use information terminal 500 and on the display component 38 of the portable terminal 300 owned by the patient 200, the health care worker and the patient 200 can share, in an easy to understand fashion, specific measures to take in the future. Therefore, a future improvement plan can be carried out more easily.

3. Main Features 3-1

The pharmaceutical injection system in this embodiment comprises the pharmaceutical injection device 100 for injecting a pharmaceutical, the portable terminal 300 for setting a pharmaceutical injection amount for the pharmaceutical injection device 100, and the health care worker-use information terminal 500 that is capable of communicating with the portable terminal 300.

The portable terminal 300 has the input component 39 (an example of a first input component), the communication component 36 (an example of a first transmitter, and an example of a first receiver), and the near field communication component 34 (an example of a second transmitter). The input component 39 is used to input pharmaceutical injection amount setting conditions for setting the pharmaceutical injection amount. The communication component 36 transmits the inputted pharmaceutical injection amount setting conditions to the health care worker-use information terminal 500. The communication component 36 receives a pharmaceutical injection amount set on the basis of the pharmaceutical injection amount setting conditions transmitted from the health care worker-use information terminal 500. The near field communication component 34 transmits the received pharmaceutical injection amount to the pharmaceutical injection device 100.

The health care worker-use information terminal 500 has the communication component 47 (an example of a second receiver, and an example of a third transmitter) and the input component 51 (an example of a second input component). The communication component 47 receives the pharmaceutical injection amount setting conditions transmitted from the portable terminal 300. The input component 51 is used to input the pharmaceutical injection amount set on the basis of the received pharmaceutical injection amount setting conditions. The communication component 47 transmits the inputted pharmaceutical injection amount to the portable terminal 300.

The pharmaceutical injection device 100 has the cartridge holder 7, the main body case 1, the piston 10, the piston drive mechanism 101, the near field communication component 25a (an example of a third receiver), and the controller 25. The cartridge holder 7 allows the pharmaceutical cartridge 9 to be mounted to it. The cartridge holder 7 is provided openably and closeably to the main body case 1. The piston 10 can be inserted into the pharmaceutical cartridge 9 mounted to the cartridge holder 7 inside the main body case 1. The piston drive mechanism 101 moves the piston 10 so that it is inserted into the pharmaceutical cartridge 9. The near field communication component 25a receives the pharmaceutical injection amount transmitted from the portable terminal 300. The controller 25 drives the piston drive mechanism 101 on the basis of the received pharmaceutical injection amount.

In this embodiment, for example, when pharmaceutical injection amount setting conditions are inputted by the patient from the input component 39 of the portable terminal 300, the pharmaceutical dose set by the health care worker is transmitted through the portable terminal 300 to the pharmaceutical injection device 100, so the pharmaceutical dose can be changed without having to go to a medical facility, which is extremely convenient for the user.

3-2

Also, in the above embodiment, the portable terminal 300 further has the memory 37 (an example of a first memory) and the display component 38 (an example of a first display component). The memory 37 stores the pharmaceutical injection amount setting conditions inputted to the input component 39 (the first input component) and the pharmaceutical injection amount received from the health care worker-use information terminal 500. The display component 38 displays the pharmaceutical injection amount and the pharmaceutical injection amount setting conditions stored in the memory 37 in graph format. The health care worker-use information terminal 500 further has the memory 49 (an example of a second memory) and the display component 50 (an example of a second display component). The memory 49 stores the pharmaceutical injection amount setting conditions transmitted from the portable terminal 300 and the pharmaceutical injection amount inputted from the input component 51 (an example of a second input component). The display component 50 (an example of a second display component) displays the pharmaceutical injection amount and the pharmaceutical injection amount setting conditions stored in the memory 49 in graph format.

Accordingly, the pharmaceutical injection amount and the pharmaceutical injection amount setting conditions stored in the memory 37 can be displayed on the display component 38 of the portable terminal 300 on the basis of an instruction from the input component 39. Also, the pharmaceutical injection amount and the pharmaceutical injection amount setting conditions stored in the memory 49 can be displayed on the display component 50 of the health care worker-use information terminal 500 on the basis of an instruction from the input component 51.

In other words, the patient and the health care worker can each continuously store the pharmaceutical injection amount and the pharmaceutical injection amount setting conditions with the portable terminal 300 and the health care worker-use information terminal 500, respectively, and they can also do visual checks, which makes it easier to deal with disease, and convenience is good from this standpoint as well.

3-3

With the pharmaceutical injection system in this embodiment, the change reason (an example of pharmaceutical injection amount setting conditions) and information related to an adjustment amount for adjusting the pharmaceutical injection amount are inputted to the input component 39 (an example of a first input component). The communication component 36 (an example of a first transmitter) transmits information related to the adjustment amount to the health care worker-use information terminal 500. A determination criterion that is set in order to determine the validity of an adjustment amount is inputted to the input component 51 (an example of a second input component). The health care worker-use information terminal 500 further has the display component 50 (an example of a second display component). The display component 50 displays the adjustment amount, the change reason (an example of pharmaceutical injection amount setting conditions), and the determination result based on the determination criterion. The communication component 47 (an example of a third transmitter) transmits advice to the patient 200 (an example of a user) and evaluation comments inputted via the input component 51 on the basis of the determination result to the portable terminal 300 along with the determination result.

This allows the patient 200 to receive advice without a visit to the physician 501.

3-4

The method for controlling the pharmaceutical injection system of the above embodiment is a method for controlling a pharmaceutical injection system comprising the pharmaceutical injection device 100 for injecting a pharmaceutical, the portable terminal 300 for setting a pharmaceutical injection amount for the pharmaceutical injection device 100, and the health care worker-use information terminal 500 that is capable of communicating with the portable terminal 300, said method comprising S100 (an example of a first input step), S115 (an example of a first transmission step), S301 (an example of a first reception step), S302 (an example of a second input step), S304 (an example of a second transmission step), S116 (an example of a second reception step), S118 (an example of a third transmission step), S401 (an example of a third reception step), and S402 (an example of a storage step).

S100 (an example of a first input step) is a step of inputting pharmaceutical injection amount setting conditions for setting a pharmaceutical injection amount. S115 (an example of a first transmission step) is a step of transmitting the inputted pharmaceutical injection amount setting conditions from the portable terminal 300 to the health care worker-use information terminal 500. S301 (an example of a first reception step) is a step in which the health care worker-use information terminal 500 receives the pharmaceutical injection amount setting conditions transmitted from the portable terminal 300. S302 (an example of a second input step) is a step in which the pharmaceutical injection amount set on the basis of the received pharmaceutical injection amount setting conditions is inputted to the health care worker-use information terminal 500. S304 (an example of a second transmission step) is a step of transmitting the inputted pharmaceutical injection amount from the health care worker-use information terminal 500 to the portable terminal 300. S116 (an example of a second reception step) is a step in which the portable terminal 300 receives the pharmaceutical injection amount transmitted from the health care worker-use information terminal 500. S118 (an example of a third transmission step) is a step of transmitting the received pharmaceutical injection amount from the portable terminal 300 to the pharmaceutical injection device 100. S401 (an example of a third reception step) is a step in which the pharmaceutical injection device 100 receives the pharmaceutical injection amount transmitted from the portable terminal 300. S402 (an example of a storage step) is a step of storing the received pharmaceutical injection amount in the pharmaceutical injection device 100.

4. Other Embodiments

An embodiment of the present invention is described above, but the present invention is not limited to or by the above embodiment, and various modifications are possible without departing from the gist of the invention.

(A)

In the above embodiment, blood glucose level, meal size, and amount of activity are provided as reasons for changing the pharmaceutical injection amount, and determination criteria (in the above embodiment, high (large) (2 to 4 ), normal (1 to 1), and low (small) (−4 to −2)) are provided so as to change the adjustment amount in three stages (high (large), normal, and low (small)) on the basis of the point total, with each reason accounting for one point, but the change reasons may be weighted and the determination criteria may be provided so that the adjustment amount is changed in five stages.

For example, the weighting of the change reasons can be set as follows. In the case of blood glucose level, 2 points can be given for "high," 0 points for "normal," and −2 points for "low." In the case of meal size, +1.5 points can be given for "large," 0 points for "normal," and −1.5 points for "small." For amount of activity, +1 point can be given for "high," 0 points for "normal," and −1 point for "low." If the administration date is given as another change reason, +0.5 point can be given for "late," 0 points for "normal," and −0.5 point for "early."

The determination criteria can also be such that an adjustment amount level 1 is determined when the point total is at least 3 and no more than 5, an adjustment amount level 2 is determined when the point total is at least 1.5 and less than 3, an adjustment amount level 3 is determined when the point total is greater than −1.5 and no more than 1.5, an adjustment amount level 4 is determined when the point total is greater than −3 and no more than −1.5, and an adjustment amount level 5 is determined when the point total is at least −5 and no more than −3. If we let the reference dose be 40 U, then the amount will be 45 U at adjustment amount level 1, 42 U at adjustment amount level 2, 40 U at adjustment amount level 3, 38 U at adjustment amount level 4, and 35 U at adjustment amount level 5.

Figure 20:
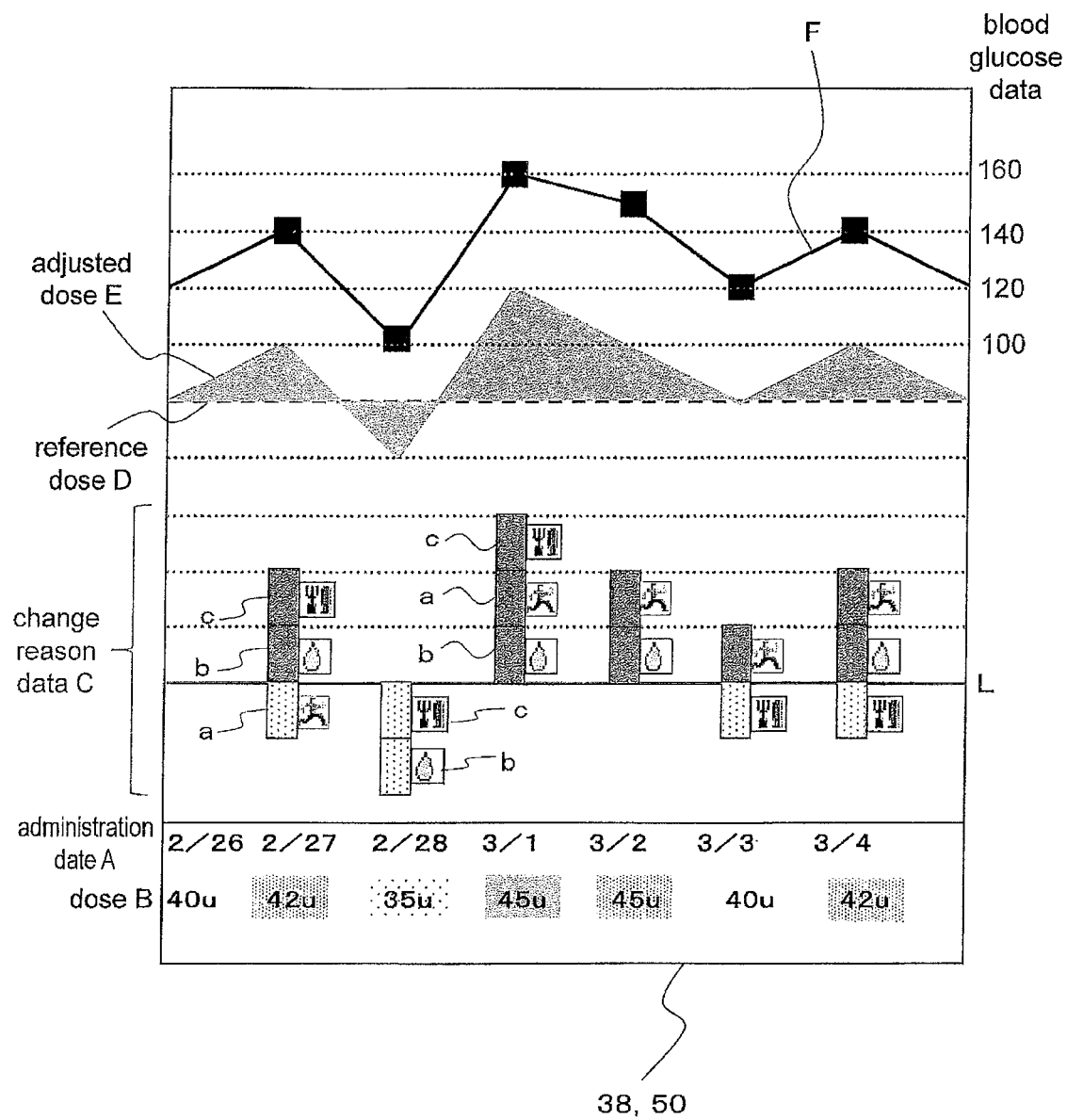
FIG. 20 is a diagram of the display of the health care worker-use information terminal and the portable terminal in the pharmaceutical injection system in a modification example of this embodiment.

Specifically, if weighting is performed using the data shown in FIG. 19, on February 27 the patient did some exercise (a), but the blood glucose level (b) was high and the meal size (c) was large, so the point total was 2−1+1.5=2.5 points, as shown in FIG. 20. Therefore, the adjustment amount level 2 is determined from the above-mentioned determination reference, and as a result the pharmaceutical dose is set at 42 U.

By contrast, on February 28, the blood glucose level (b) was low and the meal size (c) was also small, so the point total is −2−1.5=−3.5 points. Therefore, the adjustment amount level 5 is determined from the above-mentioned determination reference, and the pharmaceutical dose is set at 35 U, which is 5 U lower than the reference dose of 40 U.

On March 1, the amount of activity was low (a), the blood glucose level (b) was high, and the meal size (c) was large, so the point total is 1+2+1.5=4.5 points. Therefore, the adjustment amount level 1 is determined from the above-mentioned determination reference, and as a result the pharmaceutical dose is set at 45 U, which is 5 U higher than the reference dose of 40 U.

Setting as above may, for example, result in a situation in which it is unfavorable to lower the adjustment amount, such as when the blood glucose level is high, the meal size is small, the amount of activity is high, and the administration date is early, but such situations can be made less likely to occur by weighting the change reasons.

When the determination criteria are thus set in five stages, the display screen shown in 5107 in FIG. 17A may be changed to the screen shown in FIGS. 21a to 21d.

Figure 21:
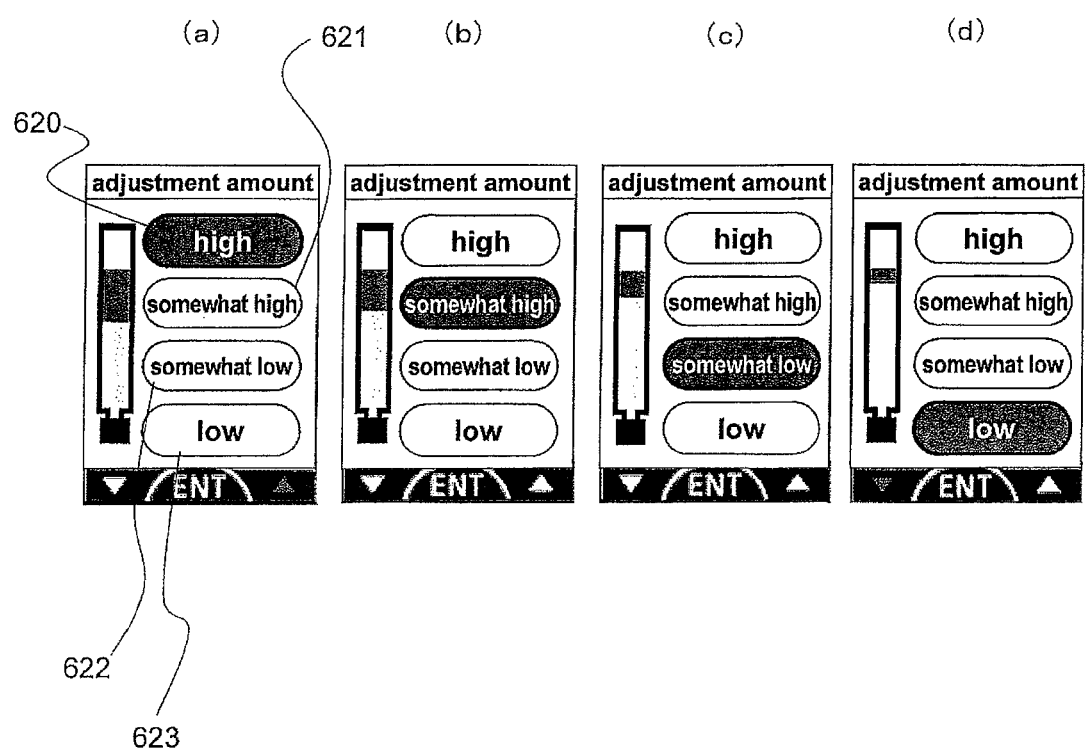
FIG. 21 is a diagram of the display of the portable terminal in the pharmaceutical injection system in a modification example of this embodiment.

In FIG. 17A, since the adjustment amount levels desired by the patient 200 are in three stages, two different keys are displayed, namely, the increase key 605 and the decrease key 606, but in FIG. 21, because there are five stages, four different keys are provided, namely, a high key 620, a somewhat high key 621, a somewhat low key 622, and a low key 623. Specifically, the patient 200 uses the high key 620 to increase the pharmaceutical dose, uses the somewhat high key 621 to increase the pharmaceutical dose somewhat, uses the somewhat low key 622 to decrease the pharmaceutical dose somewhat, and uses the low key 623 to decrease the pharmaceutical dose. Four states are shown in which each of these keys is selected, with the selected key being highlighted.

Because the patient 200 is the one who performs the key selection, a change in the settings according to the wishes of the patient 200 is not necessarily performed by a health care worker. Therefore, information related to the adjustment amount need not be transmitted to the health care worker-use information terminal 500, but the wishes of the patient can be conveyed to the health care worker by transmitting the adjustment amount level desired by the patient 200 (an example of information related to the adjustment amount) to the health care worker-use information terminal 500. This allows both parties to be cognizant of adjustment to the pharmaceutical dose, which can be helpful in treatment.

Furthermore, weighting of the change reasons may also be performed when there are three stages to the adjustment amount.

(B)

Also, since the portable terminal 300 belonging to the patient 200 is provided with the near field communication component 34, and the health care worker-use information terminal 500 is provided with the near field communication component 52, communication between the portable terminal 300 and the health care worker-use information terminal 500 can be performed between the near field communication component 34 and the near field communication component 52 using near field communication, without going over the network 400.

The near field communication component 52 provided to the health care worker-use information terminal 500 need not be provided if no near field communication is to be performed.

(C)

In the above embodiment, the health care worker transmits the final dose (injection amount) of the pharmaceutical along with the date and so forth to the portable terminal 300, but a determination result, comments, advice, and so forth from the physician 501 may also be transmitted.

Figure 22:
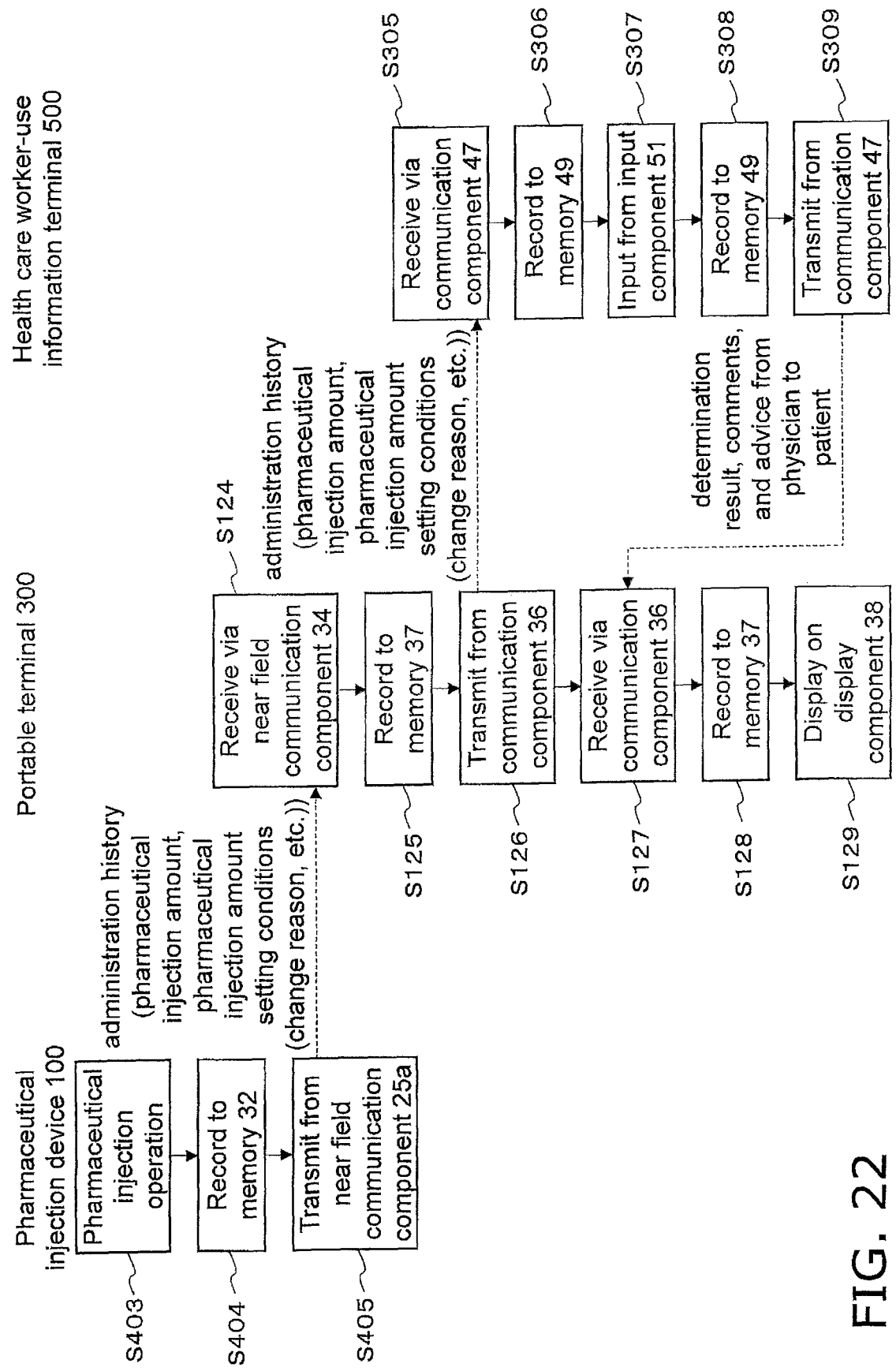
FIG. 22 is a flowchart of the control method in the pharmaceutical injection system in a modification example of this embodiment.

FIG. 22 is a flowchart of the operation of the pharmaceutical injection system when a determination result, comments, advice, and so forth from the physician 501 are transmitted from the health care worker-use information terminal 500 to the portable terminal 300. FIG. 22 differs from FIG. 18A in that S127 to S129 and S307 to S309 are added.

In S306, a diagnosis is made by the physician 501 after the health care worker-use information terminal 500 has recorded the pharmaceutical administration history (administration log) in the memory 49.

Next, a determination result, comments, advice, and so forth from the physician 501 are inputted through the input component 51 to the health care worker-use information terminal 500 (S307 in FIG. 22), and the determination result, comments, advice, and so forth are stored in the memory 49 (S308 in FIG. 22).

Next, the determination result, comments, advice, and so forth are transmitted from the communication component 47 of the health care worker-use information terminal 500 to the portable terminal 300 (S309 in FIG. 22).

Upon receiving the determination result, comments, advice, and so forth (S127 in FIG. 22), the portable terminal 300 stores them in the memory 37 via the communication component 36 (S128 in FIG. 22).

The portable terminal 300 then displays the received determination result, comments, advice, and so forth on the display component 38 (S129 in FIG. 22).

An example of the determination result, comments, advice, and so forth from the physician 501 will now be described.

(C-1)

FIG. 23 shows an example of the determination result, comments, advice, and so forth from the physician 501. In FIG. 23, an example is shown in which there are five stages of adjustment amount, with the change reasons weighted as shown in FIG. 20.

This example shows the adjustment amount inputted by the patient 200 on the administration date, the change reason, the valid adjustment amount at the health care worker-use information terminal 500, the determination result and evaluation comments by the physician 501, and advice to the patient 200. The determination result and comments may be transmitted once a week, for example.

On February 27, for instance, the patient 200 wishes to increase the adjustment amount somewhat, and since the valid adjustment amount according to the health care worker-use information terminal 500 of the physician 501 calls for increasing somewhat, the adjustment amounts match, and the determination result is "good." Also, a comment from the physician 501 of "Since blood glucose was low the next day, either the dose may not be adjusted, or activity may be reduced" is transmitted to the portable terminal 300.

Meanwhile, on February 28, the patient 200 wishes to decrease the adjustment amount somewhat, but since the blood glucose level is low, the meal size is small, the amount of activity is normal, and the administration date is as scheduled, the point total is −2−1.5=−3.5. Therefore, the physician 501 determines that a decrease is appropriate for the adjustment amount. Also, the physician 501 gives a determination result of "fair," and comments "A small adjustment amount is preferable, but a higher blood glucose level the next day may be a result of that."

As discussed above, the patient 200 can manage his own health on the basis of advice from the physician 501 by having the physician transmit comments. Specifically, if the adjustment amount desired by the patient 200 matches the adjustment amount ultimately decided by the physician 501, the determination result is marked "good." If the adjustment amount desired by the patient 200 is higher or somewhat higher, and the adjustment amount ultimately decided by the physician 501 is somewhat higher or higher, the determination result is marked with "fair." Also, if the adjustment amount desired by the patient 200 is lower or somewhat lower, and the adjustment amount ultimately decided by the physician 501 is somewhat lower or lower, the determination result is marked with "fair."

If, for example, the valid determination result is somewhat lower or lower, even though the patient 200 desires an adjustment amount that is somewhat higher or higher, or if the valid determination result is somewhat higher or higher, even though the patient 200 desires an adjustment amount that is somewhat lower or lower, the determination result is marked "no good," and a comment is left to the effect that there is an error in the adjustment.

(C-2)

FIG. 24 shows an example of determination results, comments, advice, and so forth from the physician 501 when the change reasons are weighted and there are three stages to the adjustment amount.

The weighting of the change reasons can be set as follows, for example. In the case of blood glucose level, 2 points can be given for "high," 0 points for "normal," and −2 points for "low." In the case of meal size, +1.5 points can be given for "large," 0 points for "normal," and −1.5 points for "small." For amount of activity, +1 point can be given for "high," 0 points for "normal," and −1 point for "low." If the administration date is given as another change reason, +0.5 point can be given for "late," 0 points for "normal," and −0.5 point for "early."

As a valid adjustment amount, it is set higher (42 U) if the point total is 2.5 to 5 points, set to no adjustment (40 U) if the point total is −2 to 2 points, and set lower (38 U) if the point total is −2.5 to −5 points.

For example, on February 26, the patient 200 desires no adjustment, and the adjustment amount recommended by the health care worker-use information terminal 500 of the physician 501 is also no adjustment, so the adjustment amounts match, and the determination result is "good."

Meanwhile, on February 27, the patient 200 desires no adjustment, but the blood glucose level is high, the meal size is large, the amount of activity is high, and the administration date is as scheduled, so the point total is 2+1.5−1=2.5. Therefore, the physician 501 determines an increase to be appropriate for the adjustment amount. Also, the physician 501 marks the determination result as "fair," and comments "An increase is preferable for the adjustment amount. Let's reduce meal size."

As discussed above, the patient 200 can manage his own health on the basis of advice from the physician 501 by having the physician transmit comments. Specifically, if the adjustment amount desired by the patient 200 matches the adjustment amount ultimately decided by the physician 501, the determination result is marked "good." If the adjustment amount desired by the patient 200 is no adjustment or higher, and the adjustment amount ultimately decided by the physician 501 is higher or no adjustment, the determination result is marked with "fair." Also, if the adjustment amount desired by the patient 200 is no adjustment or lower, and the adjustment amount ultimately decided by the physician 501 is lower or no adjustment, the determination result is marked with "fair."

If the valid determination result is lower, even though the adjustment amount desired by the patient 200 is higher, or if the valid determination result is higher, even though the adjustment amount desired by the patient 200 is lower, etc., the determination result is marked "no good," and a comment is left to the effect that there is an error in the adjustment.

The adjustment amount may be in three stages, with no weighting performed for each change reason.

(D)

In the above embodiment, the communication component 36 of the portable terminal 300 served as both an example of the first transmitter of the present invention and as an example of the first receiver, but a transmitter and a receiver may be provided separately.

(E)

In the above embodiment, the communication component 47 of the health care worker-use information terminal 500 served as both an example of the third transmitter of the present invention and as an example of the second receiver, but a transmitter and a receiver may be provided separately.

Embodiment 2

Next, the pharmaceutical injection system in Embodiment 2 pertaining to the present invention will be described.

The pharmaceutical injection system in Embodiment 2 differs from the one in Embodiment 1 in that no portable terminal is provided, and a change to the adjustment amount is made by the pharmaceutical injection device to which pharmaceutical amount adjustment conditions have been inputted by the physician 501 ahead of time. Therefore, the patient 200 does not have to visit the physician 501 every time he wishes to change the adjustment amount, making the system more convenient.

Specifically, in Embodiment 1 the portable terminal 300 is used for inputting change reasons 1 to 4, but in Embodiment 2 the change reasons to 4 are inputted with the pharmaceutical injection device, and changes to the adjustment amount are made by using setting information inputted from the health care worker-use information terminal ahead of time, at the pharmaceutical injection device on the basis of the result of inputting the change reasons to 1 to 4.

1. Configuration

Pharmaceutical Injection System

Figure 25:
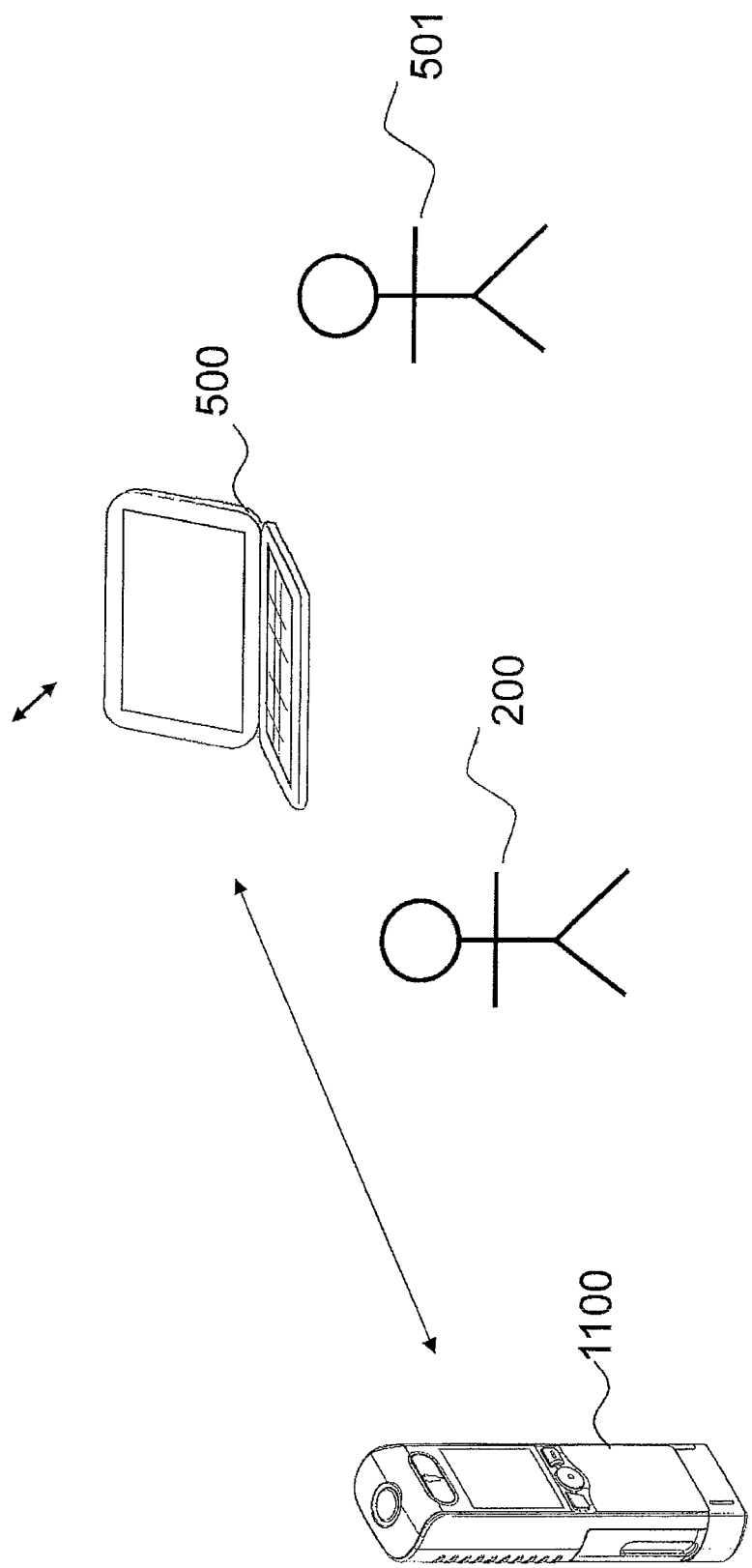
FIG. 25 is a diagram of the configuration of the pharmaceutical injection system in Embodiment 2.

FIG. 25 shows the configuration of the pharmaceutical injection system in Embodiment 2. As shown in FIG. 25, the pharmaceutical injection system in Embodiment 2 comprises a pharmaceutical injection device 1100 and a health care worker-use information terminal 500.

The pharmaceutical injection device 1100 is capable of near field communication with the health care worker-use information terminal 500, and receives pharmaceutical amount adjustment from the health care worker-use information terminal 500 when the patient 200 visits the physician 501.

Pharmaceutical Injection Device

The pharmaceutical injection device 1100 in this embodiment has the same basic structure as in Embodiment 1, but comprises a setting information memory 1101 for adjusting the pharmaceutical amount, a change reason weighting determination component 1102, an injection amount calculation processor 1103, etc. In Embodiment 2, components that are the same as in Embodiment 1 will not be described again.

Figure 26:
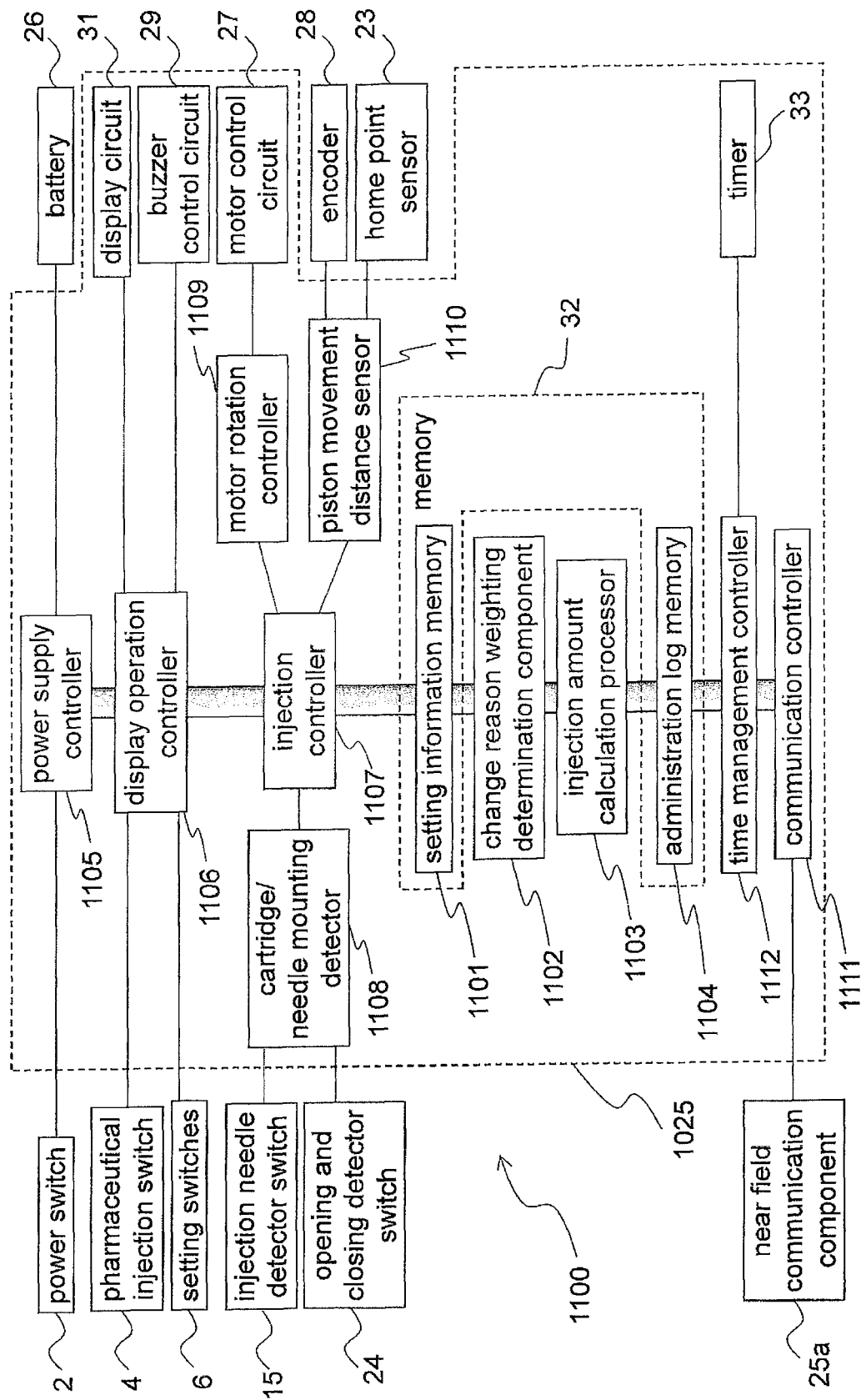
FIG. 26 is a control block diagram of the pharmaceutical injection device in the pharmaceutical injection system in FIG. 25.

FIG. 26 is a control block diagram of the pharmaceutical injection device 1100 in Embodiment 2. The pharmaceutical injection device 1100 in Embodiment 2 has the configuration of the pharmaceutical injection device 100, but there is also configuration not shown in FIG. 26 (for instance, the display component 5 is connected to the display circuit 31, but this is not shown in FIG. 26).

A controller 1025 of the pharmaceutical injection device 1100 in Embodiment 2 is provided with a memory 32 that includes the setting information memory 1101 and an administration log memory 1104, the change reason weighting determination component 1102, the injection amount calculation processor 1103, a power supply controller 1105, a display operation controller 1106, an injection controller 1107, a cartridge/needle mounting detector 1108, a motor rotation controller 1109, a piston movement distance sensor 1110, a communication controller 1111, a time management controller 1112, a buzzer control circuit 29, a motor control circuit 27, and a timer 33.

The setting information memory 1101 is a part of the memory 32, and stores setting information for adjusting and setting the pharmaceutical injection amount that is inputted by the physician 501 to the health care worker-use information terminal 500 and received through the near field communication component 25a.

The change reason weighting determination component 1102 performs weighting when changing from the reference dose on the basis of the change reasons inputted by the patient 200 from the display component 5.

The injection amount calculation processor 1103 calculates an adjustment amount on the basis of the point total for each change reason after weighting, and adds the adjustment amount to the reference dose to calculate the pharmaceutical injection amount.

The administration log memory 1104 is a part of the memory 32, and stores a pharmaceutical administration history (administration log).

The power supply controller 1105 controls the power switch 2 and the battery 26, and supplies power when the power switch 2 is pressed.

The display operation controller 1106 is connected to the display component 5 via the display circuit 31, and is also connected to the setting switches 6 and the pharmaceutical inject switch. More specifically, the keys displayed on the display component 5 can be selected with the setting switches 6 under control of the display operation controller 1106. As shown in FIG. 2, there are three setting switches 6, so the middle key can be an enter key, and the keys on either side can be select keys for moving up and down. When a plurality of keys are displayed on the display component 5 (S103 in FIG. 17A), up and down selection is performed with the select keys, and the selected key can be entered with the enter key. Thus, in Embodiment 2, the patient 200 uses the setting switches 6 to manipulate the keys displayed on the display component 5, and thereby inputs the change reasons and so forth described in Embodiment 1.

The injection controller 1107 controls the motor control circuit 27 via the motor rotation controller 1109 on the basis of the movement distance of the piston sensed by the piston movement distance sensor 1110 using the encoder 28 and the home point sensor 23. The injection controller 1107 is also connected to the cartridge/needle mounting detector 1108, and the cartridge/needle mounting detector 1108 detects the mounting of the cartridge and needle on the basis of the detection results of the injection needle detector switch 15 and the opening and closing detector switch 24.

The communication controller 1111 controls communication with the near field communication component 52 of the health care worker-use information terminal 500 by the near field communication component 25a.

The time management controller 1112 manages control of the timer 33.

The configuration of the health care worker-use information terminal 500 is the same as in Embodiment 1.

2. Operation

Operation of Pharmaceutical Injection System

Figure 27:
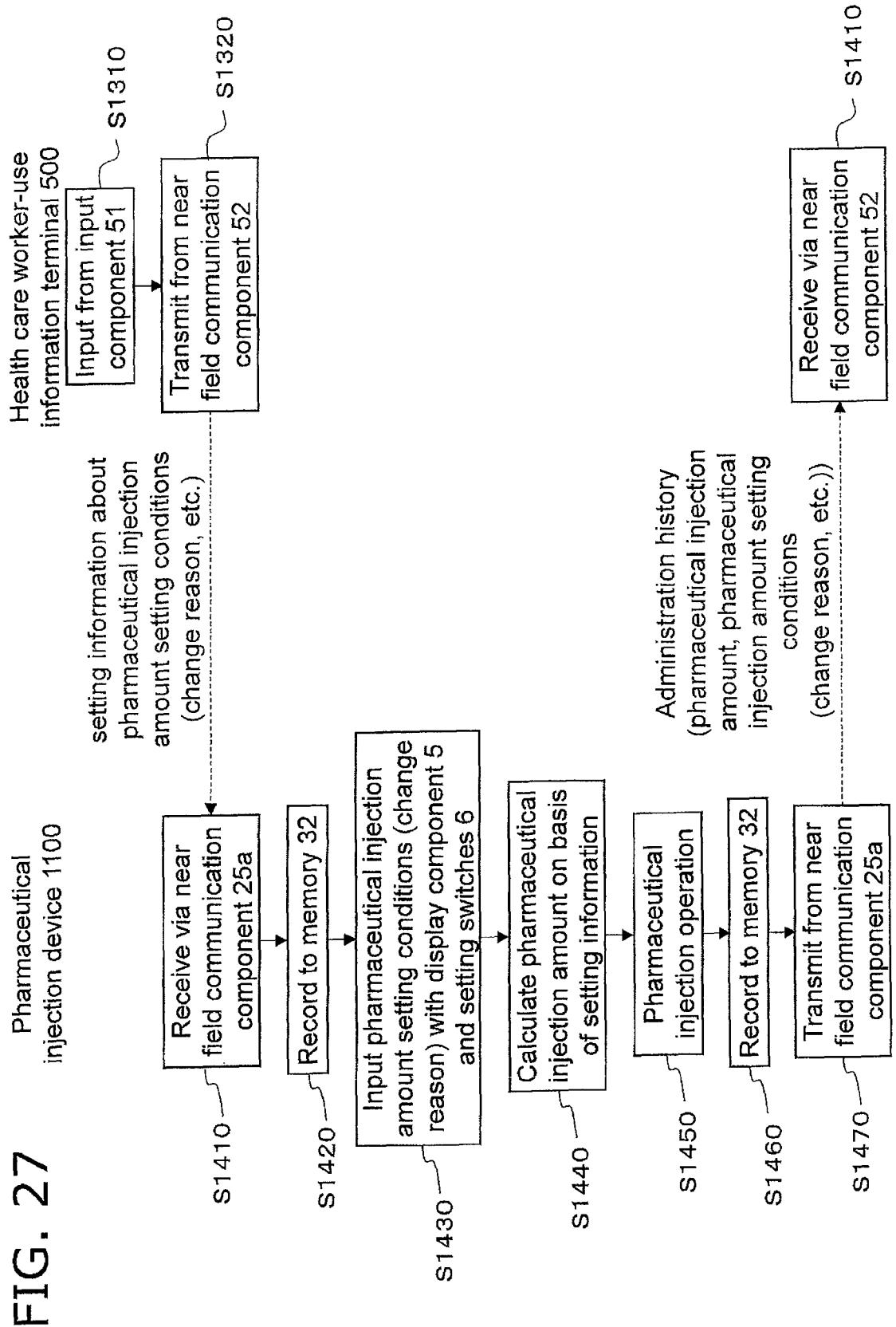
FIG. 27 is a flowchart of the control method in the pharmaceutical injection system in FIG. 25.

FIG. 27 is a flowchart of the control of the pharmaceutical injection system in Embodiment 2.

As shown in FIG. 27, first setting information is inputted by the physician 501 through the input component 51 (S1310 in FIG. 27). Examples of setting information include the reference dose, the adjustment amount level, change reason data for dose adjustment, combinations of change reasons, and weighting parameters.

The inputted setting information is transmitted from the near field communication component 52 to the pharmaceutical injection device 1100 by communication between the near field communication component 25a of the pharmaceutical injection device 1100 and the near field communication component 52 of the health care worker-use information terminal 500 when the patient 200 visits the physician 501 (S1320 in FIG. 27).

When the setting information is transmitted from the near field communication component 52 to the pharmaceutical injection device 1100, the pharmaceutical injection device 1100 performs the following operations.

Operation of Pharmaceutical Injection Device

The operation of the pharmaceutical injection device in Embodiment 2 will be described for each other components of the pharmaceutical injection device 1100.

Operation of Communication Controller

Figure 28:
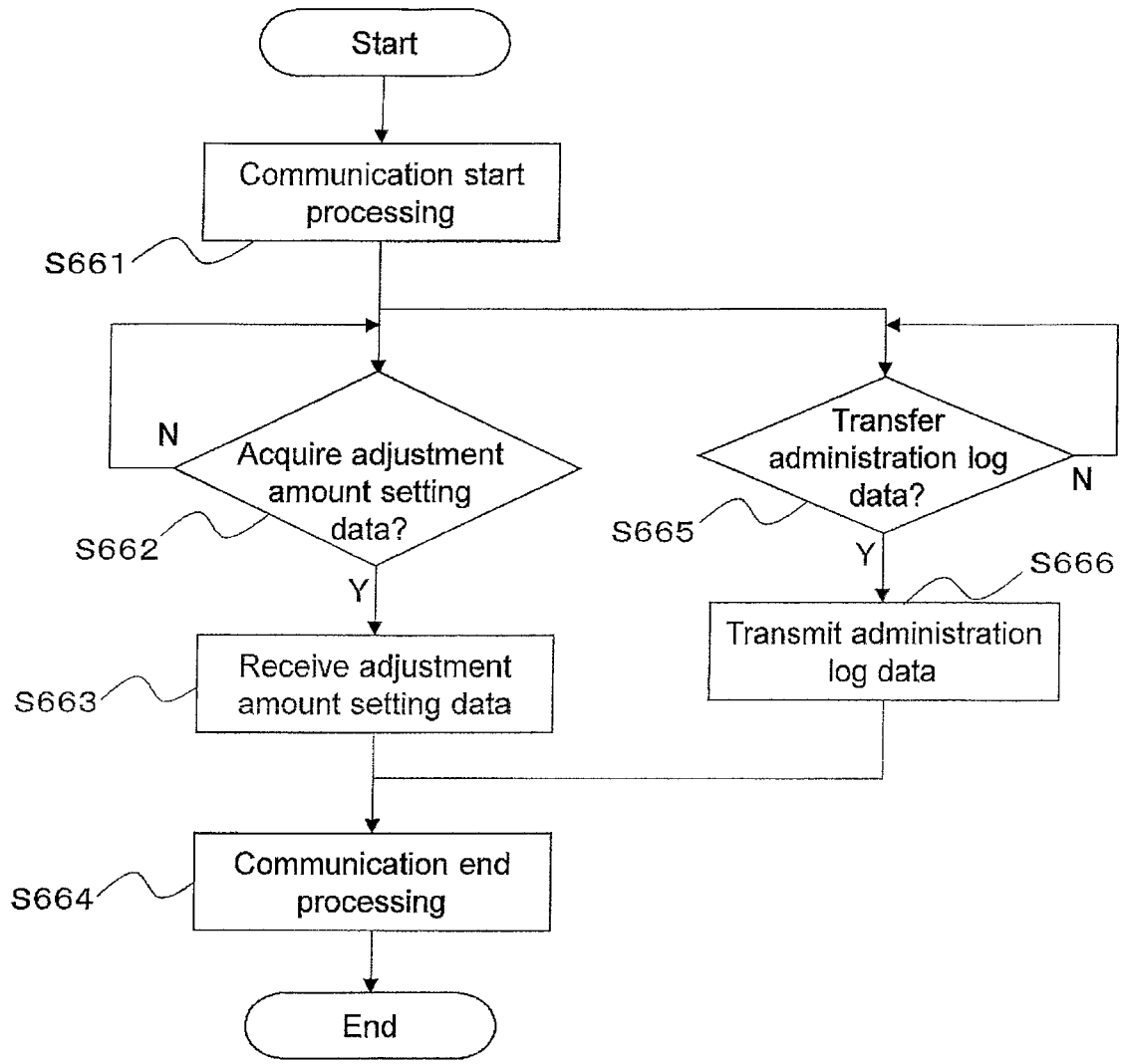
FIG. 28 is a flowchart of the operation of the communication controller in FIG. 26.

FIG. 28 is a flowchart of the operation of the communication controller 1111.

When the communication controller 1111 receives setting information from the health care worker-use information terminal 500 (S1410 in FIG. 27), the communication controller 1111 controls the near field communication component 25a to start communication processing (S661), after which adjustment amount setting data (setting information) is received and communication end processing is performed as shown in 5662 and 5663 (S664).

Operation of Setting Information Memory

Figure 29:
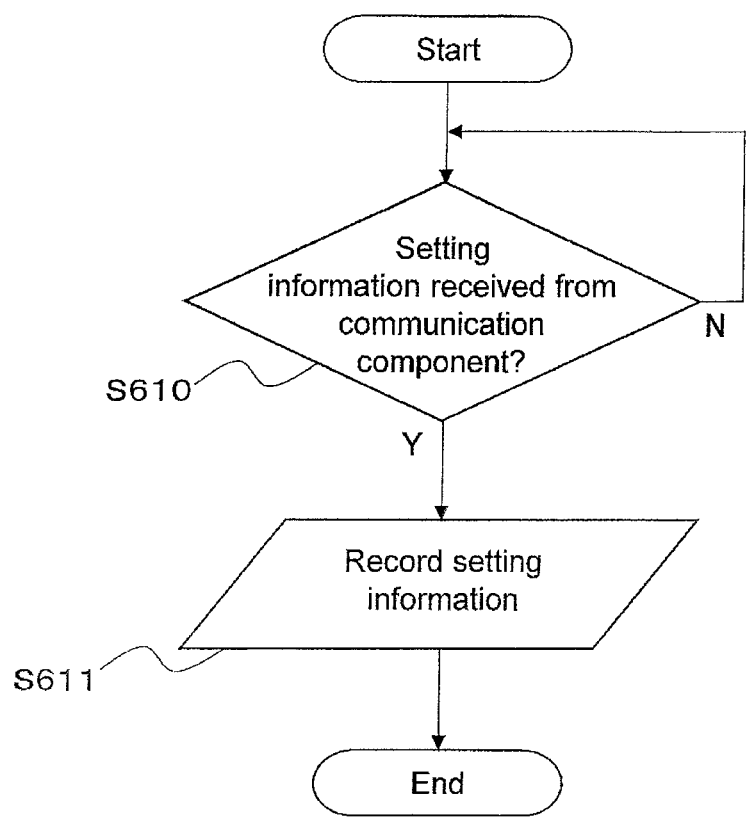
FIG. 29 is a flowchart of the operation of the setting information memory in FIG. 26.

FIG. 29 is a flowchart of the operation of the setting information memory 1101. The setting information memory 1101 receives setting information from the health care worker-use information terminal 500 by performing communication between the near field communication component 25a of the pharmaceutical injection device 1100 and the near field communication component 52 of the health care worker-use information terminal 500 when the patient 200 visits the physician 501 (S610 in FIGS. 29 and S1410 in FIG. 27). The pharmaceutical injection device 1100 records the received setting information in the setting information memory 1101 of the memory 32 (S611 in FIGS. 29 and S1420 in FIG. 27).

FIGS. 30A to 30C show setting information transmitted from the health care worker-use information terminal 500 to the pharmaceutical injection device 1100.

The reference dose and the adjustment amount level are shown in FIG. 30A. When five-stage adjustment is performed according to the point total, the units of the pharmaceutical dose to be increased or decreased are shown in the adjustment amount levels 1 to 5. For example, the reference dose is set to 40 units, and +5 units is set in the case of the adjustment amount level 1. When three-stage adjustment is performed according to the point total, the increase or decrease units are set for the adjustment amount levels 1 to 3. In FIG. 30A, the adjustment amount levels are depicted for three-stage and five-stage, but just one of these may be transmitted to the pharmaceutical injection device 1100. Also, the configuration may be such that both sets of data are transmitted, and the patient 200 can select between five-stage adjustment and three-stage adjustment.

In FIG. 30B, change reason data is shown for dose adjustment, with blood glucose shown as change reason 1, meal size as change reason 2, activity as change reason 3, and "other" as change reason 4. For each change reason, examples of the text string that is selected include "high," "normal," and "low," and a reference for selecting the text string is given as help. For example, if high is selected for blood glucose level, which is change reason 1, a decision can be made by referring to the text in the help section: "Average blood glucose level for past 2 to 3 days: at least 200 mg/dL, before breakfast: at least 160 mg/dL."

FIG. 30C shows combinations of change reasons and weighting parameters. Also shown are determination thresholds for the adjustment amount level after weighting of the change reasons. For example, if the point total is +3 to +5, the pharmaceutical injection amount is adjusted to "high" as adjustment amount level 1.

Operation of Display Operation Controller

The operation of the display operation controller 1106 will now be described. The display operation controller 1106 controls display, etc., in the inputting of change reasons using the display component 5, the setting switches 6, etc. (S1430 in FIG. 27).

Figure 17C:
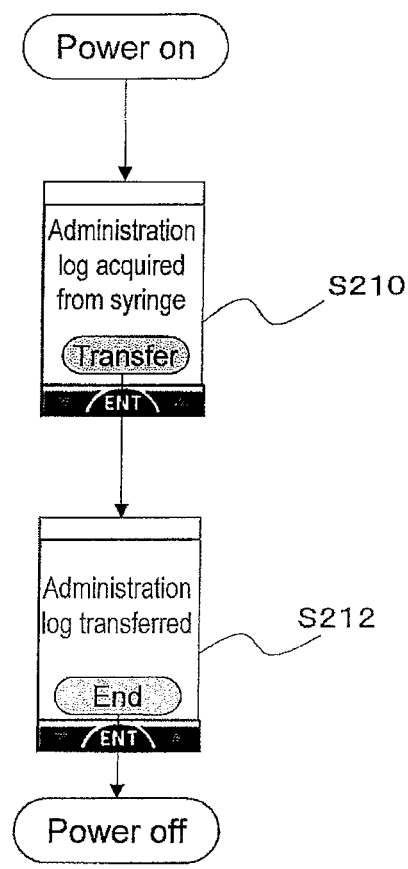
FIG. 17C is a flowchart of the display of the portable terminal in the control method shown in FIG. 16.

The display on the display component 5 of the pharmaceutical injection device 1100 in Embodiment 2 is the same as those in FIGS. 17A to 17C, and so will be described by using FIGS. 17A to 17C.

Figure 31:
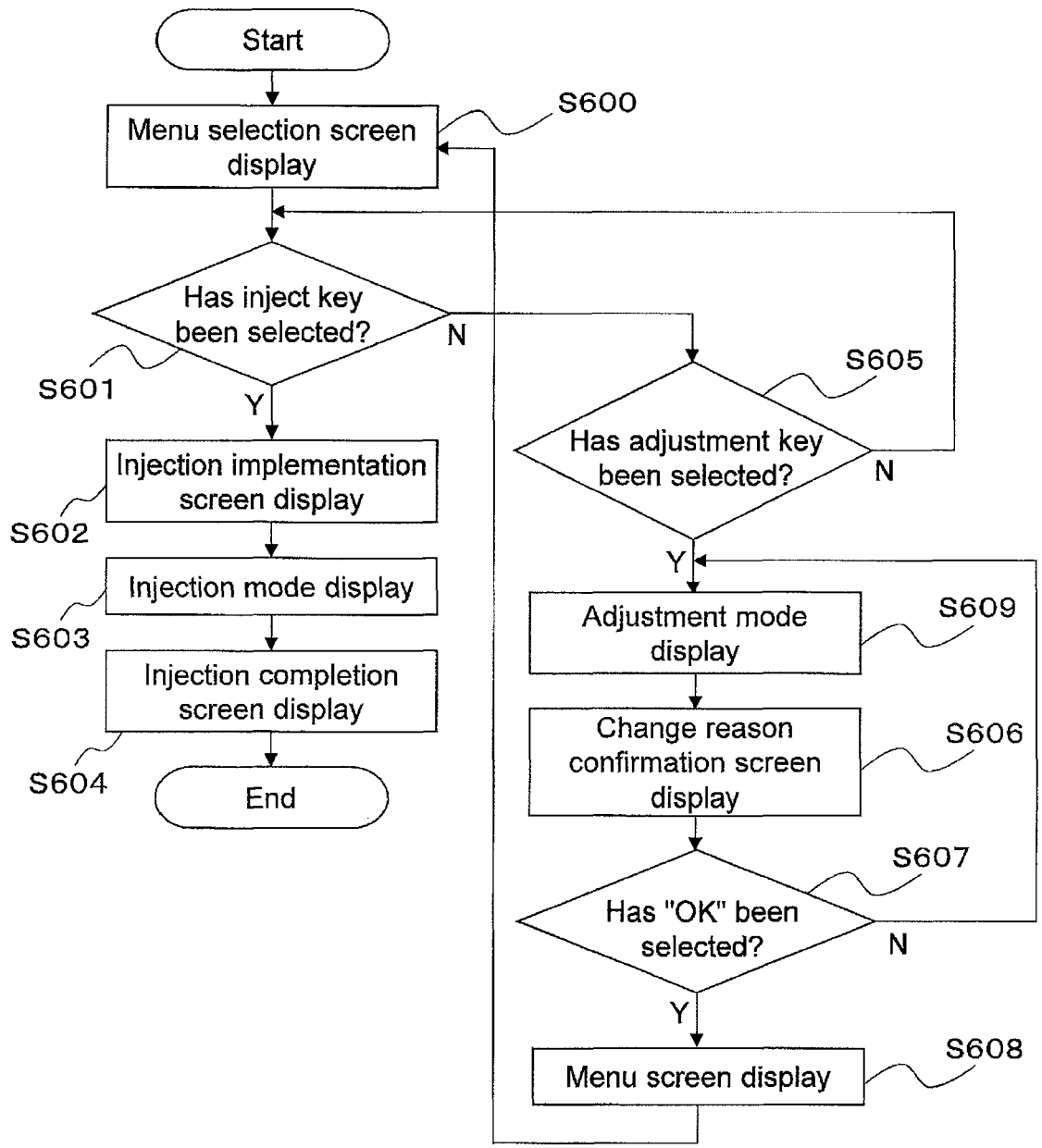
FIG. 31 is a flowchart of the operation of the display operation controller in FIG. 26.

FIG. 31 is a flowchart of the operation of the display operation controller 1106. As shown in FIG. 31, first a menu selection screen is displayed (S600, and S103 in reference FIG. 17A). Here, if the inject key 602 is selected (S601), an injection implementation screen is displayed on the display component 5 (S602), and pharmaceutical injection is performed using the pharmaceutical injection device 1100 in injection mode (S603). Once pharmaceutical injection is implemented, an injection completion screen is displayed on the display component 5 (S604). The display on the injection implementation screen, screen transition in injection mode, the injection completion screen, and so forth will not be described.

Meanwhile, if the adjust key 603 (S103 in reference FIG. 17A) is selected in S605, the display is given in adjustment mode (S609). The display in adjustment mode is the same up to the display of the adjustment screen in S105 to S112 described in Embodiment 1, and then a change reason confirmation screen is displayed (S606, and S113 in reference FIG. 17A).

When OK is then selected in S606, a menu screen displaying the pharmaceutical dose after adjustment is displayed (S608).

Operation of Change Reason Weighting Determination Component

Figure 32:
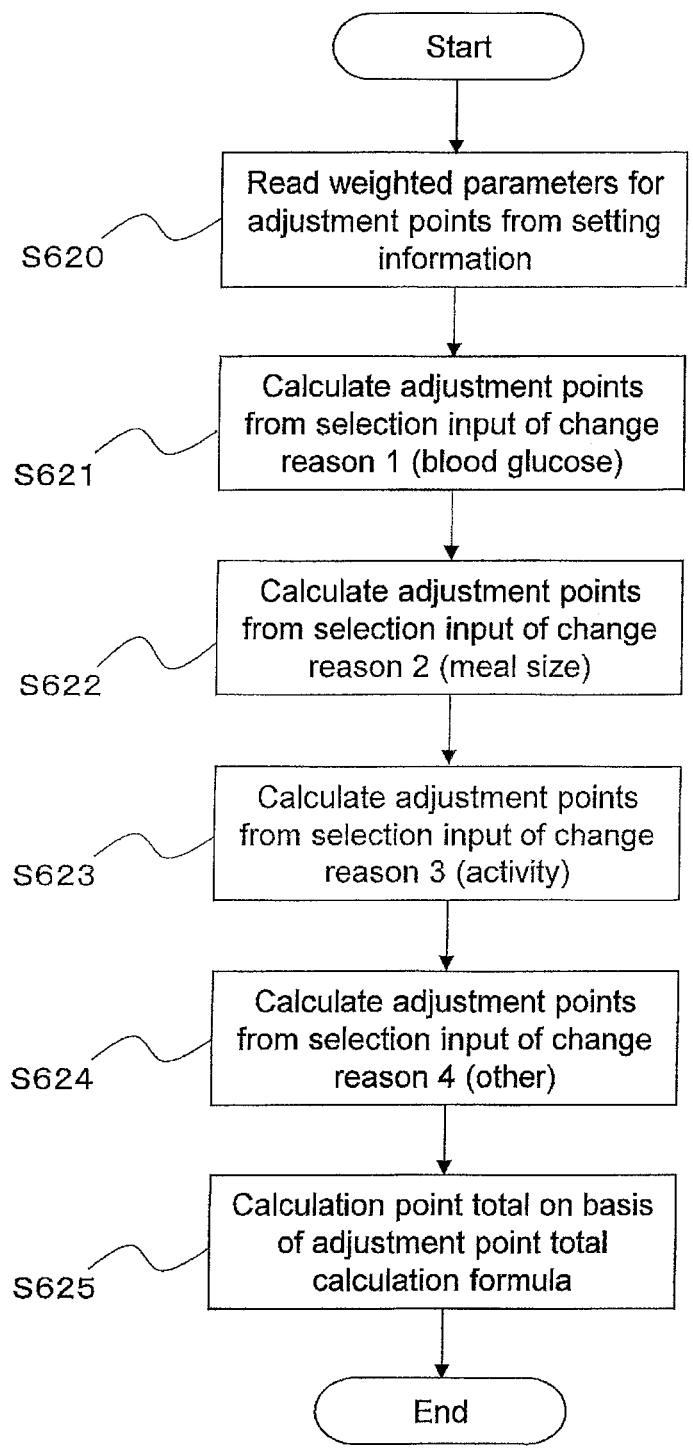
FIG. 32 is a flowchart of the operation of the change reason weighted determination criterion in FIG. 26.

The operation of the change reason weighting determination component 1102 will now be described. FIG. 32 is a flowchart of the operation of the change reason weighting determination component 1102. The change reason weighting determination component 1102 and the injection amount calculation processor 1103 (below-mentioned) calculate the pharmaceutical injection amount from the inputted change reasons on the basis of the received setting information (S1440 in FIG. 27).

The change reason weighting determination component 1102 reads weighting parameters for adjustment points from the setting information memory 1101 (S620).

Then, the change reason weighting determination component 1102 calculates the adjustment points from the selection input for change reason 1 (blood glucose) given by the display operation controller 1106 (S621). Here, for example, if the patient 200 selects "high" for blood glucose in the case of five-stage weighting, the adjustment points for change reason 1 will be +2 points (FIGS. 30B and 30C).

Then, the change reason weighting determination component 1102 calculates the adjustment points from the selection input for change reason 2 (meal size) given by the display operation controller 1106 (S622). Here, for example, if the patient 200 selects "large" for meal size in the case of five-stage weighting, the adjustment points for change reason 2 will be +1.5 points (FIGS. 30B and 30C).

Then, the change reason weighting determination component 1102 calculates the adjustment points from the selection input for change reason 3 (activity) given by the display operation controller 1106 (S623). Here, for example, if the patient 200 selects "high" for the amount of activity in the case of five-stage weighting, the adjustment points for change reason 3 will be −1.0 point (FIGS. 30B and 30C).

Then, the change reason weighting determination component 1102 calculates the adjustment points from the selection input for change reason 4 (other) given by the display operation controller 1106 (S624). Here, for example, if the patient 200 selects "as scheduled" for administration date and time in the case of five-stage weighting, the adjustment points for change reason 4 will be 0 points (FIGS. 30B and 30C).

Then, the change reason weighting determination component 1102 calculates the point total on the basis of an adjustment point total calculation formula (S625). Using the above-mentioned change reasons 1 to 4 as an example, the point total is 2+1.5−1+0=2.5 points.

This point total is temporarily stored in the setting information memory 1101.

Operation of Injection Amount Calculation Processor

Figure 33:
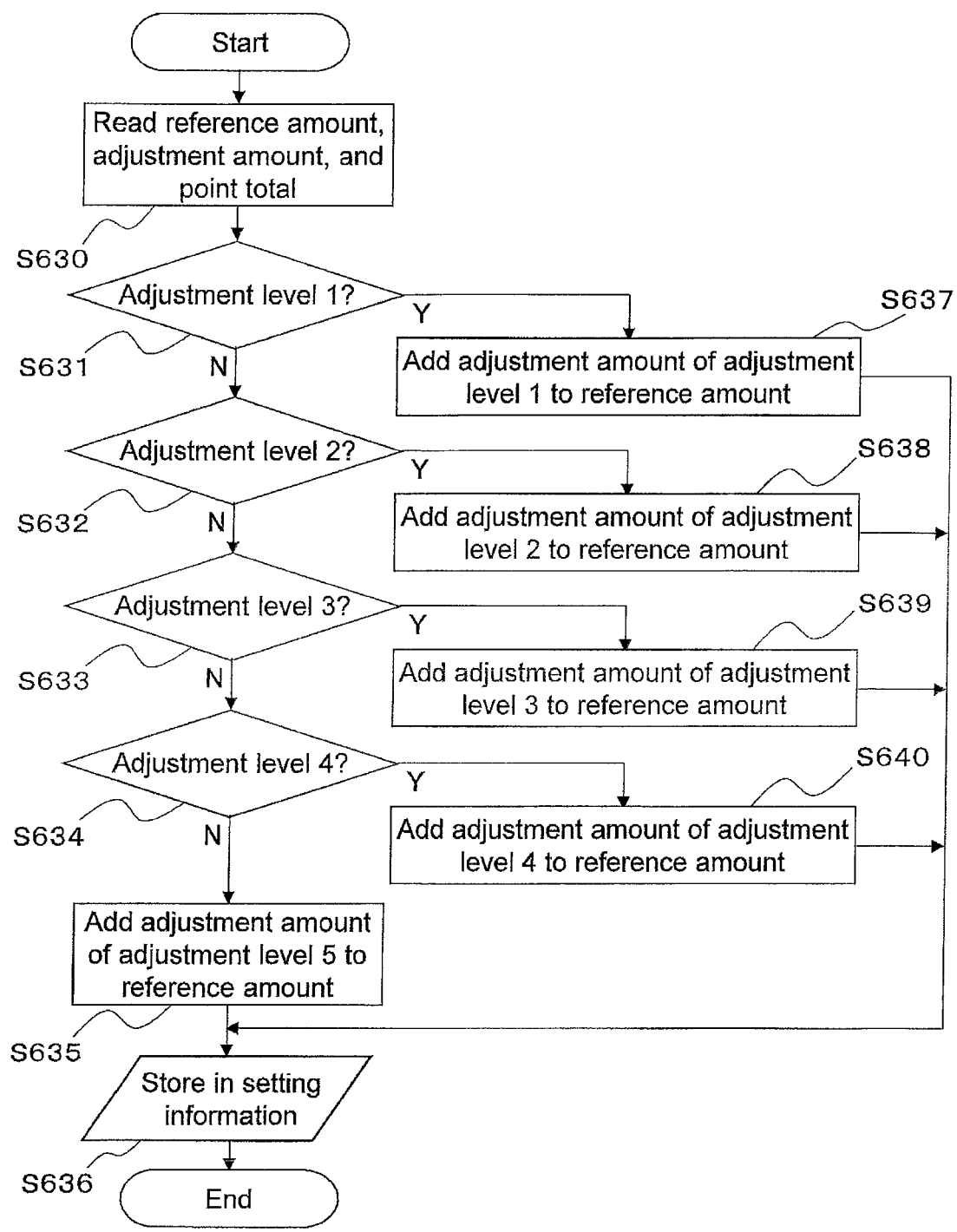
FIG. 33 is a flowchart of the operation of the injection amount computation processor in FIG. 26.

The operation of the injection amount calculation processor 1103 will now be described. FIG. 33 is a flowchart of the operation of the injection amount calculation processor 1103.

The injection amount calculation processor 1103 reads the reference amount, the adjustment amount, and the point total from the setting information memory 1101 (S630).

Next, the injection amount calculation processor 1103 determines from the point total whether or not the adjustment amount level is 1 (S631). If the point total corresponds to adjustment amount level 1, the adjustment amount of adjustment amount level 1 is added to the reference dose (S637). After this, the injection amount calculation processor 1103 stores the pharmaceutical dose after the addition of the adjustment amount of adjustment amount level 1 in the setting information memory 1101 (S636).

In S631, if the point total does not correspond to adjustment amount level 1, the injection amount calculation processor 1103 determines whether or not the point total corresponds to adjustment amount level 2 (S632). If the point total corresponds to adjustment amount level 2, the adjustment amount of adjustment amount level 2 is added to the reference dose (S638). After this, the injection amount calculation processor 1103 stores the pharmaceutical dose after the addition of the adjustment amount of adjustment amount level 2 in the setting information memory 1101 (S636).

In S632, if the point total does not correspond to adjustment amount level 2, the injection amount calculation processor 1103 determines whether or not the point total corresponds to adjustment amount level 3 (S633). If the point total corresponds to adjustment amount level 3, the adjustment amount of adjustment amount level 3 is added to the reference dose (S639). After this, the injection amount calculation processor 1103 stores the pharmaceutical dose after the addition of the adjustment amount of adjustment amount level 3 in the setting information memory 1101 (S636).

In S633, if the point total does not correspond to adjustment amount level 3, the injection amount calculation processor 1103 determines whether or not the point total corresponds to adjustment amount level 4 (S634). If the point total corresponds to adjustment amount level 4, the adjustment amount of adjustment amount level 4 is added to the reference dose (S640). After this, the injection amount calculation processor 1103 stores the pharmaceutical dose after the addition of the adjustment amount of adjustment amount level 4 in the setting information memory 1101 (S636).

In S634, if the point total does not correspond to adjustment amount level 4, the injection amount calculation processor 1103 adds the adjustment amount of adjustment amount level 5 to the reference dose (S635). After this, the injection amount calculation processor 1103 stores the pharmaceutical dose after the addition of the adjustment amount of adjustment amount level 5 in the setting information memory 1101 (S636).

In the above example, since the point total is +2.5 points, it can be seen from FIG. 30C that this corresponds to adjustment amount level 2, which is "somewhat higher." At adjustment amount level 2, as shown in FIG. 30A, +2 units are added to the reference dose. If we let the reference dose be 40 units, then the pharmaceutical dose after addition becomes 42 units (U). This pharmaceutical dose is stored in the setting information memory 1101.

Operation of Administration Log Memory

The operation of the administration log memory after completion of pharmaceutical administration will now be described.

Figure 34:
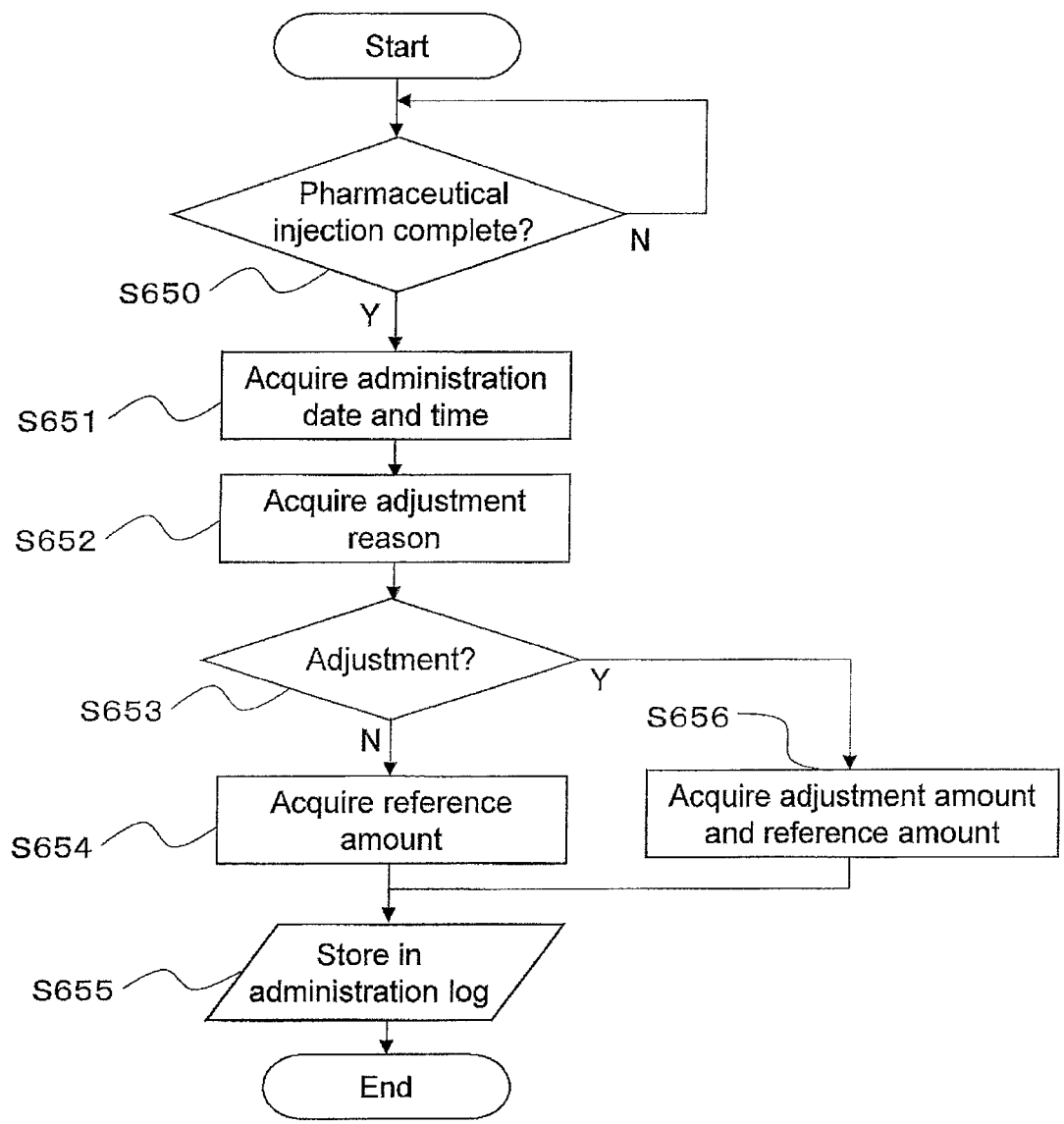
FIG. 34 is a flowchart of the operation of the administration log memory in FIG. 26.

FIG. 34 is a flowchart of the operation of the administration log memory. When pharmaceutical administration is complete (S650, and S1450 in FIG. 27), the administration log memory 1104 acquires the administration date and time from the time management controller 1112 (S651).

Then, the administration log memory 1104 acquires the change reasons from the change reason weighting determination component 1102 (S652).

The administration log memory 1104 acquires the adjustment amount and the reference amount if there is to be adjustment in S653 (S656). If there is no adjustment, just the reference amount is acquired (S654).

Next, the administration log memory 1104 stores the acquired reference amount, or the reference amount and the adjustment amount, in the pharmaceutical administration history (administration log) (S655, and S1460 in FIG. 27).

Operation of Communication Controller

When the patient 200 visits the physician 501 and tries to examine the pharmaceutical dose, as shown in S665 and S666 in FIG. 28, the communication controller 1111 transmits pharmaceutical administration history (administration log) data to the health care worker-use information terminal 500 via the near field communication component 25a, and performs communication end processing (S664, and S1470 in FIG. 27).

As shown in S1410 in FIG. 27, the health care worker-use information terminal 500 receives the pharmaceutical administration history (administration log) data through the near field communication component 52.

The data shown in FIG. 35 (administration date, administration time, reference dose, adjustment dose, etc.) is an example of the data transmitted by the communication controller 1111 to the health care worker-use information terminal 500. Consequently, a graph such as that shown in FIGS. 19 and 20, for example, can be displayed on the health care worker-use information terminal 500, and the physician 501 can give advice to the patient 200.

3. Main Features 3-1

The pharmaceutical injection device 1100 in Embodiment 2 comprises the cartridge holder 7, the main body case 1, the piston 10, the piston drive mechanism 101, the display component 5, the setting switches 6 (an example of a third input component), the near field communication component 25a (an example of a fourth receiver), the setting information memory 1101, the change reason weighting determination component 1102, and the injection amount calculation processor 1103 (an example of a pharmaceutical injection amount computer).

The cartridge holder 7 allows the pharmaceutical cartridge 9 to be mounted to it. The cartridge holder 7 is provided openably and closeably to the main body case 1. The piston 10 can be inserted into the pharmaceutical cartridge 9 mounted to the cartridge holder 7 inside the main body case 1. The piston drive mechanism 101 moves the piston 10 so that it is inserted into the pharmaceutical cartridge 9.

The display component 5 and the setting switches 6 are used by the patient 200 to input pharmaceutical injection amount setting conditions (change reasons, etc.) for setting the pharmaceutical injection amount. The near field communication component 25a is able to receive setting information (reference dose, adjustment amount level, etc.) from the health care worker-use information terminal 500 to which is inputted setting information for setting the pharmaceutical injection amount. The setting information memory 1101 stores the received setting information. The change reason weighting determination component 1102 and the injection amount calculation processor 1103 calculate the pharmaceutical injection amount on the basis of the setting information, from the inputted pharmaceutical injection amount setting conditions.

Consequently, if the patient 200 wishes to change the pharmaceutical injection amount, the pharmaceutical injection device 1100 can adjust the reference amount by calculating the adjustment amount on the basis of the setting information inputted by the physician 501.

Accordingly, the patient 200 does not have to visit the physician 501 every time he wishes to change the pharmaceutical injection amount, which is more convenient.

3-2

The pharmaceutical injection device 1100 in Embodiment 2 further comprises the near field communication component 25a (an example of a fourth transmitter) that transmits information related to the pharmaceutical administration history (administration log) to the health care worker-use information terminal 500.

This allows the physician 501 to refer to the pharmaceutical administration history (administration log) and give the patient 200 the appropriate advice.

3-3

The method for controlling a pharmaceutical injection system in Embodiment 2 is a method for controlling a pharmaceutical injection system that comprises the pharmaceutical injection device 1100 for injecting a pharmaceutical, and the health care worker-use information terminal 500 that is able to transmit setting information for setting the pharmaceutical injection amount to the pharmaceutical injection device 1100, said method comprising S1310 (an example of a third input step), S1320 (an example of a fourth transmission step), S1410 (an example of a fourth reception step), S1420 (an example of a second storage step), S1430 (an example of a fourth input step), S1440 (an example of a computation step), and S1460 (an example of a third storage step). S1310 (an example of a third input step) involves inputting a determination criterion for determining the validity of a pharmaceutical injection amount as setting information to the health care worker-use information terminal 500. S1320 (an example of a fourth transmission step) involves transmitting the inputted setting information from the health care worker-use information terminal 500 to the pharmaceutical injection device 1100. S1410 (an example of a fourth reception step) involves the pharmaceutical injection device 1100 receiving the setting information transmitted from the health care worker-use information terminal 500. S1420 (an example of a second storage step) involves storing the received setting information in the pharmaceutical injection device 1100. S1430 (an example of a fourth input step) involves inputting change reasons (an example of pharmaceutical injection amount setting conditions) for setting the pharmaceutical injection amount, to the pharmaceutical injection device 1100. S1440 (an example of a computation step) involves computing the pharmaceutical injection amount on the basis of the setting information, from the inputted change reasons (an example of pharmaceutical injection amount setting conditions). S1460 (an example of a third storage step) involves the pharmaceutical injection device 1100 storing the pharmaceutical injection amount as information related to the pharmaceutical administration history (administration log).

3-4

The method for controlling a pharmaceutical injection system in Embodiment 2 further comprises S1470 (an example of a fifth transmission step). S1470 (an example of a fifth transmission step) involves transmitting information related to the pharmaceutical administration history (administration log) from the pharmaceutical injection device 1100 to the health care worker-use information terminal 500.

4. Other Embodiments

Embodiments of the present invention are described above, but the present invention is not limited to or by the above embodiments, and various modifications are possible without departing from the gist of the invention. What was stated in the other embodiments given in Embodiment 1 above can also be suitably applied to Embodiment 2.

(A)

With the pharmaceutical injection system in Embodiment 2, communication between the pharmaceutical injection device 1100 and the health care worker-use information terminal 500 involves the use of near field communication provided by the near field communication component 25a and the near field communication component 52 (examples of NFC), but this is not the only option, and communication may instead be performed via the Internet or the like.

INDUSTRIAL APPLICABILITY

With the portable terminal, health care worker-use information terminal, pharmaceutical injection device, and pharmaceutical injection system of the present invention, the pharmaceutical injection amount can be changed without having to go to a treatment facility, which is more convenient for the user, and these are expected to find application to pharmaceutical injection devices and the like that are used for injecting insulin, growth hormones, and so forth.

REFERENCE SIGNS LIST 1 main body case
2 power switch
3 injection needle mounting component
4 pharmaceutical injection switch
5 display component
6 setting switch
7 cartridge holder
8 insertion opening
9 pharmaceutical cartridge
10 piston
11 feed screw
12 gear
13 motor
14 opening
15 injection needle detector switch
16 injection needle
17 shaft support
18 eject spring
19 latched component
20 ejector tab
21 spring
22 lever
22a, 22b protrusion
23 home point sensor
24 opening and closing detector switch
25 controller
25a near field communication component (an example of a third receiver, and an example of a fourth receiver)
26 battery
27 motor control circuit
28 encoder
29 buzzer control circuit
30 buzzer
31 display circuit
32 memory
33 timer
34 near field communication component (an example of a second transmitter)
35 controller
36 communication component (an example of a first transmitter, and an example of a first receiver)
37 memory (an example of a first memory)
38 display component (an example of first display component)
39 input component (an example of a first input component)
40 power switch
41 acceleration sensor
42 brightness sensor 43 microphone
44 battery
45 sounder
46 GPS
47 communication component (an example of a second receiver, and an example of a third transmitter)
48 controller
49 memory (an example of a second memory)
50 display component (an example of second display component)
51 input component (an example of a second input component)
52 near field communication component
53 external storage device
100 pharmaceutical injection device (Embodiment 1)
101 piston drive mechanism
200 patient
300 portable terminal
400 network
500 health care worker-use information terminal
501 physician
1100 pharmaceutical injection device (Embodiment 2)

What is claimed is:

1. A pharmaceutical injection system, comprising:
a pharmaceutical injection device configured to inject a pharmaceutical;
a portable terminal configured to set a pharmaceutical injection amount for the pharmaceutical injection device; and
a health care worker-use information terminal capable of communicating with the portable terminal,
wherein the portable terminal has:
 a first input component configured to have inputted therein pharmaceutical injection amount setting conditions for setting the pharmaceutical injection amount;
 a first transmitter configured to transmit the pharmaceutical injection amount setting conditions to the health care worker-use information terminal;
 a first receiver configured to receive from the health care worker-use information terminal the pharmaceutical injection amount set on the basis of the pharmaceutical injection amount setting conditions; and
 a second transmitter configured to transmit the received pharmaceutical injection amount to the pharmaceutical injection device,
 wherein the first input component is configured to have input therein information related to an adjustment amount for adjusting the pharmaceutical injection amount and to the pharmaceutical injection amount setting conditions,
 the pharmaceutical injection amount setting conditions including at least one of blood glucose level, meal size, amount of activity, and scheduled administration date and time as a change reason, and
 the information related to the adjustment amount being the adjustment amount level of several stages;
 wherein the first transmitter is configured to transmit the information related to the adjustment amount to the health care worker-use information terminal;
wherein the health care worker-use information terminal has:
 a second receiver configured to receive the pharmaceutical injection amount setting conditions transmitted from the portable terminal;
 a second input component configured to have the pharmaceutical injection amount set on the basis of the pharmaceutical injection amount setting conditions having been received;
 a third transmitter configured to transmit the inputted pharmaceutical injection amount to the portable terminal; and
 a worker-use information terminal display component;
 wherein the second input component is configured to have input therein a determination criterion that is set in order to determine validity of the adjustment amount,
 the determination criterion being a criterion for determining validity of the adjustment amount by a total of points obtained by converting weights of the change reason,
 wherein the worker-use information terminal display component is configured to display a determination result based on the adjustment amount, the pharmaceutical injection amount setting conditions, and the determination criterion,
 wherein the third transmitter is configured to transmit evaluation comments inputted through the second input component on the basis of the determination result, and advice to a user of the pharmaceutical injection device, along with the determination result, to the portable terminal, and
wherein the pharmaceutical injection device has:
 a cartridge holder configured to mount a pharmaceutical cartridge thereon;
 a main body case having the cartridge holder is openably and closeably provided thereto;
 a piston configured to be inserted into the pharmaceutical cartridge mounted to the cartridge holder inside the main body case;
 a piston drive mechanism configured to move the piston so as to insert the piston into the pharmaceutical cartridge;
 a third receiver configured to receive the pharmaceutical injection amount transmitted from the portable terminal; and
 a controller configured to drive the piston drive mechanism on the basis of the received pharmaceutical injection amount.

2. The pharmaceutical injection system according to claim 1, wherein the portable terminal further has:
a first memory configured to store the pharmaceutical injection amount setting conditions inputted to the first input component and to store the pharmaceutical injection amount received from the health care worker-use information terminal; and
a portable terminal display component configured to display in graph format the pharmaceutical injection amount and the pharmaceutical injection amount setting conditions stored in the first memory, and
wherein the health care worker-use information terminal further has:
a second memory configured to store the pharmaceutical injection amount setting conditions transmitted from the portable terminal, and to store the pharmaceutical injection amount inputted from the second input component; and
the worker-use information terminal display component being configured to display in graph format the pharmaceutical injection amount and the pharmaceutical injection amount setting conditions stored in the second memory.

3. The pharmaceutical injection system according to claim 1,
wherein the portable terminal has a first communication component configured to communicate with the pharmaceutical injection device,
the pharmaceutical injection device has a second communication component configured to communicate with the portable terminal,
the first communication component has the second transmitter,
the second communication component has the third receiver, and
the first communication component and the second communication component use near field communication (NFC).

4. A portable terminal that sets a pharmaceutical injection amount for a pharmaceutical injection device configured to inject a pharmaceutical, said portable terminal comprising:
a first input component configured to have input therein pharmaceutical injection amount setting conditions for setting the pharmaceutical injection amount;
a first transmitter configured to transmit the pharmaceutical injection amount setting conditions to a health care worker-use information terminal;
a first receiver configured to receive from the health care worker-use information terminal the pharmaceutical injection amount set on the basis of the pharmaceutical injection amount setting conditions, the pharmaceutical injection amount including an adjustment amount of the pharmaceutical injection amount having been validated on the basis of a determination criterion obtained by converting weights of a change reason to a criterion point system; and
a second transmitter configured to transmit the received pharmaceutical injection amount to the pharmaceutical injection device,
wherein the pharmaceutical injection amount setting conditions include at least one of blood glucose level, meal size, amount of activity, and scheduled administration date and time as a change reason.

5. A health care worker-use information terminal capable of communicating with a portable terminal configured to set a pharmaceutical injection amount for a pharmaceutical injection device configured to inject a pharmaceutical, the healthcare worker-use information terminal comprising:
a receiver configured to receive from the portable terminal pharmaceutical injection amount setting conditions for setting the pharmaceutical injection amount;
an input component configured to have the pharmaceutical injection amount set on the basis of the pharmaceutical injection amount setting conditions having been received, the pharmaceutical injection amount including an adjustment amount of the pharmaceutical injection amount being validated on the basis of determination criterion obtained by converting weights of a change reason to a criterion point system; and
a transmitter configured to transmit the pharmaceutical injection amount having been set to the portable terminal,
wherein the pharmaceutical injection amount setting conditions include at least one of blood glucose level, meal size, amount of activity, and scheduled administration date and time as a change reason.

6. The health care worker-use information terminal of claim 5, configured to allow the determination criterion to be set therein.

7. A pharmaceutical injection device that allows setting of a pharmaceutical injection amount from a portable terminal configured to have inputted therein pharmaceutical injection amount setting conditions for setting the pharmaceutical injection amount, the pharmaceutical injection device comprising:
a cartridge holder configured to mount a pharmaceutical cartridge thereon;
a main body case having the cartridge holder to be openably and closeably provided thereto;
a piston configured to be inserted into the pharmaceutical cartridge mounted to the cartridge holder inside the main body case;
a piston drive mechanism configured to move the piston so as to insert the piston into the pharmaceutical cartridge;
a receiver configured to receive from the portable terminal the pharmaceutical injection amount set on the basis of the pharmaceutical injection amount setting conditions transmitted from the portable terminal to a health care worker-use information terminal, the pharmaceutical injection amount including an adjustment amount of the pharmaceutical injection amount being validated on the basis of a determination criterion obtained by converting weights of a change reason to a criterion point system; and
a controller configured to drive the piston drive mechanism on the basis of the received pharmaceutical injection amount,
wherein the pharmaceutical injection amount setting conditions include at least one of blood glucose level, meal size, amount of activity, and scheduled administration date and time as a change reason.

8. A pharmaceutical injection device, comprising:
a cartridge holder configured to mount a pharmaceutical cartridge thereon;
a main body case having the cartridge holder to be openably and closeably provided thereto;
a piston configured to be inserted into the pharmaceutical cartridge mounted to the cartridge holder inside the main body case;
a piston drive mechanism configured to move the piston so as to insert the piston into the pharmaceutical cartridge;
an input component configured to have inputted therein pharmaceutical injection amount setting conditions for setting a pharmaceutical injection amount;
a receiver configured to receive setting information for setting the pharmaceutical injection amount, from a health care worker-use information terminal configured to have the setting information inputted to the health care worker-use information terminal;
a setting information memory configured to store the received setting information; and
a pharmaceutical injection amount computer configured to compute the pharmaceutical injection amount on the basis of the setting information, from the inputted pharmaceutical injection amount setting conditions, the pharmaceutical injection amount including an adjustment amount of the pharmaceutical injection amount being validated on the basis of determination criterion obtained by converting weights of a change reason to a criterion point system,
wherein the pharmaceutical injection amount setting conditions include at least one of blood glucose level, meal size, amount of activity, and scheduled administration date and time as a change reason.

9. The pharmaceutical injection device according to claim 8, further comprising a transmitter configured to transmit information related to pharmaceutical administration history to the health care worker-use information terminal.

10. A method for controlling a pharmaceutical injection system comprising a pharmaceutical injection device configured to inject a pharmaceutical, a portable terminal configured to set a pharmaceutical injection amount for the pharmaceutical injection device, and a health care worker-use information terminal capable of communicating with the portable terminal, the method for controlling the pharmaceutical injection system comprising:
- a first input step in which pharmaceutical injection amount setting conditions for setting the pharmaceutical injection amount are inputted to the portable terminal, wherein the pharmaceutical injection amount setting conditions include at least one of blood glucose level, meal size, amount of activity, and scheduled administration date and time as a change reason;
- a first transmission step in which the inputted pharmaceutical injection amount setting conditions are transmitted from the portable terminal to the health care worker-use information terminal;
- a first reception step in which the health care worker-use information terminal receives the pharmaceutical injection amount setting conditions transmitted from the portable terminal;
- a second input step in which the pharmaceutical injection amount set on the basis of the received pharmaceutical injection amount setting conditions is inputted to the health care worker-use information terminal, wherein the pharmaceutical injection amount includes an adjustment amount;
- a determination step at the health care worker-use information terminal in which a validity of the determination amount is determined based on a determination criterion, which is a criterion for determining validity of the adjustment amount by a total of points obtained by converting weights of the change reason;
- a display step in which the health care worker-use information terminal displays a determination result based on the adjustment amount, the pharmaceutical injection amount setting conditions, and the determination criterion;
- a second transmission step in which the pharmaceutical injection amount is transmitted from the health care worker-use information terminal to the portable terminal;
- a second reception step in which the pharmaceutical injection amount transmitted from the health care worker-use information terminal is received by the portable terminal;
- a third transmission step in which the pharmaceutical injection amount is transmitted from the portable terminal to the pharmaceutical injection device;
- a third reception step in which the pharmaceutical injection amount transmitted from the portable terminal is received by the pharmaceutical injection device; and
- a first storage step in which the pharmaceutical injection amount is stored by the pharmaceutical injection device; and
- a fourth transmission step in which evaluation comments on the basis of the determination result, and advice to a user of the pharmaceutical injection device, along with the determination result, input through the health care worker-use terminal, are transmitted to the portable terminal from the health care worker-use terminal.

11. A method for controlling a pharmaceutical injection system comprising a pharmaceutical injection device configured to inject a pharmaceutical and a health care worker-use information terminal capable of transmitting setting information for setting a pharmaceutical injection amount for the pharmaceutical injection device, the method for controlling the pharmaceutical injection system comprising:
- an obtaining step of obtaining determination criterion by converting weights of a change reason to a criterion point system;
- an input step in which a the determination criterion, for determining validity of the pharmaceutical injection amount, as setting information is inputted to the health care worker-use information terminal, the determination criterion further provided for determining validity of an adjustment amount of the pharmaceutical injection amount;
- a display step in which the health care worker-use information terminal displays a determination result based on the adjustment amount, the determination criterion and pharmaceutical injection amount setting conditions, wherein the pharmaceutical injection amount setting conditions including at least one of blood glucose level, meal size, amount of activity, and scheduled administration date and time as the change reason;
- a step in which the inputted setting information is transmitted from the health care worker-use information terminal to the pharmaceutical injection device;
- a reception step in which the setting information transmitted from the health care worker-use information terminal is received by the pharmaceutical injection device;
- a storage step in which the received setting information is stored by the pharmaceutical injection device;
- another input step in which pharmaceutical injection amount setting conditions for setting the pharmaceutical injection amount are inputted to the pharmaceutical injection device;
- a computation step in which the pharmaceutical injection amount is computed on the basis of the setting information from the inputted pharmaceutical injection amount setting conditions; and
- another storage step in which the pharmaceutical injection device stores the pharmaceutical injection amount as information related to pharmaceutical administration history.

12. The method for controlling the pharmaceutical injection system according to claim 11, further comprising another transmission step in which the information related to pharmaceutical administration history is transmitted from the pharmaceutical injection device to the health care worker-use information terminal.

* * * * *